US009931371B2

(12) United States Patent
Tan et al.

(10) Patent No.: US 9,931,371 B2
(45) Date of Patent: Apr. 3, 2018

(54) ANGIOPOIETIN-LIKE 4 AND A METHOD OF ITS USE IN WOUND HEALING

(71) Applicant: Nanyang Technological University, Singapore (SG)

(72) Inventors: Nguan Soon Tan, Singapore (SG); Han Chung Kelvin Chong, Singapore (SG)

(73) Assignee: Nanyang Technologies University, Singapore (SG)

( * ) Notice: Subject to any disclaimer, the term of this patent is extended or adjusted under 35 U.S.C. 154(b) by 0 days.

(21) Appl. No.: 14/415,399

(22) PCT Filed: Jul. 3, 2013

(86) PCT No.: PCT/SG2013/000275
§ 371 (c)(1),
(2) Date: Jan. 16, 2015

(87) PCT Pub. No.: WO2014/014410
PCT Pub. Date: Jan. 23, 2014

(65) Prior Publication Data
US 2015/0196616 A1 Jul. 16, 2015

Related U.S. Application Data

(60) Provisional application No. 61/673,463, filed on Jul. 19, 2012.

(51) Int. Cl.
*A61K 38/00* (2006.01)
*A61K 38/10* (2006.01)
*C07K 14/515* (2006.01)
*A61K 38/16* (2006.01)
*A61K 38/17* (2006.01)
*G01N 33/68* (2006.01)

(52) U.S. Cl.
CPC .............. *A61K 38/10* (2013.01); *A61K 38/16* (2013.01); *A61K 38/1709* (2013.01); *C07K 14/515* (2013.01); *G01N 33/6893* (2013.01); *G01N 2333/515* (2013.01)

(58) Field of Classification Search
None
See application file for complete search history.

(56) References Cited

U.S. PATENT DOCUMENTS

| 3,988,466 | A | * | 10/1976 | Takagi | A61K 31/405 514/400 |
| 7,371,384 | B2 | | 5/2008 | Gerber et al. | |
| 2006/0093606 | A1 | * | 5/2006 | Gerber | A01K 67/0276 424/145.1 |

FOREIGN PATENT DOCUMENTS

| CN | 101080419 A | 11/2007 |
| WO | 03/010205 A1 | 2/2003 |
| WO | 2006/014678 A2 | 2/2006 |
| WO | 2012/175745 A1 | 12/2012 |

OTHER PUBLICATIONS

Demling, Nutrition, Anabolism, and the Wound Healing Process: An Overview, Open Access of Plastic Surgery, 2009, pp. 65-94.*
Aktan, "iNOS-mediated nitric oxide production and its regulation," *Life Sciences* 75:639-653, 2004.
Blakytny et al., "Altered Molecular Mechanisms of Diabetic Foot Ulcers," *The International Journal of Lower Extremity Wounds* 8(2):95-104, Jun. 2009.
Bornstein et al., "Matricellular proteins: extracellular modulators of cell function," *Current Opinion in Cell Biology* 14(5):608-616, 2002.
Bornstein, "Matricellular proteins: an overview," *Matrix Biology* 19(7):555-556, Jul. 2000.
Braiman-Wiksman et al., "Novel Insights into Wound Healing Sequence of Events," *Toxicologic Pathology* 35(6):767-779, 2007.
Brem et al., "Cellular and molecular basis of wound healing in diabetes," *The Journal of Clinical Investigation* 117(5):1219-1222, May 2007.
Chin et al., "The influence of nitric oxide synthase 2 on cutaneous wound angiogenesis," *British Journal of Dermatology* 165:1223-1235, Aug. 2011.
Chong et al., "Matricellular Proteins: A Sticky Affair with Cancers," *Journal of Oncology 2012*, Feb. 2012, 17 pages.
Coulombe, "Wound Epithelialization: Accelerating the Pace of Discovery," *the Journal of Investigative Dermatology* 121(2):219-230, 2003.
Delmas, "Best Practice in the Assessment and Management of Diabetic Foot Ulcers," *Rehabilitation Nursing* 31(6):228-234, Nov./Dec. 2006.
Falanga, "Wound healing and its impairment in the diabetic foot," *Lancet* 366:1736-1743, Nov. 2005.
Galkowska et al., "Chemokines, cytokines, and growth factors in keratinocytes and dermal endothelial cells in the margin of chronic diabetic foot ulcers," *Wound Repair Regen* 14:558-565, May 2006.
Goh et al., "Angiopoietin-Like 4 Interacts with Integrins β1 and β5 to Modulate Keratinocyte Migration," *The American Journal of Pathology* 177(6):2791-2803, Dec. 2010.
Goh et al., "Angiopoietin-like 4 Interacts with Matrix Proteins to Modulate Wound Healing," *The Journal of Biological Chemistry* 285(43):32999-33009, Oct. 2010.
Huang et al., "ANGPTL4 modulates vascular junction integrity by integrin signaling and disruption of intercellular VE-cadherin and claudin-5 clusters," *Blood* 118(14):3990-4002, Oct. 2011.
Ito et al., "Inhibition of Angiogenesis and Vascular Leakiness by Angiopoietin-Related Protein 4," *Cancer Research* 63:6651-6657, Oct. 2003.
Kuwano et al., "Analysis of Nitric Oxide-Stabilized mRNAs in Human Fibroblast Reveals HuR-Dependent Heme Oxygenase 1 Upregulation," *Molecular and Cellular Biology* 29(10):2622-2635, May 2009.
Le Jan et al., "Angiopoietin-Like 4 is a Proangiogenic Factor Produced during Ischemia and in Conventional Renal Cell Carcinoma," *American Journal of Pathology* 162(5):1521-1528, May 2003.
Luo et al., "Nitric oxide: a newly discovered function on wound healing," *Acta Pharmacologica Sinica* 26(3):259-264, Mar. 2005.

(Continued)

*Primary Examiner* — Thomas S Heard
(74) *Attorney, Agent, or Firm* — Seed IP Law Group LLP

(57) ABSTRACT

A method and a pharmaceutical composition for increasing wound healing in an individual in need thereof, the method comprising administering an angiopoietin like 4 (ANGPTL4) polypeptide or a therapeutically active fragment thereof.

3 Claims, 11 Drawing Sheets

(56) References Cited

OTHER PUBLICATIONS

Michalik et al., "Peroxisome proliferator-activated receptors (PPARs) in skin health, repair and disease," *Biochimica et Biophysica Acta* 1771(8):991-998, 2007.

Oike et al., "Angiopoietin-like proteins: potential new targets for metabolic syndrome therapy," *Trends Molecular Medicine* 11(10):473-479, Oct. 2005.

Padua et al., "TGFβ Primes Breast Tumors for Lung Metastasis Seeding through Angiopoietin-like 4," *Cell* 133(1):66-77, Apr. 2008.

Schäffer et al., "Diabetes-impaired healing and reduced wound nitric oxide synthesis: A possible pathophysiologic correlation," *Surgery* 121:513-519, Dec. 1997.

Sharma et al., "Differential Regulation of Angiogenic Genes in Diabetic Wound Healing," *Journal of Investigative Dermatology* 126:2323-2331, Jul. 2006.

Tan et al., "Essential role of Smad3 in the inhibition of inflammation-induced PPARβ/δ expression," *The EMBO Journal* 23(21):4211-4221, 2004.

Tan et al., "Smad3 Deficiency in Mice Protects Against Insulin Resistance and Obesity Induced by a High-Fat Diet," *Diabetes* 60:464-476, Feb. 2011.

Wang et al., "Nitric oxide activation of Erk1/2 regulates the stability and translation of mRNA transcripts containing CU-rich elements," *Nucleic Acids Research* 34(10):3044-3056, Jun. 2006.

Wang et al., "Nitric Oxide Synthase Expression and Nitric Oxide Production Are Reduced in Hypertrophic Scar Tissue and Fibroblasts," *J. Invest. Dermatol.* 108:438-444, 1997.

Werner et al., "Regulation of Wound Healing by Growth Factors and Cytokines," *Physiol. Rev.* 83:835-870, 2003.

Zhu et al., "Angiopoietin-like 4 Protein Elevates the Prosurvival Intracellular $O_2^-$:$H_2O_2$ Ratio and Confers Anoikis Resistance to Tumors," *Cancer Cell* 19:401-415, Mar. 2011.

Zhu et al., "Angiopoietin-like 4: a decade of research," *Biosci. Rep.* 32(3):211-219, 2012.

Pal et al., "Angiopoietin-Like 4 Regulates Epidermal Differentiation," *PLoS One* 6(9):e25377 (9 pages) (Sep. 2011).

Teo et al., "Angiopoietin-like 4 induces a β-catenin-mediated upregulation of ID3 in fibroblasts to reduce scar collagen expression," *Scientific Reports* 7:1-15 (published online Jul. 24, 2017).

Official Action from State Intellectual Property Office of China, dated Jun. 2, 2017, for Patent corresponding Application No. 201380044346.5, 11 pages, with translation.

\* cited by examiner

A

B

C

SEQUENCE LISTING

```
<160> NUMBER OF SEQ ID NOS: 164

<210> SEQ ID NO 1
<211> LENGTH: 222
<212> TYPE: PRT
<213> ORGANISM: Homo sapiens

<400> SEQUENCE: 1

Pro Arg Asp Cys Gln Glu Leu Phe Gln Val Gly Glu Arg Gln Ser Gly
1               5                   10                  15

Leu Phe Glu Ile Gln Pro Gln Gly Ser Pro Pro Phe Leu Val Asn Cys
            20                  25                  30

Lys Met Thr Ser Asp Gly Gly Trp Thr Val Ile Gln Arg Arg His Asp
        35                  40                  45

Gly Ser Val Asp Phe Asn Arg Pro Trp Glu Ala Tyr Lys Ala Gly Phe
    50                  55                  60

Gly Asp Pro His Gly Glu Phe Trp Leu Gly Leu Glu Lys Val His Ser
65                  70                  75                  80

Ile Thr Gly Asp Arg Asn Ser Arg Leu Ala Val Gln Leu Arg Asp Trp
                85                  90                  95

Asp Gly Asn Ala Glu Leu Leu Gln Phe Ser Val His Leu Gly Gly Glu
            100                 105                 110

Asp Thr Ala Tyr Ser Leu Gln Leu Thr Ala Pro Val Ala Gly Gln Leu
        115                 120                 125

Gly Ala Thr Thr Val Pro Pro Ser Gly Leu Ser Val Pro Phe Ser Thr
    130                 135                 140

Trp Asp Gln Asp His Asp Leu Arg Arg Asp Lys Asn Cys Ala Lys Ser
145                 150                 155                 160

Leu Ser Gly Gly Trp Trp Phe Gly Thr Cys Ser His Ser Asn Leu Asn
                165                 170                 175

Gly Gln Tyr Phe Arg Ser Ile Pro Gln Gln Arg Gln Lys Leu Lys Lys
            180                 185                 190

Gly Ile Phe Trp Lys Thr Trp Arg Gly Arg Tyr Tyr Pro Leu Gln Ala
        195                 200                 205

Thr Thr Met Leu Ile Gln Pro Met Ala Ala Glu Ala Ala Ser
    210                 215                 220

<210> SEQ ID NO 2
<211> LENGTH: 14
<212> TYPE: PRT
<213> ORGANISM: Homo sapiens

<400> SEQUENCE: 2

Tyr Phe Arg Ser Ile Pro Gln Gln Arg Gln Lys Leu Lys Lys
1               5                   10

<210> SEQ ID NO 3
<211> LENGTH: 21
<212> TYPE: DNA
<213> ORGANISM: Artificial Sequence
```

```
<220> FEATURE:
<223> OTHER INFORMATION: genortyping forward primer

<400> SEQUENCE: 3
tgtccaagat ggaccagact c                                              21

<210> SEQ ID NO 4
<211> LENGTH: 21
<212> TYPE: DNA
<213> ORGANISM: Artificial Sequence
<220> FEATURE:
<223> OTHER INFORMATION: genotyping reverse primer

<400> SEQUENCE: 4
actggtctga ggcagggagc a                                              21

<210> SEQ ID NO 5
<211> LENGTH: 19
<212> TYPE: DNA
<213> ORGANISM: Artificial Sequence
<220> FEATURE:
<223> OTHER INFORMATION: ADAM9 forward primer

<400> SEQUENCE: 5
ggacggaacc agactgctg                                                 19

<210> SEQ ID NO 6
<211> LENGTH: 20
<212> TYPE: DNA
<213> ORGANISM: Artificial Sequence
<220> FEATURE:
<223> OTHER INFORMATION: ADAM9 reverse primer

<400> SEQUENCE: 6
ccactgaaca aagttgccca                                                20

<210> SEQ ID NO 7
<211> LENGTH: 22
<212> TYPE: DNA
<213> ORGANISM: Artificial Sequence
<220> FEATURE:
<223> OTHER INFORMATION: ADIPOQ forward primer

<400> SEQUENCE: 7
agccgcttat atgtatcgct ca                                             22

<210> SEQ ID NO 8
<211> LENGTH: 23
<212> TYPE: DNA
<213> ORGANISM: Artificial Sequence
<220> FEATURE:
<223> OTHER INFORMATION: ADIPOQ reverse primer

<400> SEQUENCE: 8
tgccgtcata atgattctgt tgg                                            23

<210> SEQ ID NO 9
<211> LENGTH: 21
<212> TYPE: DNA
<213> ORGANISM: Artificial Sequence
<220> FEATURE:
<223> OTHER INFORMATION: AKT1 forward primer

<400> SEQUENCE: 9
ccaaggccca acacctttat c                                              21
```

<210> SEQ ID NO 10
<211> LENGTH: 21
<212> TYPE: DNA
<213> ORGANISM: Artificial Sequence
<220> FEATURE:
<223> OTHER INFORMATION: AKT1 reverse primer

<400> SEQUENCE: 10
ttcctgcctc ttgagtccat c                                        21

<210> SEQ ID NO 11
<211> LENGTH: 23
<212> TYPE: DNA
<213> ORGANISM: Artificial Sequence
<220> FEATURE:
<223> OTHER INFORMATION: ANGPT1 foward primer

<400> SEQUENCE: 11
tgcactaaag aaggtgtttt gct                                      23

<210> SEQ ID NO 12
<211> LENGTH: 23
<212> TYPE: DNA
<213> ORGANISM: Artificial Sequence
<220> FEATURE:
<223> OTHER INFORMATION: ANGPT1 reverse primer

<400> SEQUENCE: 12
cctcccccat tcacatccat att                                      23

<210> SEQ ID NO 13
<211> LENGTH: 19
<212> TYPE: DNA
<213> ORGANISM: Artificial Sequence
<220> FEATURE:
<223> OTHER INFORMATION: ANGPT2 forward primer

<400> SEQUENCE: 13
cgaggcgcat tcgctgtat                                           19

<210> SEQ ID NO 14
<211> LENGTH: 23
<212> TYPE: DNA
<213> ORGANISM: Artificial Sequence
<220> FEATURE:
<223> OTHER INFORMATION: ANGPT2 reverse primer

<400> SEQUENCE: 14
ggctgatgct acttattttg ccc                                      23

<210> SEQ ID NO 15
<211> LENGTH: 19
<212> TYPE: DNA
<213> ORGANISM: Artificial Sequence
<220> FEATURE:
<223> OTHER INFORMATION: ANGPTL4 forward primer

<400> SEQUENCE: 15
tccaacgcca cccacttac                                           19

<210> SEQ ID NO 16
<211> LENGTH: 23
<212> TYPE: DNA
<213> ORGANISM: Artificial Sequence
<220> FEATURE:
<223> OTHER INFORMATION: ANGPTL4 reverse primer

```
<400> SEQUENCE: 16
tgaagtcatc tcacagttga cca                                              23

<210> SEQ ID NO 17
<211> LENGTH: 23
<212> TYPE: DNA
<213> ORGANISM: Artificial Sequence
<220> FEATURE:
<223> OTHER INFORMATION: CCL2 forward primer

<400> SEQUENCE: 17
ttaaaaacct ggatcggaac caa                                              23

<210> SEQ ID NO 18
<211> LENGTH: 23
<212> TYPE: DNA
<213> ORGANISM: Artificial Sequence
<220> FEATURE:
<223> OTHER INFORMATION: CCL2 reverse primer

<400> SEQUENCE: 18
gcattagctt cagatttacg ggt                                              23

<210> SEQ ID NO 19
<211> LENGTH: 22
<212> TYPE: DNA
<213> ORGANISM: Artificial Sequence
<220> FEATURE:
<223> OTHER INFORMATION: CCL11 forward primer

<400> SEQUENCE: 19
gaatcaccaa caacagatgc ac                                               22

<210> SEQ ID NO 20
<211> LENGTH: 21
<212> TYPE: DNA
<213> ORGANISM: Artificial Sequence
<220> FEATURE:
<223> OTHER INFORMATION: CCL11 reverse primer

<400> SEQUENCE: 20
atcctggacc cacttcttct t                                                21

<210> SEQ ID NO 21
<211> LENGTH: 21
<212> TYPE: DNA
<213> ORGANISM: Artificial Sequence
<220> FEATURE:
<223> OTHER INFORMATION: CDK4 forward primer

<400> SEQUENCE: 21
ccaatgttgt acggctgatg g                                                21

<210> SEQ ID NO 22
<211> LENGTH: 21
<212> TYPE: DNA
<213> ORGANISM: Artificial Sequence
<220> FEATURE:
<223> OTHER INFORMATION: CDK4 reverse primer

<400> SEQUENCE: 22
tgtccaggta tgtcctcagg t                                                21

<210> SEQ ID NO 23
```

```
<211> LENGTH: 19
<212> TYPE: DNA
<213> ORGANISM: Artificial Sequence
<220> FEATURE:
<223> OTHER INFORMATION: CDKN2B forward primer

<400> SEQUENCE: 23
ccctgccacc cttaccaga                                                      19

<210> SEQ ID NO 24
<211> LENGTH: 21
<212> TYPE: DNA
<213> ORGANISM: Artificial Sequence
<220> FEATURE:
<223> OTHER INFORMATION: CDKN2B reverse primer

<400> SEQUENCE: 24
cagatacctc gcaatgtcac g                                                   21

<210> SEQ ID NO 25
<211> LENGTH: 20
<212> TYPE: DNA
<213> ORGANISM: Artificial Sequence
<220> FEATURE:
<223> OTHER INFORMATION: CSTA forward primer

<400> SEQUENCE: 25
tacggaggtg tttcagaggc                                                     20

<210> SEQ ID NO 26
<211> LENGTH: 19
<212> TYPE: DNA
<213> ORGANISM: Artificial Sequence
<220> FEATURE:
<223> OTHER INFORMATION: CSTA reverse primer

<400> SEQUENCE: 26
cagcgacggc ttgagtttt                                                      19

<210> SEQ ID NO 27
<211> LENGTH: 23
<212> TYPE: DNA
<213> ORGANISM: Artificial Sequence
<220> FEATURE:
<223> OTHER INFORMATION: CXCL1 forward primer

<400> SEQUENCE: 27
ctgggattca cctcaagaac atc                                                 23

<210> SEQ ID NO 28
<211> LENGTH: 19
<212> TYPE: DNA
<213> ORGANISM: Artificial Sequence
<220> FEATURE:
<223> OTHER INFORMATION: CXCL1 reverse primer

<400> SEQUENCE: 28
cagggtcaag gcaagcctc                                                      19

<210> SEQ ID NO 29
<211> LENGTH: 21
<212> TYPE: DNA
<213> ORGANISM: Artificial Sequence
<220> FEATURE:
<223> OTHER INFORMATION: CXCL5 forward primer

<400> SEQUENCE: 29
```
tgcgttgtgt ttgcttaacc g                                              21

<210> SEQ ID NO 30
<211> LENGTH: 21
<212> TYPE: DNA
<213> ORGANISM: Artificial Sequence
<220> FEATURE:
<223> OTHER INFORMATION: CXCL5 reverse primer

<400> SEQUENCE: 30
agctatgact tccaccgtag g                                              21

<210> SEQ ID NO 31
<211> LENGTH: 21
<212> TYPE: DNA
<213> ORGANISM: Artificial Sequence
<220> FEATURE:
<223> OTHER INFORMATION: CXCL9 forward primer

<400> SEQUENCE: 31
gaacggagat caaacctgcc t                                              21

<210> SEQ ID NO 32
<211> LENGTH: 22
<212> TYPE: DNA
<213> ORGANISM: Artificial Sequence
<220> FEATURE:
<223> OTHER INFORMATION: CXCL9 reverse primer

<400> SEQUENCE: 32
tgtagtcttc cttgaacgac ga                                             22

<210> SEQ ID NO 33
<211> LENGTH: 21
<212> TYPE: DNA
<213> ORGANISM: Artificial Sequence
<220> FEATURE:
<223> OTHER INFORMATION: CXCL10 forward primer

<400> SEQUENCE: 33
ccaagtgctg ccgtcatttt c                                              21

<210> SEQ ID NO 34
<211> LENGTH: 21
<212> TYPE: DNA
<213> ORGANISM: Artificial Sequence
<220> FEATURE:
<223> OTHER INFORMATION: CXCL10 reverse primer

<400> SEQUENCE: 34
ggctcgcagg gatgatttca a                                              21

<210> SEQ ID NO 35
<211> LENGTH: 21
<212> TYPE: DNA
<213> ORGANISM: Artificial Sequence
<220> FEATURE:
<223> OTHER INFORMATION: EGRF forward primer

<400> SEQUENCE: 35
gggagcattt ggcacagtgt a                                              21

<210> SEQ ID NO 36
<211> LENGTH: 22
<212> TYPE: DNA

```
<213> ORGANISM: Artificial Sequence
<220> FEATURE:
<223> OTHER INFORMATION: EGRF reverse primer

<400> SEQUENCE: 36
gccatcacat aggcttcgtc aa                                              22

<210> SEQ ID NO 37
<211> LENGTH: 21
<212> TYPE: DNA
<213> ORGANISM: Artificial Sequence
<220> FEATURE:
<223> OTHER INFORMATION: EPHA3 forward primer

<400> SEQUENCE: 37
ttctggtcgg gaggttttgt g                                               21

<210> SEQ ID NO 38
<211> LENGTH: 21
<212> TYPE: DNA
<213> ORGANISM: Artificial Sequence
<220> FEATURE:
<223> OTHER INFORMATION: EPHA3 reverse primer

<400> SEQUENCE: 38
actgcttgag tagggtcttc a                                               21

<210> SEQ ID NO 39
<211> LENGTH: 22
<212> TYPE: DNA
<213> ORGANISM: Artificial Sequence
<220> FEATURE:
<223> OTHER INFORMATION: EPHB3 forward primer

<400> SEQUENCE: 39
accgtaagag actgtaacag ca                                              22

<210> SEQ ID NO 40
<211> LENGTH: 21
<212> TYPE: DNA
<213> ORGANISM: Artificial Sequence
<220> FEATURE:
<223> OTHER INFORMATION: EPHB3 reverse primer

<400> SEQUENCE: 40 gtccacttc acgtaggggt t                                                21

<210> SEQ ID NO 41
<211> LENGTH: 20
<212> TYPE: DNA
<213> ORGANISM: Artificial Sequence
<220> FEATURE:
<223> OTHER INFORMATION: FAS forward primer

<400> SEQUENCE: 41
agagatcccg agacgcttct                                                 20

<210> SEQ ID NO 42
<211> LENGTH: 21
<212> TYPE: DNA
<213> ORGANISM: Artificial Sequence
<220> FEATURE:
<223> OTHER INFORMATION: FAS reverse primer

<400> SEQUENCE: 42
gcctggtagg cattctgtag t                                               21
```

<210> SEQ ID NO 43
<211> LENGTH: 19
<212> TYPE: DNA
<213> ORGANISM: Artificial Sequence
<220> FEATURE:
<223> OTHER INFORMATION: FGF1 forward primer

<400> SEQUENCE: 43
cagctcagtg cggaaagtg                                              19

<210> SEQ ID NO 44
<211> LENGTH: 21
<212> TYPE: DNA
<213> ORGANISM: Artificial Sequence
<220> FEATURE:
<223> OTHER INFORMATION: FGF1 reverse primer

<400> SEQUENCE: 44
tgtctgcgag ccgtataaaa g                                           21

<210> SEQ ID NO 45
<211> LENGTH: 20
<212> TYPE: DNA
<213> ORGANISM: Artificial Sequence
<220> FEATURE:
<223> OTHER INFORMATION: FGF2

<400> SEQUENCE: 45
gcgacccaca cgtcaaacta                                             20

<210> SEQ ID NO 46
<211> LENGTH: 23
<212> TYPE: DNA
<213> ORGANISM: Artificial Sequence
<220> FEATURE:
<223> OTHER INFORMATION: FGF2 reverse primer

<400> SEQUENCE: 46
tccatcttcc ttcatagcaa ggt                                         23

<210> SEQ ID NO 47
<211> LENGTH: 20
<212> TYPE: DNA
<213> ORGANISM: Artificial Sequence
<220> FEATURE:
<223> OTHER INFORMATION: FOSB forward primer

<400> SEQUENCE: 47
gccactgccg accacaattc                                             20

<210> SEQ ID NO 48
<211> LENGTH: 22
<212> TYPE: DNA
<213> ORGANISM: Artificial Sequence
<220> FEATURE:
<223> OTHER INFORMATION: FOSB reverse primer

<400> SEQUENCE: 48
ttattggcga cagtgcagaa cc                                          22

<210> SEQ ID NO 49
<211> LENGTH: 19
<212> TYPE: DNA
<213> ORGANISM: Artificial Sequence
<220> FEATURE:

<223> OTHER INFORMATION: FRA2 forward primer

<400> SEQUENCE: 49
agcctcccga agaggacag    19

<210> SEQ ID NO 50
<211> LENGTH: 20
<212> TYPE: DNA
<213> ORGANISM: Artificial Sequence
<220> FEATURE:
<223> OTHER INFORMATION: FRA2 reverse primer

<400> SEQUENCE: 50
aggacattgg ggtaggtgaa    20

<210> SEQ ID NO 51
<211> LENGTH: 22
<212> TYPE: DNA
<213> ORGANISM: Artificial Sequence
<220> FEATURE:
<223> OTHER INFORMATION: GDF3 forward primer

<400> SEQUENCE: 51
taaggtgggc agattgcttt tt    22

<210> SEQ ID NO 52
<211> LENGTH: 21
<212> TYPE: DNA
<213> ORGANISM: Artificial Sequence
<220> FEATURE:
<223> OTHER INFORMATION: GDF3 reverse primer

<400> SEQUENCE: 52
ctggacagtt accctggagt a    21

<210> SEQ ID NO 53
<211> LENGTH: 22
<212> TYPE: DNA
<213> ORGANISM: Artificial Sequence
<220> FEATURE:
<223> OTHER INFORMATION: GLI1 forward primer

<400> SEQUENCE: 53
gagcccttct ttaggattcc ca    22

<210> SEQ ID NO 54
<211> LENGTH: 21
<212> TYPE: DNA
<213> ORGANISM: Artificial Sequence
<220> FEATURE:
<223> OTHER INFORMATION: GLI1 reverse primer

<400> SEQUENCE: 54
accccgagta gagtcatgtg g    21

<210> SEQ ID NO 55
<211> LENGTH: 22
<212> TYPE: DNA
<213> ORGANISM: Artificial Sequence
<220> FEATURE:
<223> OTHER INFORMATION: GM-CSF forward primer

<400> SEQUENCE: 55
tcgtctctaa cgagttctcc tt    22

```
<210> SEQ ID NO 56
<211> LENGTH: 23
<212> TYPE: DNA
<213> ORGANISM: Artificial Sequence
<220> FEATURE:
<223> OTHER INFORMATION: GM-CSF reverse primer

<400> SEQUENCE: 56
gcagtatgtc tggtagtagc tgg                                            23

<210> SEQ ID NO 57
<211> LENGTH: 19
<212> TYPE: DNA
<213> ORGANISM: Artificial Sequence
<220> FEATURE:
<223> OTHER INFORMATION: HGF forward primer

<400> SEQUENCE: 57
ctgcttcatg tcgccatcc                                                 19

<210> SEQ ID NO 58
<211> LENGTH: 23
<212> TYPE: DNA
<213> ORGANISM: Artificial Sequence
<220> FEATURE:
<223> OTHER INFORMATION: HGF reverse primer

<400> SEQUENCE: 58
tgggtcttcc ttggtaagag tag                                            23

<210> SEQ ID NO 59
<211> LENGTH: 22
<212> TYPE: DNA
<213> ORGANISM: Artificial Sequence
<220> FEATURE:
<223> OTHER INFORMATION: HIF1alpha forward primer

<400> SEQUENCE: 59
ggtcatcgca gttggaacct cc                                             22

<210> SEQ ID NO 60
<211> LENGTH: 22
<212> TYPE: DNA
<213> ORGANISM: Artificial Sequence
<220> FEATURE:
<223> OTHER INFORMATION: HIF1alpha reverse primer

<400> SEQUENCE: 60
cgcttgtgtc ttggaaggct tg                                             22

<210> SEQ ID NO 61
<211> LENGTH: 20
<212> TYPE: DNA
<213> ORGANISM: Artificial Sequence
<220> FEATURE:
<223> OTHER INFORMATION: IAP2 forward primer

<400> SEQUENCE: 61
agggaccatc aagggcacag                                                20

<210> SEQ ID NO 62
<211> LENGTH: 22
<212> TYPE: DNA
<213> ORGANISM: Artificial Sequence
<220> FEATURE:
<223> OTHER INFORMATION: IAP2 reverse primer
```

```
<400> SEQUENCE: 62
tttgtgtgtt tggcggtgtc tc                                          22

<210> SEQ ID NO 63
<211> LENGTH: 20
<212> TYPE: DNA
<213> ORGANISM: Artificial Sequence
<220> FEATURE:
<223> OTHER INFORMATION: IGFBP4 forward primer

<400> SEQUENCE: 63
agaagcccct gcgtacattg                                             20

<210> SEQ ID NO 64
<211> LENGTH: 21
<212> TYPE: DNA
<213> ORGANISM: Artificial Sequence
<220> FEATURE:
<223> OTHER INFORMATION: IGFBP4 reverse primer

<400> SEQUENCE: 64
tgtccccacg atcttcatct t                                           21

<210> SEQ ID NO 65
<211> LENGTH: 19
<212> TYPE: DNA
<213> ORGANISM: Artificial Sequence
<220> FEATURE:
<223> OTHER INFORMATION: IL1R1 forward primer

<400> SEQUENCE: 65
gccaaggtgg aggactcag                                              19

<210> SEQ ID NO 66
<211> LENGTH: 23
<212> TYPE: DNA
<213> ORGANISM: Artificial Sequence
<220> FEATURE:
<223> OTHER INFORMATION: IL1R1 reverse primer

<400> SEQUENCE: 66
ccagggtcat tctctaacac agt                                         23

<210> SEQ ID NO 67
<211> LENGTH: 23
<212> TYPE: DNA
<213> ORGANISM: Artificial Sequence
<220> FEATURE:
<223> OTHER INFORMATION: IL-6 forward primer

<400> SEQUENCE: 67
tagtccttcc tacccccaatt tcc                                        23

<210> SEQ ID NO 68
<211> LENGTH: 21
<212> TYPE: DNA
<213> ORGANISM: Artificial Sequence
<220> FEATURE:
<223> OTHER INFORMATION: IL-6 reverse primer

<400> SEQUENCE: 68
ttggtcctta gccactcctt c                                           21

<210> SEQ ID NO 69
<211> LENGTH: 21
```

```
<212> TYPE: DNA
<213> ORGANISM: Artificial Sequence
<220> FEATURE:
<223> OTHER INFORMATION: IL-10 forward primer

<400> SEQUENCE: 69
agaagcatgg cccagaaatc a                                           21

<210> SEQ ID NO 70
<211> LENGTH: 20
<212> TYPE: DNA
<213> ORGANISM: Artificial Sequence
<220> FEATURE:
<223> OTHER INFORMATION: IL-10 reverse primer

<400> SEQUENCE: 70
ggccttgtag acaccttggt                                             20

<210> SEQ ID NO 71
<211> LENGTH: 20
<212> TYPE: DNA
<213> ORGANISM: Artificial Sequence
<220> FEATURE:
<223> OTHER INFORMATION: IL-8 forward primer

<400> SEQUENCE: 71
gtgaacccca gaccagactg                                             20

<210> SEQ ID NO 72
<211> LENGTH: 22
<212> TYPE: DNA
<213> ORGANISM: Artificial Sequence
<220> FEATURE:
<223> OTHER INFORMATION: IL-8 reverse primer

<400> SEQUENCE: 72
cctggaacac gtttctgaaa ga                                          22

<210> SEQ ID NO 73
<211> LENGTH: 21
<212> TYPE: DNA
<213> ORGANISM: Artificial Sequence
<220> FEATURE:
<223> OTHER INFORMATION: INHBA forward primer

<400> SEQUENCE: 73
atagaggacg acattggcag g                                           21

<210> SEQ ID NO 74
<211> LENGTH: 21
<212> TYPE: DNA
<213> ORGANISM: Artificial Sequence
<220> FEATURE:
<223> OTHER INFORMATION: INHBA reverse primer

<400> SEQUENCE: 74
atagaggacg acattggcag g                                           21

<210> SEQ ID NO 75
<211> LENGTH: 21
<212> TYPE: DNA
<213> ORGANISM: Artificial Sequence
<220> FEATURE:
<223> OTHER INFORMATION: ITGAV forward primer

<400> SEQUENCE: 75
```

```
cctgtgctcc attgtaccac t                                               21

<210> SEQ ID NO 76
<211> LENGTH: 22
<212> TYPE: DNA
<213> ORGANISM: Artificial Sequence
<220> FEATURE:
<223> OTHER INFORMATION: ITGAV reverse primer

<400> SEQUENCE: 76
agcatactca acggtctttg tg                                              22

<210> SEQ ID NO 77
<211> LENGTH: 21
<212> TYPE: DNA
<213> ORGANISM: Artificial Sequence
<220> FEATURE:
<223> OTHER INFORMATION: JUN-B forward primer

<400> SEQUENCE: 77
gacctgcaca agatgaacca c                                               21

<210> SEQ ID NO 78
<211> LENGTH: 21
<212> TYPE: DNA
<213> ORGANISM: Artificial Sequence
<220> FEATURE:
<223> OTHER INFORMATION: JUN-B reverse primer

<400> SEQUENCE: 78
aggctggaga gtaactgctg a                                               21

<210> SEQ ID NO 79
<211> LENGTH: 20
<212> TYPE: DNA
<213> ORGANISM: Artificial Sequence
<220> FEATURE:
<223> OTHER INFORMATION: KGF forward primer

<400> SEQUENCE: 79
ccgtggcagt tggaattgtg                                                 20

<210> SEQ ID NO 80
<211> LENGTH: 20
<212> TYPE: DNA
<213> ORGANISM: Artificial Sequence
<220> FEATURE:
<223> OTHER INFORMATION: KGF reverse primer

<400> SEQUENCE: 80
cctccgctgt gtgtccattt                                                 20

<210> SEQ ID NO 81
<211> LENGTH: 21
<212> TYPE: DNA
<213> ORGANISM: Artificial Sequence
<220> FEATURE:
<223> OTHER INFORMATION: KI67 forward primer

<400> SEQUENCE: 81
ctgcctcaga tggctcaaag a                                               21

<210> SEQ ID NO 82
<211> LENGTH: 22
<212> TYPE: DNA
<213> ORGANISM: Artificial Sequence
```

-continued

```
<220> FEATURE:
<223> OTHER INFORMATION: KI67 reverse primer

<400> SEQUENCE: 82
gaagacttcg gttccctgta ac                                              22

<210> SEQ ID NO 83
<211> LENGTH: 19
<212> TYPE: DNA
<213> ORGANISM: Artificial Sequence
<220> FEATURE:
<223> OTHER INFORMATION: KLF9 forward primer

<400> SEQUENCE: 83
gccgcctaca tggacttcg                                                  19

<210> SEQ ID NO 84
<211> LENGTH: 19
<212> TYPE: DNA
<213> ORGANISM: Artificial Sequence
<220> FEATURE:
<223> OTHER INFORMATION: KLF9 reverse primer

<400> SEQUENCE: 84
gccgttcacc tgtatgcac                                                  19

<210> SEQ ID NO 85
<211> LENGTH: 23
<212> TYPE: DNA
<213> ORGANISM: Artificial Sequence
<220> FEATURE:
<223> OTHER INFORMATION: MAPK3 forward primer

<400> SEQUENCE: 85
accacattct aggtatcttg ggt                                             23

<210> SEQ ID NO 86
<211> LENGTH: 21
<212> TYPE: DNA
<213> ORGANISM: Artificial Sequence
<220> FEATURE:
<223> OTHER INFORMATION: MAPK3 reverse primer

<400> SEQUENCE: 86
gatgcgcttg tttggttga a                                                21

<210> SEQ ID NO 87
<211> LENGTH: 20
<212> TYPE: DNA
<213> ORGANISM: Artificial Sequence
<220> FEATURE:
<223> OTHER INFORMATION: MAP4K1 forward primer

<400> SEQUENCE: 87
ctcacagctc gctcagatcc                                                 20

<210> SEQ ID NO 88
<211> LENGTH: 19
<212> TYPE: DNA
<213> ORGANISM: Artificial Sequence
<220> FEATURE:
<223> OTHER INFORMATION: MAP4K1 reverse primer

<400> SEQUENCE: 88
gaggggacag ccgttgaat                                                  19
```

<210> SEQ ID NO 89
<211> LENGTH: 23
<212> TYPE: DNA
<213> ORGANISM: Artificial Sequence
<220> FEATURE:
<223> OTHER INFORMATION: MLANA forward primer

<400> SEQUENCE: 89
tggatacaga accttgatgg aca                                            23

<210> SEQ ID NO 90
<211> LENGTH: 21
<212> TYPE: DNA
<213> ORGANISM: Artificial Sequence
<220> FEATURE:
<223> OTHER INFORMATION: MLANA reverse primer

<400> SEQUENCE: 90
gggctgatgg gatttctctt g                                              21

<210> SEQ ID NO 91
<211> LENGTH: 22
<212> TYPE: DNA
<213> ORGANISM: Artificial Sequence
<220> FEATURE:
<223> OTHER INFORMATION: MMP9 forward primer

<400> SEQUENCE: 91
aaaccacctc tcccgactcc ag                                             22

<210> SEQ ID NO 92
<211> LENGTH: 22
<212> TYPE: DNA
<213> ORGANISM: Artificial Sequence
<220> FEATURE:
<223> OTHER INFORMATION: MMP9 reverse primer

<400> SEQUENCE: 92
agctcggtgg tgttctccaa tg                                             22

<210> SEQ ID NO 93
<211> LENGTH: 20
<212> TYPE: DNA
<213> ORGANISM: Artificial Sequence
<220> FEATURE:
<223> OTHER INFORMATION: MMP13 forward primer

<400> SEQUENCE: 93
acctccacag ttgacaggct                                                20

<210> SEQ ID NO 94
<211> LENGTH: 21
<212> TYPE: DNA
<213> ORGANISM: Artificial Sequence
<220> FEATURE:
<223> OTHER INFORMATION: MMP13 reverse primer

<400> SEQUENCE: 94
aggcactcca catcttggtt t                                              21

<210> SEQ ID NO 95
<211> LENGTH: 22
<212> TYPE: DNA
<213> ORGANISM: Artificial Sequence
<220> FEATURE:
<223> OTHER INFORMATION: OPN forward primer

```
<400> SEQUENCE: 95
atctcaccat tcggatgagt ct                                          22

<210> SEQ ID NO 96
<211> LENGTH: 23
<212> TYPE: DNA
<213> ORGANISM: Artificial Sequence
<220> FEATURE:
<223> OTHER INFORMATION: OPN reverse primer

<400> SEQUENCE: 96
tcagtccata agccaagcta tca                                         23

<210> SEQ ID NO 97
<211> LENGTH: 22
<212> TYPE: DNA
<213> ORGANISM: Artificial Sequence
<220> FEATURE:
<223> OTHER INFORMATION: PAI1 forward primer

<400> SEQUENCE: 97
gtgcatcact ccacaaacct gc                                          22

<210> SEQ ID NO 98
<211> LENGTH: 21
<212> TYPE: DNA
<213> ORGANISM: Artificial Sequence
<220> FEATURE:
<223> OTHER INFORMATION: PAI1 reverse primer

<400> SEQUENCE: 98
taacgtgggt tgccaagcat c                                           21

<210> SEQ ID NO 99
<211> LENGTH: 19
<212> TYPE: DNA
<213> ORGANISM: Artificial Sequence
<220> FEATURE:
<223> OTHER INFORMATION: PDGFA forward primer

<400> SEQUENCE: 99
cgctgcactg gctgttgta                                              19

<210> SEQ ID NO 100
<211> LENGTH: 21
<212> TYPE: DNA
<213> ORGANISM: Artificial Sequence
<220> FEATURE:
<223> OTHER INFORMATION: PDGFA reverse primer

<400> SEQUENCE: 100
ttccctacgc cttcctgtct c                                           21

<210> SEQ ID NO 101
<211> LENGTH: 19
<212> TYPE: DNA
<213> ORGANISM: Artificial Sequence
<220> FEATURE:
<223> OTHER INFORMATION: PDGFB forward primer

<400> SEQUENCE: 101
cgagccaaga cgcctcaag                                              19

<210> SEQ ID NO 102
```

```
<211> LENGTH: 22
<212> TYPE: DNA
<213> ORGANISM: Artificial Sequence
<220> FEATURE:
<223> OTHER INFORMATION: PDGFB reverse primer

<400> SEQUENCE: 102
catgggtgtg cttaaacttt cg                                              22

<210> SEQ ID NO 103
<211> LENGTH: 21
<212> TYPE: DNA
<213> ORGANISM: Artificial Sequence
<220> FEATURE:
<223> OTHER INFORMATION: PECAM1 forward primer

<400> SEQUENCE: 103
tgcaccccat cacttaccac c                                               21

<210> SEQ ID NO 104
<211> LENGTH: 21
<212> TYPE: DNA
<213> ORGANISM: Artificial Sequence
<220> FEATURE:
<223> OTHER INFORMATION: PECAM1 reverse primer

<400> SEQUENCE: 104
taaaacgcgg tcctgttcct c                                               21

<210> SEQ ID NO 105
<211> LENGTH: 19
<212> TYPE: DNA
<213> ORGANISM: Artificial Sequence
<220> FEATURE:
<223> OTHER INFORMATION: PPARalpha forward primer

<400> SEQUENCE: 105
tcggcgaact attcggctg                                                  19

<210> SEQ ID NO 106
<211> LENGTH: 20
<212> TYPE: DNA
<213> ORGANISM: Artificial Sequence
<220> FEATURE:
<223> OTHER INFORMATION: PPARalpha reverse primer

<400> SEQUENCE: 106
gcacttgtga aaacggcagt                                                 20

<210> SEQ ID NO 107
<211> LENGTH: 21
<212> TYPE: DNA
<213> ORGANISM: Artificial Sequence
<220> FEATURE:
<223> OTHER INFORMATION: PPARbeta forward primer

<400> SEQUENCE: 107
ttgagcccaa gttcgagttt g                                               21

<210> SEQ ID NO 108
<211> LENGTH: 21
<212> TYPE: DNA
<213> ORGANISM: Artificial Sequence
<220> FEATURE:
<223> OTHER INFORMATION: PPARbeta reverse primer

<400> SEQUENCE: 108
```

```
cggtctccac acagaatgat g                                              21

<210> SEQ ID NO 109
<211> LENGTH: 21
<212> TYPE: DNA
<213> ORGANISM: Artificial Sequence
<220> FEATURE:
<223> OTHER INFORMATION: PPARgamma forward primer

<400> SEQUENCE: 109
tgtggggata aagcatcagg c                                              21

<210> SEQ ID NO 110
<211> LENGTH: 23
<212> TYPE: DNA
<213> ORGANISM: Artificial Sequence
<220> FEATURE:
<223> OTHER INFORMATION: PPARgamma reverse primer

<400> SEQUENCE: 110
ccggcagtta agatcacacc tat                                            23

<210> SEQ ID NO 111
<211> LENGTH: 21
<212> TYPE: DNA
<213> ORGANISM: Artificial Sequence
<220> FEATURE:
<223> OTHER INFORMATION: RHOA forward primer

<400> SEQUENCE: 111
agcctttctc acctggactg c                                              21

<210> SEQ ID NO 112
<211> LENGTH: 20
<212> TYPE: DNA
<213> ORGANISM: Artificial Sequence
<220> FEATURE:
<223> OTHER INFORMATION: RHOA reverse primer

<400> SEQUENCE: 112
cacccactgc cacccataag                                                20

<210> SEQ ID NO 113
<211> LENGTH: 25
<212> TYPE: DNA
<213> ORGANISM: Artificial Sequence
<220> FEATURE:
<223> OTHER INFORMATION: Rpl27 forward primer

<400> SEQUENCE: 113
caaggggata tccacagagt acctt                                          25

<210> SEQ ID NO 114
<211> LENGTH: 23
<212> TYPE: DNA
<213> ORGANISM: Artificial Sequence
<220> FEATURE:
<223> OTHER INFORMATION: Rpl27 reverse primer

<400> SEQUENCE: 114
ctggtggctg gaattgaccg cta                                            23

<210> SEQ ID NO 115
<211> LENGTH: 21
<212> TYPE: DNA
```

```
<213> ORGANISM: Artificial Sequence
<220> FEATURE:
<223> OTHER INFORMATION: SKIL forward primer

<400> SEQUENCE: 115
aggcagagac aagtaagtcc a                                             21

<210> SEQ ID NO 116
<211> LENGTH: 23
<212> TYPE: DNA
<213> ORGANISM: Artificial Sequence
<220> FEATURE:
<223> OTHER INFORMATION: SKIL reverse primer

<400> SEQUENCE: 116
cgtctgggta agacactgtt ttt                                           23

<210> SEQ ID NO 117
<211> LENGTH: 20
<212> TYPE: DNA
<213> ORGANISM: Artificial Sequence
<220> FEATURE:
<223> OTHER INFORMATION: SMAD3 forward primer

<400> SEQUENCE: 117
cccccactgg atgactacag                                               20

<210> SEQ ID NO 118
<211> LENGTH: 21
<212> TYPE: DNA
<213> ORGANISM: Artificial Sequence
<220> FEATURE:
<223> OTHER INFORMATION: SMAD3 reverse primer

<400> SEQUENCE: 118
tccatcttca ctcaggtagc c                                             21

<210> SEQ ID NO 119
<211> LENGTH: 20
<212> TYPE: DNA
<213> ORGANISM: Artificial Sequence
<220> FEATURE:
<223> OTHER INFORMATION: SOCS1 forward primer

<400> SEQUENCE: 119
ctgcggcttc tattggggac                                               20

<210> SEQ ID NO 120
<211> LENGTH: 21
<212> TYPE: DNA
<213> ORGANISM: Artificial Sequence
<220> FEATURE:
<223> OTHER INFORMATION: SOCS1 reverse primer

<400> SEQUENCE: 120
aaaaggcagt cgaaggtctc g                                             21

<210> SEQ ID NO 121
<211> LENGTH: 21
<212> TYPE: DNA
<213> ORGANISM: Artificial Sequence
<220> FEATURE:
<223> OTHER INFORMATION: SOCS3 forward primer

<400> SEQUENCE: 121
caagaaccta cgcatccagt g                                             21
```

<210> SEQ ID NO 122
<211> LENGTH: 22
<212> TYPE: DNA
<213> ORGANISM: Artificial Sequence
<220> FEATURE:
<223> OTHER INFORMATION: SOCS3 reverse primer

<400> SEQUENCE: 122
ccagcttgag tacacagtcg aa                                              22

<210> SEQ ID NO 123
<211> LENGTH: 23
<212> TYPE: DNA
<213> ORGANISM: Artificial Sequence
<220> FEATURE:
<223> OTHER INFORMATION: SPARC forward primer

<400> SEQUENCE: 123
actacatcgg accatgcaaa tac                                             23

<210> SEQ ID NO 124
<211> LENGTH: 23
<212> TYPE: DNA
<213> ORGANISM: Artificial Sequence
<220> FEATURE:
<223> OTHER INFORMATION: SPARC reverse primer

<400> SEQUENCE: 124
gtacaaggtg accaggacat ttt                                             23

<210> SEQ ID NO 125
<211> LENGTH: 20
<212> TYPE: DNA
<213> ORGANISM: Artificial Sequence
<220> FEATURE:
<223> OTHER INFORMATION: STAT1 forward primer

<400> SEQUENCE: 125
ggagcacgct gcctatgatg                                                 20

<210> SEQ ID NO 126
<211> LENGTH: 21
<212> TYPE: DNA
<213> ORGANISM: Artificial Sequence
<220> FEATURE:
<223> OTHER INFORMATION: STAT1 reverse primer

<400> SEQUENCE: 126
ctccagagaa aagcggctgt a                                               21

<210> SEQ ID NO 127
<211> LENGTH: 21
<212> TYPE: DNA
<213> ORGANISM: Artificial Sequence
<220> FEATURE:
<223> OTHER INFORMATION: STAT3 forward primer

<400> SEQUENCE: 127
caataccatt gacctgccga t                                               21

<210> SEQ ID NO 128
<211> LENGTH: 19
<212> TYPE: DNA
<213> ORGANISM: Artificial Sequence
<220> FEATURE:

<223> OTHER INFORMATION: STAT3 reverse primer

<400> SEQUENCE: 128
gagcgactca aactgccct                                                    19

<210> SEQ ID NO 129
<211> LENGTH: 19
<212> TYPE: DNA
<213> ORGANISM: Artificial Sequence
<220> FEATURE:
<223> OTHER INFORMATION: STAT5A forward primer

<400> SEQUENCE: 129
agtggttcga cggggtgat                                                    19

<210> SEQ ID NO 130
<211> LENGTH: 21
<212> TYPE: DNA
<213> ORGANISM: Artificial Sequence
<220> FEATURE:
<223> OTHER INFORMATION: STAT5A reverse primer

<400> SEQUENCE: 130
atggcttcag attccagagg t                                                 21

<210> SEQ ID NO 131
<211> LENGTH: 19
<212> TYPE: DNA
<213> ORGANISM: Artificial Sequence
<220> FEATURE:
<223> OTHER INFORMATION: TGFalpha forward primer

<400> SEQUENCE: 131
cactctgggt acgtgggtg                                                    19

<210> SEQ ID NO 132
<211> LENGTH: 22
<212> TYPE: DNA
<213> ORGANISM: Artificial Sequence
<220> FEATURE:
<223> OTHER INFORMATION: TGFalpha reverse primer

<400> SEQUENCE: 132
cacaggtgat aatgaggaca gc                                                22

<210> SEQ ID NO 133
<211> LENGTH: 20
<212> TYPE: DNA
<213> ORGANISM: Artificial Sequence
<220> FEATURE:
<223> OTHER INFORMATION: TGFbeta1 forward primer

<400> SEQUENCE: 133
ccgcaacaac gccatctatg                                                   20

<210> SEQ ID NO 134
<211> LENGTH: 19
<212> TYPE: DNA
<213> ORGANISM: Artificial Sequence
<220> FEATURE:
<223> OTHER INFORMATION: TGFbeta1 reverse primer

<400> SEQUENCE: 134
ctctgcacgg gacagcaat                                                    19

```
<210> SEQ ID NO 135
<211> LENGTH: 22
<212> TYPE: DNA
<213> ORGANISM: Artificial Sequence
<220> FEATURE:
<223> OTHER INFORMATION: TGFbeta2 forward primer

<400> SEQUENCE: 135
tcgacatgga tcagtttatg cg                                                  22

<210> SEQ ID NO 136
<211> LENGTH: 22
<212> TYPE: DNA
<213> ORGANISM: Artificial Sequence
<220> FEATURE:
<223> OTHER INFORMATION: TGFbeta2 reverse primer

<400> SEQUENCE: 136
ccctggtact gttgtagatg ga                                                  22

<210> SEQ ID NO 137
<211> LENGTH: 23
<212> TYPE: DNA
<213> ORGANISM: Artificial Sequence
<220> FEATURE:
<223> OTHER INFORMATION: TGFbetaR1 forward primer

<400> SEQUENCE: 137
tcccaactac aggaccttt tca                                                  23

<210> SEQ ID NO 138
<211> LENGTH: 22
<212> TYPE: DNA
<213> ORGANISM: Artificial Sequence
<220> FEATURE:
<223> OTHER INFORMATION: TGFbetaR1 reverse primer

<400> SEQUENCE: 138
gcagtggtaa acctgatcca ga                                                  22

<210> SEQ ID NO 139
<211> LENGTH: 20
<212> TYPE: DNA
<213> ORGANISM: Artificial Sequence
<220> FEATURE:
<223> OTHER INFORMATION: TIMP1 forward primer

<400> SEQUENCE: 139
cttggttccc tggcgtactc                                                     20

<210> SEQ ID NO 140
<211> LENGTH: 21
<212> TYPE: DNA
<213> ORGANISM: Artificial Sequence
<220> FEATURE:
<223> OTHER INFORMATION: TIMP1 reverse primer

<400> SEQUENCE: 140
acctgatccg tccacaaaca g                                                   21

<210> SEQ ID NO 141
<211> LENGTH: 21
<212> TYPE: DNA
<213> ORGANISM: Artificial Sequence
<220> FEATURE:
<223> OTHER INFORMATION: TIMP2 forward primer
```

```
<400> SEQUENCE: 141
ctggacgttg gaggaaagaa g                                              21

<210> SEQ ID NO 142
<211> LENGTH: 20
<212> TYPE: DNA
<213> ORGANISM: Artificial Sequence
<220> FEATURE:
<223> OTHER INFORMATION: TIMP2 reverse primer

<400> SEQUENCE: 142
ggtgatgcta agcgtgtccc                                                20

<210> SEQ ID NO 143
<211> LENGTH: 19
<212> TYPE: DNA
<213> ORGANISM: Artificial Sequence
<220> FEATURE:
<223> OTHER INFORMATION: TIMP3 forward primer

<400> SEQUENCE: 143
gcgcaagggc ctcaattac                                                 19

<210> SEQ ID NO 144
<211> LENGTH: 22
<212> TYPE: DNA
<213> ORGANISM: Artificial Sequence
<220> FEATURE:
<223> OTHER INFORMATION: TIMP3 reverse primer

<400> SEQUENCE: 144
agagacactc attcttggag gt                                             22

<210> SEQ ID NO 145
<211> LENGTH: 21
<212> TYPE: DNA
<213> ORGANISM: Artificial Sequence
<220> FEATURE:
<223> OTHER INFORMATION: TLR2 forward primer

<400> SEQUENCE: 145
ccagacactg ggggtaacat c                                              21

<210> SEQ ID NO 146
<211> LENGTH: 22
<212> TYPE: DNA
<213> ORGANISM: Artificial Sequence
<220> FEATURE:
<223> OTHER INFORMATION: TLR2 reverse primer

<400> SEQUENCE: 146
cggatcgact ttagactttg gg                                             22

<210> SEQ ID NO 147
<211> LENGTH: 21
<212> TYPE: DNA
<213> ORGANISM: Artificial Sequence
<220> FEATURE:
<223> OTHER INFORMATION: TLR4 forward primer

<400> SEQUENCE: 147
aaagtggccc taccaagtct c                                              21

<210> SEQ ID NO 148
<211> LENGTH: 22
```

```
<212> TYPE: DNA
<213> ORGANISM: Artificial Sequence
<220> FEATURE:
<223> OTHER INFORMATION: TLR4 reverse primer

<400> SEQUENCE: 148
tcaggctgtt tgttcccaaa tc                                           22

<210> SEQ ID NO 149
<211> LENGTH: 19
<212> TYPE: DNA
<213> ORGANISM: Artificial Sequence
<220> FEATURE:
<223> OTHER INFORMATION: TNC forward primer

<400> SEQUENCE: 149
gctaccgacg ggatcttcg                                               19

<210> SEQ ID NO 150
<211> LENGTH: 21
<212> TYPE: DNA
<213> ORGANISM: Artificial Sequence
<220> FEATURE:
<223> OTHER INFORMATION: TNC reverse primer

<400> SEQUENCE: 150
tagccgtggt actgatggtt t                                            21

<210> SEQ ID NO 151
<211> LENGTH: 21
<212> TYPE: DNA
<213> ORGANISM: Artificial Sequence
<220> FEATURE:
<223> OTHER INFORMATION: TNFalpha forward primer

<400> SEQUENCE: 151
ggctttccga attcactgga g                                            21

<210> SEQ ID NO 152
<211> LENGTH: 19
<212> TYPE: DNA
<213> ORGANISM: Artificial Sequence
<220> FEATURE:
<223> OTHER INFORMATION: TNFalpha reverse primer

<400> SEQUENCE: 152
ccccggcctt ccaaataaa                                               19

<210> SEQ ID NO 153
<211> LENGTH: 22
<212> TYPE: DNA
<213> ORGANISM: Artificial Sequence
<220> FEATURE:
<223> OTHER INFORMATION: TNFalphaIP2 forward primer

<400> SEQUENCE: 153
aaagggatac ctacttgctg ct                                           22

<210> SEQ ID NO 154
<211> LENGTH: 19
<212> TYPE: DNA
<213> ORGANISM: Artificial Sequence
<220> FEATURE:
<223> OTHER INFORMATION: TNFalphaIP reverse primer

<400> SEQUENCE: 154
```

```
caagcccgac accttgaag                                              19

<210> SEQ ID NO 155
<211> LENGTH: 21
<212> TYPE: DNA
<213> ORGANISM: Artificial Sequence
<220> FEATURE:
<223> OTHER INFORMATION: TSP-1 forward primer

<400> SEQUENCE: 155
gaagcaacaa gtggtgtcag t                                           21

<210> SEQ ID NO 156
<211> LENGTH: 23
<212> TYPE: DNA
<213> ORGANISM: Artificial Sequence
<220> FEATURE:
<223> OTHER INFORMATION: TSP-1 reverse primer

<400> SEQUENCE: 156
acagtctatg tagagttgag ccc                                         23

<210> SEQ ID NO 157
<211> LENGTH: 23
<212> TYPE: DNA
<213> ORGANISM: Artificial Sequence
<220> FEATURE:
<223> OTHER INFORMATION: VEGFA forward primer

<400> SEQUENCE: 157
gcacatagag agaatgagct tcc                                         23

<210> SEQ ID NO 158
<211> LENGTH: 19
<212> TYPE: DNA
<213> ORGANISM: Artificial Sequence
<220> FEATURE:
<223> OTHER INFORMATION: VEGFA reverse primer

<400> SEQUENCE: 158
ctccgctctg aacaaggct                                              19

<210> SEQ ID NO 159
<211> LENGTH: 21
<212> TYPE: DNA
<213> ORGANISM: Artificial Sequence
<220> FEATURE:
<223> OTHER INFORMATION: VGR forward primer

<400> SEQUENCE: 159
tccttgaacc gcaagagtct c                                           21

<210> SEQ ID NO 160
<211> LENGTH: 20
<212> TYPE: DNA
<213> ORGANISM: Artificial Sequence
<220> FEATURE:
<223> OTHER INFORMATION: VGR reverse primer

<400> SEQUENCE: 160
ctcaccctca ggaatctggg                                             20

<210> SEQ ID NO 161
<211> LENGTH: 19
<212> TYPE: DNA
<213> ORGANISM: Artificial Sequence
```

```
<220> FEATURE:
<223> OTHER INFORMATION: VHL forward primer

<400> SEQUENCE: 161
aaagagcggt gccttcagg                                                    19

<210> SEQ ID NO 162
<211> LENGTH: 22
<212> TYPE: DNA
<213> ORGANISM: Artificial Sequence
<220> FEATURE:
<223> OTHER INFORMATION: VHL reverse primer

<400> SEQUENCE: 162
cacttgggta gtcctccaaa tc                                                22

<210> SEQ ID NO 163
<211> LENGTH: 23
<212> TYPE: DNA
<213> ORGANISM: Artificial Sequence
<220> FEATURE:
<223> OTHER INFORMATION: XRCC1 forward primer

<400> SEQUENCE: 163
tcttcagtcg tatcaacaag acg                                               23

<210> SEQ ID NO 164
<211> LENGTH: 20
<212> TYPE: DNA
<213> ORGANISM: Artificial Sequence
<220> FEATURE:
<223> OTHER INFORMATION: XRCC1 reverse primer

<400> SEQUENCE: 164
gtttgctggg aggtttcctg                                                   20
```

ANGIOPOIETIN-LIKE 4 AND A METHOD OF ITS USE IN WOUND HEALING

CROSS-REFERENCE TO RELATED APPLICATION

This application claims the benefit of priority of U.S. of America Provisional Patent Application No. 61/673,463 filed Jul. 19, 2012, the contents of which being hereby incorporated by reference in its entirety for all purposes.

STATEMENT REGARDING SEQUENCE LISTING

The Sequence Listing associated with this application is provided in text format in lieu of a paper copy, and is hereby incorporated by reference into the specification. The name of the text file containing the Sequence Listing is 690148_473USPC_SEQUENCE_LISTING.txt. The text file is 33.1 KB, was created on Jan. 14, 2015, and is being submitted electronically via EFS-Web.

FIELD

The invention relates to compositions for use in wound healing and methods of wound healing treatment.

BACKGROUND

Type II diabetes is a medical menace that affects ~200 million people and continues to be an increasing burden on healthcare resources worldwide with its morbidities of retinopathy, cardiovascular diseases and diabetic nephropathy [1]. Impaired wound repair represents one of the most significant unmet medical needs in the world today and is a major complication of diabetes, resulting in significant morbidity, lost productivity, and healthcare expenditures [2]. Furthermore, poor healing diabetic wound is an open portal for infections, often resulting in chronic inflammation, sepsis, dehiscence and death. Despite the enormous impact these chronic wounds have, effective therapies have been lacking. To effectively manage these problems one must understand the healing process and to create a salubrious physical and biochemical environment conducive for healing.

Normal wound healing proceeds via a continuum of events that includes the acute inflammatory, proliferative and maturation phases [3,4]. These events entail a complex interplay between connective tissue formation, cellular activity, and growth factor activation. All three of these physiologic processes is altered in the diabetic state [5,6]. Extracellular matrix (ECM) components are integral to each phase of wound healing, interacting with cells and growth factors in a dynamic reciprocal manner that eventually results in wound closure.

Chronic wounds, such as venous, diabetic or pressure ulcers, represent one of the most significant unmet medical needs in the world today and are a major complication of diabetes, resulting in significant morbidity, lost productivity, and healthcare expenditures. Diabetic foot ulceration is a significant cause of morbidity and is the most common reason for hospital admission in diabetic patients. Approximately 15% of diabetic patients will develop chronic ulcers during their lifetimes. In those who require lower-limb amputation, 70-90% will be preceded by foot ulceration[2].

Diabetic wounds are characterized by an accumulation of devitalized tissue, increased/prolonged inflammation, poor wound-related angiogenesis and deficiencies in the ECM components [6,7]. Diabetic wounds show elevated levels of matrix metalloproteinases (MMPs), increased proteolytic degradation of ECM components, inactivation of growth factors that culminate in a corrupt ECM that cannot support healing [5,8]. Abnormal nitric oxide (NO) production also contributes to the pathogenesis of impaired healing. Cells such as keratinocytes, fibroblasts and macrophages display both dysfunctional expression and responses to many growth factors and cytokines. Thus, these wounds typically are non-responsive to most treatments. For these reasons, it may be most advantageous to intervene with aggressive strategies that could restore corrupt extracellular microenvironment in a diabetic wound. Wound healing strategies that replace the missing or dysfunctional ECM components may be beneficial. Ideally, such replacement should be multifaceted and interactive in nature, and closely approximate the components of normal ECM. In this aspect, the role of matricellular proteins in wound healing is of interest. Matricellular proteins can associate with the diverse protein in extracellular matrix reservoir and bridged them with their cognate cell surface receptors [9-11]. They are expressed temporally and spatially during wound healing and resided at the crossroads of cell-matrix communication serving as a modulator for several regulatory networks. Presumably, the regulatory pathways consist of complex networks making it difficult to design for compensatory adjustments required for wound repair. It may be most advantageous to intervene with aggressive healing strategies that replace the missing or dysfunctional extracellular matrix (ECM) components. Ideally, such replacement should be multifaceted and interactive in nature, and closely approximate the components of the normal ECM, leading to accelerated wound closure with minimal scar formation. Hence, while targeting or replacing the necessary matricellular proteins may be more efficacious than individual cytokine-mediated candidates it is difficult to know where to begin or what strategy may be successful.

To effectively manage these problems one must understand the healing process and to create a salubrious physical and biochemical environment conducive for healing. These non-healing wounds have been the subject of intensive investigation throughout the past 15 years. Much effort has focussed on recombinant growth factors. Given that the targets of members of the epidermal growth factor, fibroblast growth factor, platelet-derived growth factor (PDGF), and transforming growth factor-β families were cells that participated in the dermal wound repair process, it was logical to use this model as the first foray into clinical studies with these growth factors. With one notable exception (PDGF-BB or becaplermin), this drug development effort may be considered a failure for several reasons (Pierce & Mustoe 1995), among the most significant reason was that these growth factors typically target a single biological process essential for wound healing. To date, the only growth factor approved by the US Food and Drug Administration for the treatment of diabetic foot ulcers is recombinant PDGF-BB (becaplermin), which comes in as a topical cream. PDGF-B is known to be a potent mitogen and chemotatic agent for stromal cells and may act to increase the wound vascularization by stimulating angiogenesis. Thus there is an urgent need for better, new or adjunctive treatments.

Angiopoietin-like protein 4 (ANGPTL4) are secreted proteins mainly expressed in liver that have been demonstrated to regulate triglyceride metabolism by inhibiting the lipolysis of triglyceride-rich lipoproteins. Experimental results show that ANGPTL4 function to regulate circulating triglyceride levels during different nutritional states and therefore play a role in lipid metabolism during feeding/ fasting through differential inhibition of Lipoprotein lipase (LPL). The N-terminal domain of Angiopoietin-like proteins has been shown to play an active role in lipid metabolism. Using deletion mutants, it was demonstrated that the N-terminal domain containing fragment—(17-207) and not the C-terminal fibrinogen-like domain containing fragment—(207-460) increased the plasma triglyceride levels in mice: ANGPTL4 has been identified as a novel paracrine and, possibly, endocrine regulator of lipid metabolism and a target of peroxisome proliferators-activated receptors (PPARs). It is expressed in numerous cell types, such as adipocytes and hepatocytes, and is upregulated after fasting and hypoxia. Importantly, ANGPTL4 undergoes proteolytic processing to release its C-terminal fibrinogen-like domain (cANGPTL4), which circulates as a monomer yet whose function remains unclear. The N-terminal coiled-coil domain of ANGPTL4 (nANGPTL4) mediates the oligomerization of ANGPTL4 and binds to lipoprotein lipase to modulate lipoprotein metabolism mediating oligomerization and lipoprotein metabolism. In contrast, cANGPTL4 exists as a monomer, and its function still remains unknown. ANGPTL4 has been showed to play a context-dependent role in angiogenesis and vascular permeability [13-15]. ANGPTL4, was a recently identified to be a matricellular protein implicated in regulation of energy metabolism and wound healing [12]. The deficiency in ANGPTL4 in mice (ANGPTL4$^{-/-}$) resulted in delayed wound re-epithelialization, reduced matrix proteins expression, an increased inflammation and an impaired wound-related angiogenesis [16,17]. However, the expression of ANGPTL4 and role in chronic wound repair, such as diabetic wound repair remains unclear.

SUMMARY

Accordingly, a first aspect of the invention includes a method for increasing wound healing in an individual in need thereof, the method comprising administering an angiopoietin like 4 (ANGPTL4) polypeptide or a therapeutically active fragment thereof.

Another aspect of the invention includes a pharmaceutical composition for increasing wound healing in an individual, comprising an angiopoietin like 4 (ANGPTL4) polypeptide or a therapeutically active fragment thereof and a pharmaceutically acceptable carrier.

Another aspect of the invention includes a method of determining whether a wound site will become a chronic slow-healing wound, comprising the steps of (a) determining the level of the angiopoietin like 4 protein (ANGPTL4) present in a sample taken from the wound site (b) comparing the level of the angiopoietin like 4 protein (ANGPTL4) from the sample with a control from a healthy individual (with normal wound healing), wherein a reduced level of ANGPLT4 in the sample compared with the control is indicative that the wound site will become a chronic slow-healing wound.

Other aspects of the invention would be apparent to a person skilled in the art with reference to the following drawings and description of various non-limiting embodiments.

BRIEF DESCRIPTION OF THE DRAWINGS

The drawings are not necessarily drawn to scale, emphasis instead generally being placed upon illustrating the principles of various embodiments. In the following description, various embodiments of the invention are described with reference to the following drawings.

(A) Representative images of normal (ob/+) and diabetic (ob/ob) wound biopsies taken at day 1, 3, 5, 7 and 10 post wounding. Scale bar: 5 mm.

(B) Wound closure kinetics of ob/+ and ob/ob mice. Wound surface areas are plotted as percentage of day 0 (=100%) wound surface area. Data are mean±SEM, n=10.

(C) Relative mRNA expression of ANGPTL4 in ob/+ and ob/ob wound biopsies on indicated day post-injury as determined by qPCR. The ribosomal protein L27 serves as reference housekeeping gene. Data are mean±SEM from 3 independent studies performed in triplicates.

(D) Immunoblot analysis of cANGPTL4 from ob/+ and ob/ob wound biopsies. β-tubulin served as loading and transfer controls. The graph shows the relative protein expression level of cANGPTL4 from ob/+ and ob/ob wound biopsies on indicated days post-wounding. Densitometry values of protein bands were determined using imageJ software. Data are mean±SEM from three independent wound studies.

(E) Immunofluorescence staining of ANGPTL4 (red) in ob/+ and ob/ob wound biopsies. Sections were counter-stained with DAPI (blue). Dotted line delineates the epidermis and dermis interface, scale bar: 40 μm Using Mann-Whitney test: *$p<0.05$; $p<0.01$ and *$p<0.001$.

Figure 2:
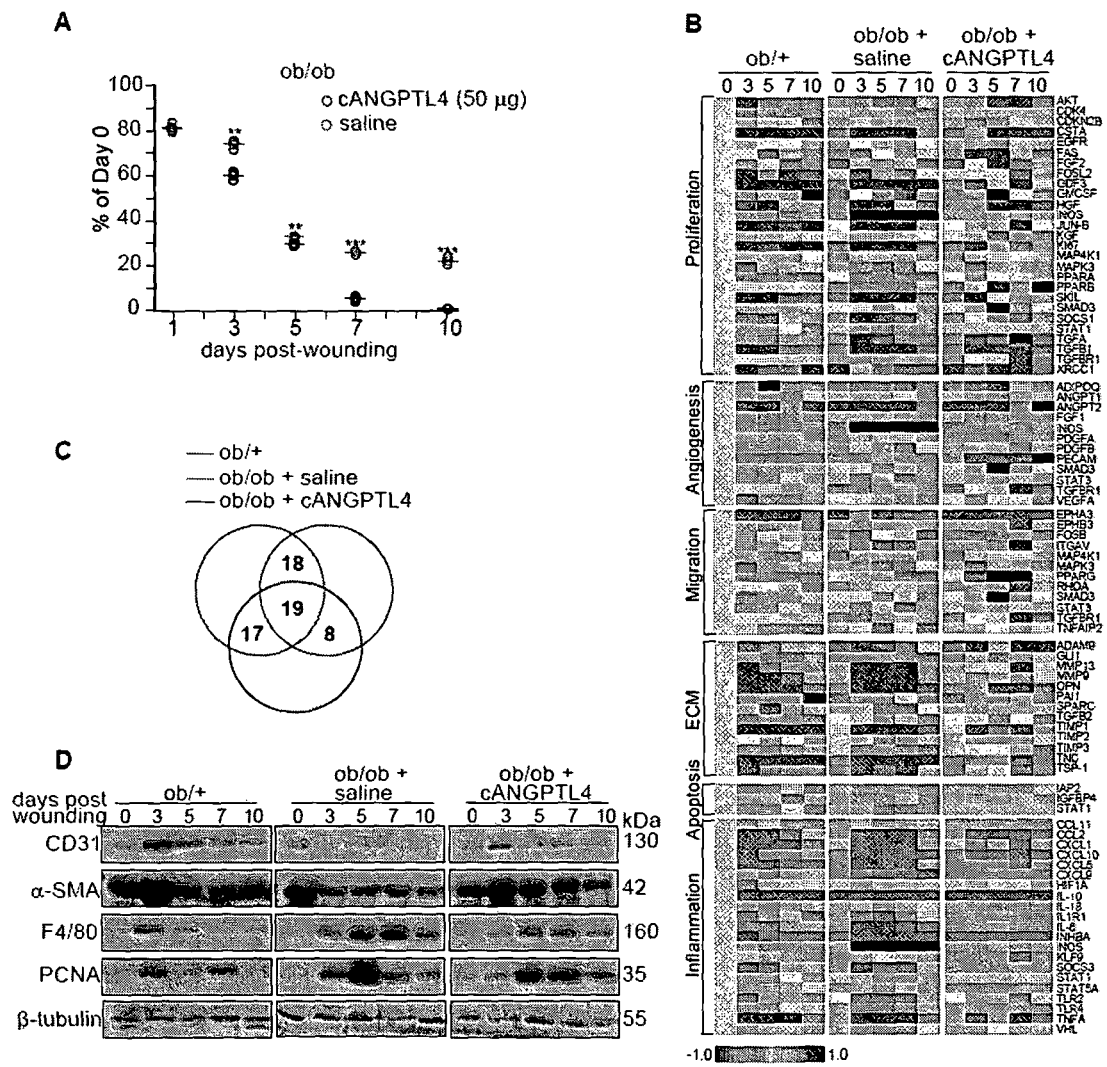
Figure 2:
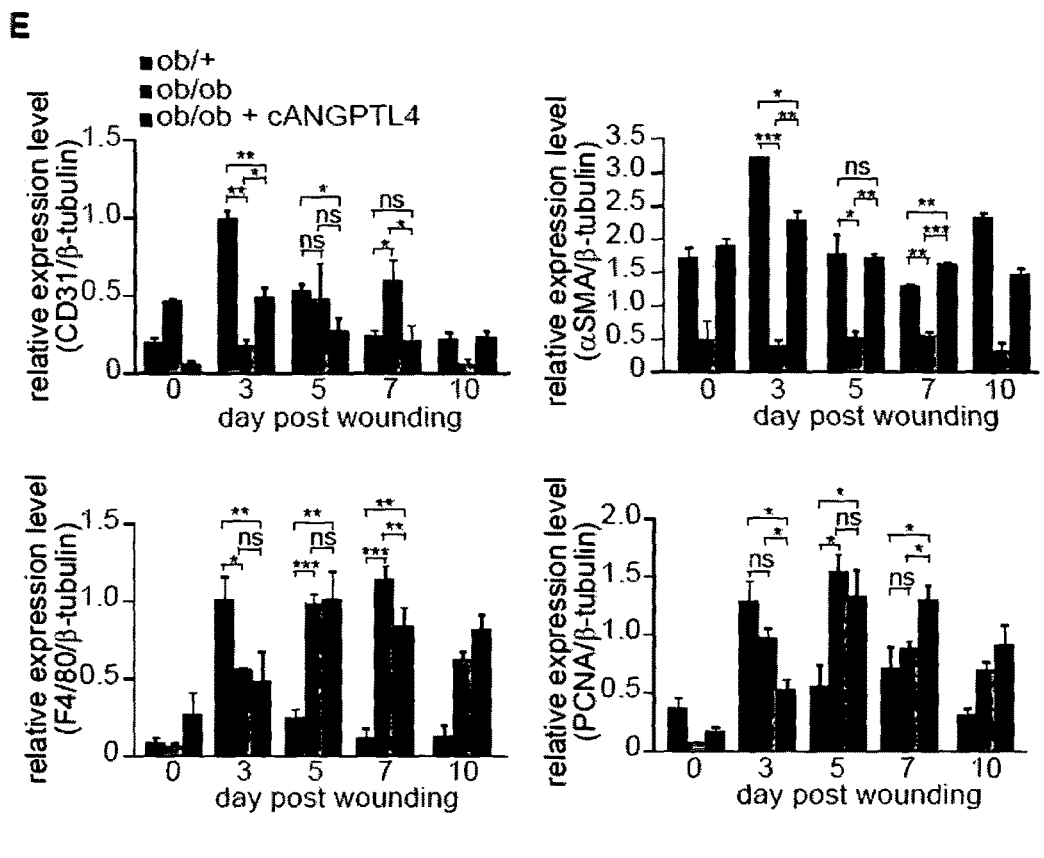
Figure 2:
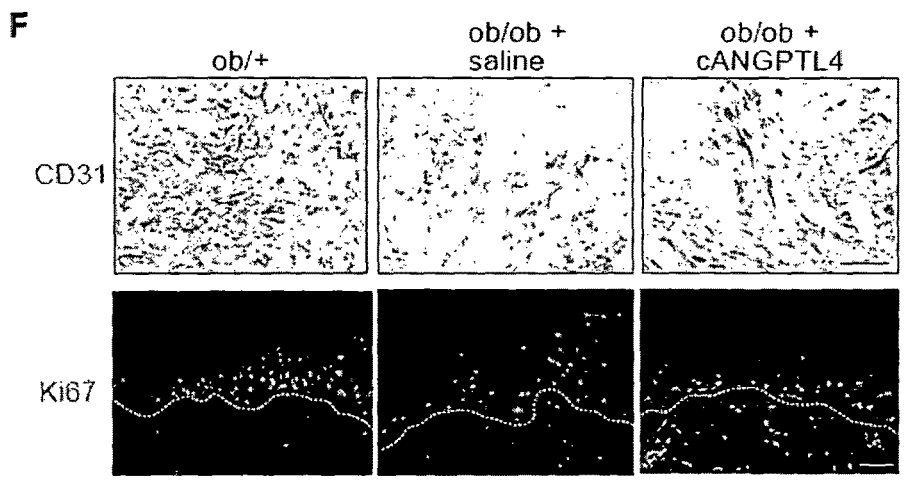

FIG. 2. Topical application of ANGPTL4 improved diabetic wound healing.

(A) Wound closure kinetics of diabetic ob/ob wounds treated with a single dose of either saline or cANGPTL4 (50 μg) in 1% carboxyl methylcellulose. Wound surface areas are plotted as percentage of day 0 (=100%) wound surface area. Data are mean±SEM, n=10. Using Mann-Whitney test: $p<0.01$ and *$p<0.001$.

(B) Heatmaps showing gene expression profiles of ob/+, saline- and cANGPTL4-treated ob/ob wounds. Genes were sorted and clustered according to their biological gene functions: proliferation, angiogenesis, migration, ECM, apoptosis and inflammation. Color spectrum from blue to red depicts Log-fold change from −1.0 to 1.0.

(C) Venn diagram comparing total number of genes from ob/+(blue), saline- (red) and cANGPTL4-treated ob/ob (black).

(D) Representative immunoblot of indicated proteins from ob/+, saline- and cANGPTL4-treated ob/ob wound biopsies on various days post-wounding. β-tubulin served as loading and transfer controls.

(E) The graph shows the relative protein expression level of indicated proteins from ob/+, saline- and cANGPTL4-treated ob/ob wound biopsies on indicated days post-wounding. Densitometry values of protein bands were determined using imageJ software. Data are mean±SEM from three independent studies. *$p<0.05$; $p<0.01$, *$p<0.001$.

(F) Immunohistochemistry and immunofluorescence staining of CD31 (brown) and Ki67 (green) of ob/+, saline- and cANGPTL4-treated ob/ob wound biopsies. Dotted line delineates the epidermis and dermis interface, scale bar: 40 μm.

Figure 3:
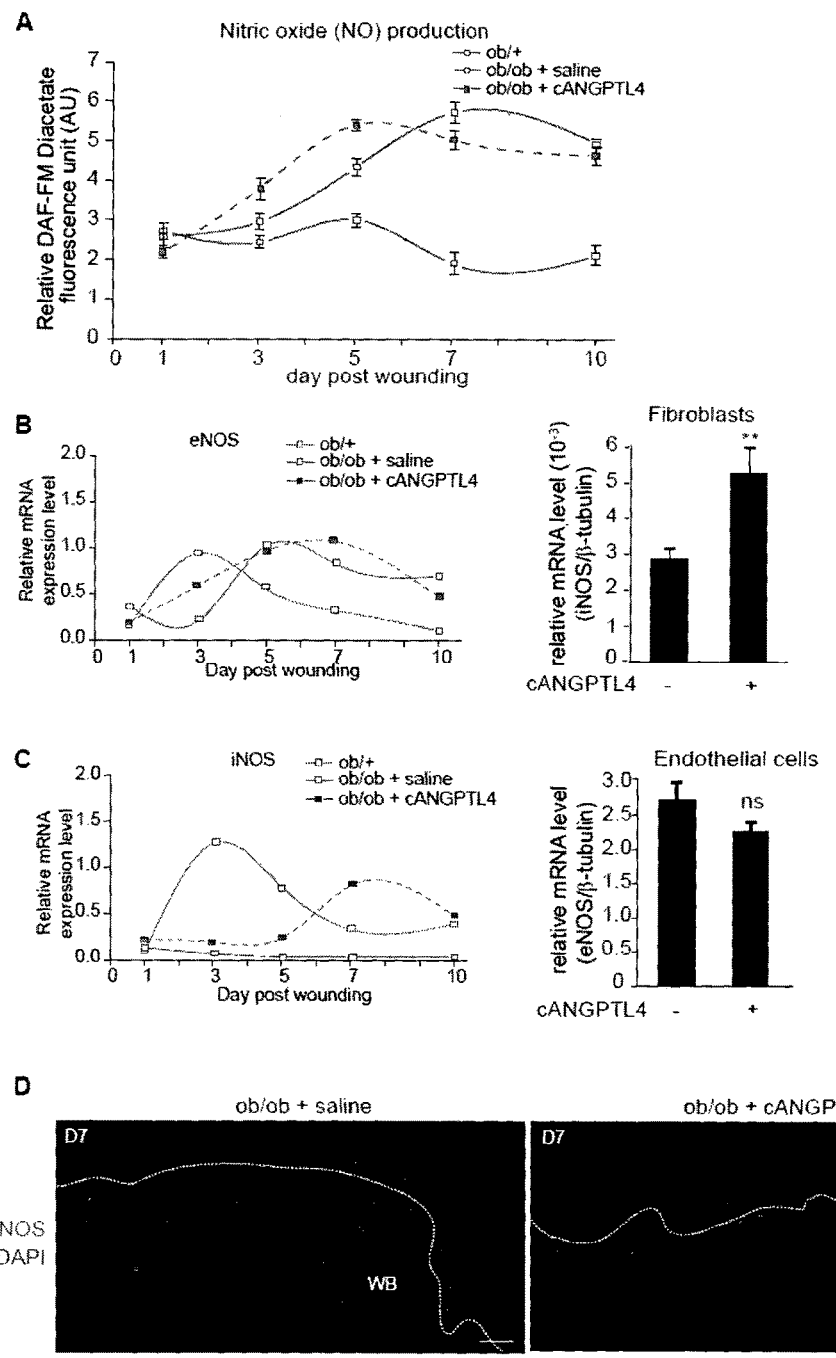

FIG. 3. ANGPTL4 regulate the NO production in ob/ob mice.

(A) Nitric oxide production in ob/+, saline- and cANGPTL4 treated ob/ob at indicated days post-wounding as determined by DAF-FM diacetate fluorescence (arbitrary unit, AU). Values were normalized with total protein concentration measured by UV 280 nm spectrophotometry. Data are mean±SEM from three independent experiments, n=10.

(B-C) Graph showing the relative mRNA expression level of eNOS (B, left panel) and iNOS (C, left panel) from ob/+, saline- and cANGPTL4-treated wound biopsies on indicated days post-wounding as determined by qPCR. The ribosomal protein L27 serves as reference housekeeping gene. Graphs show the relative mRNA level of iNOS in primary human fibroblasts (B, right panel) and eNOS in primary human dermal microvascular endothelial cells (C, right panel) upon treatment with cANGPTL4 compared with cognate untreated control. Data are mean±SEM from 3 independent studies performed in triplicates **$p<0.01$ (D) Immunofluorescence staining of iNOS (red) on saline- and cANGPTL4-treated ob/ob wound biopsies on day 7 post-injury wound biopsies. Nuclei (blue) are counterstained with DAPI. Dotted line delineates the epidermis and dermis interface, scale bar: 50 μm. WB: wound bed.

Figure 4:
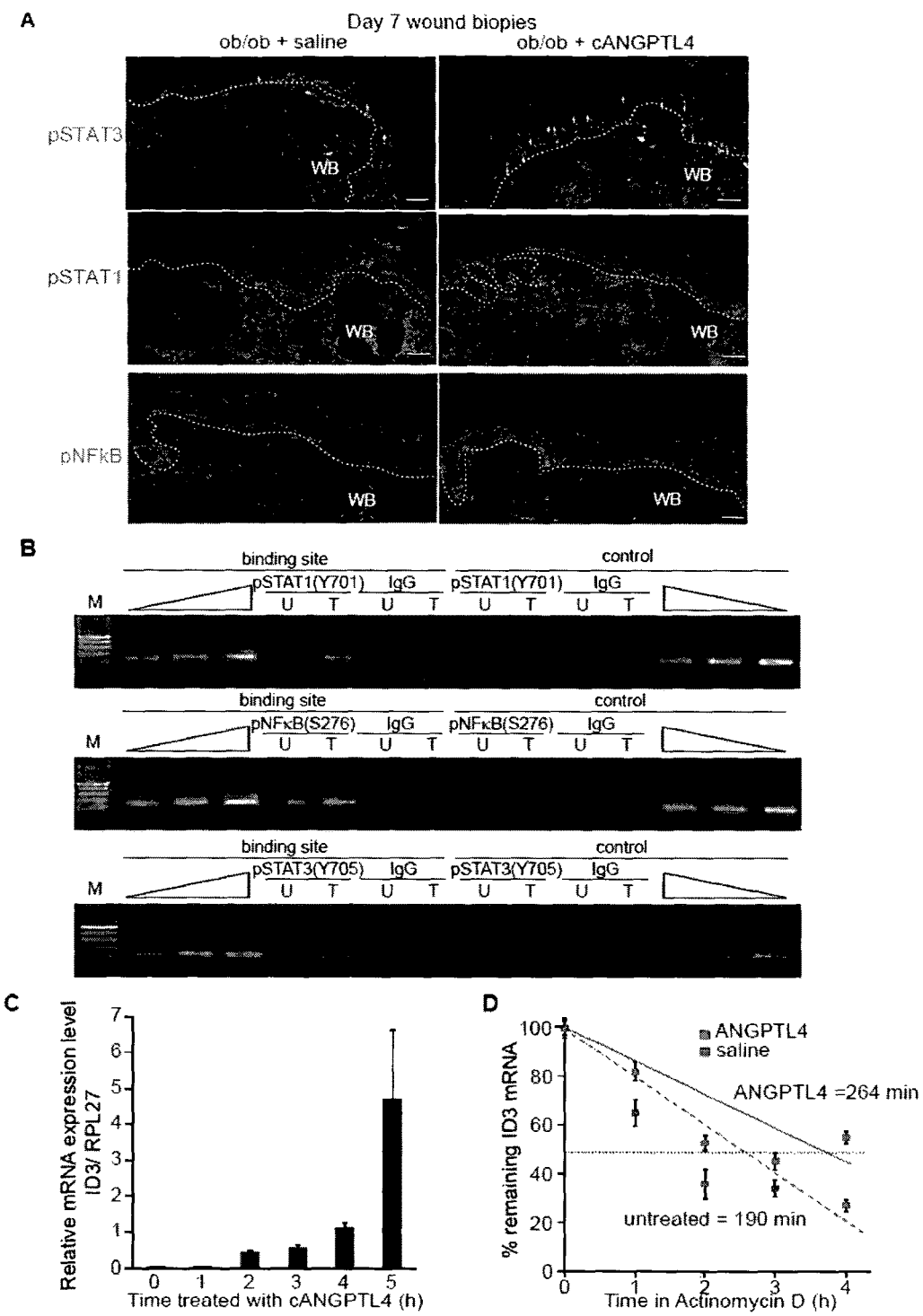

FIG. 4. ANGPTL4 regulates iNOS expression.

(A) Representative immunofluorescence staining of pSTAT3(Y705) (green), pSTAT1(Y701) (red) and pNFκB (S276) (green) on ob/+, saline- and cANGPTL4-treated ob/ob Day 7 post-wounding biopsies. Nuclei (white) are counterstained with DAPI. Dotted line delineates the epidermis and dermis interface, scale bar: 40 μm. WB: wound bed.

(B) ChIP assays were conducted using pre-immune IgG or antibodies against pSTAT3(Y705), pSTAT1(Y701) and pNFκB(S276) in saline- (U) and cANGPTL4-treated ob/ob (T) Day 7 wound biopsies. The regions spanning promoter binding sites of the mouse iNOS gene were amplified using appropriate primers (Table S1). A control region upstream of the binding sites served as negative control.

(C) Relative mRNA expression of ID3 in human dermal fibroblasts at indicated time post cANGPTL4 treatment. The ribosomal protein L27 serves as reference housekeeping gene. Data are mean±SEM from three independent experiments.

(D) Relative stability of ID3 mRNA in human dermal fibroblasts treated with cANGPTL4 treated or saline (vehicle) in the presence of actinomycin D (10 μg/μl). The ribosomal protein 18S serves as reference housekeeping gene. The relative mRNA expression level of ID3 was determined by qPCR, normalized to 18S values, and plotted as a percentage of value at time zero. The half-lives of each mRNA were calculated by linear regression analysis using Orgin Pro 8,1. Data are mean±SEM from three independent experiments.

Figure 5:
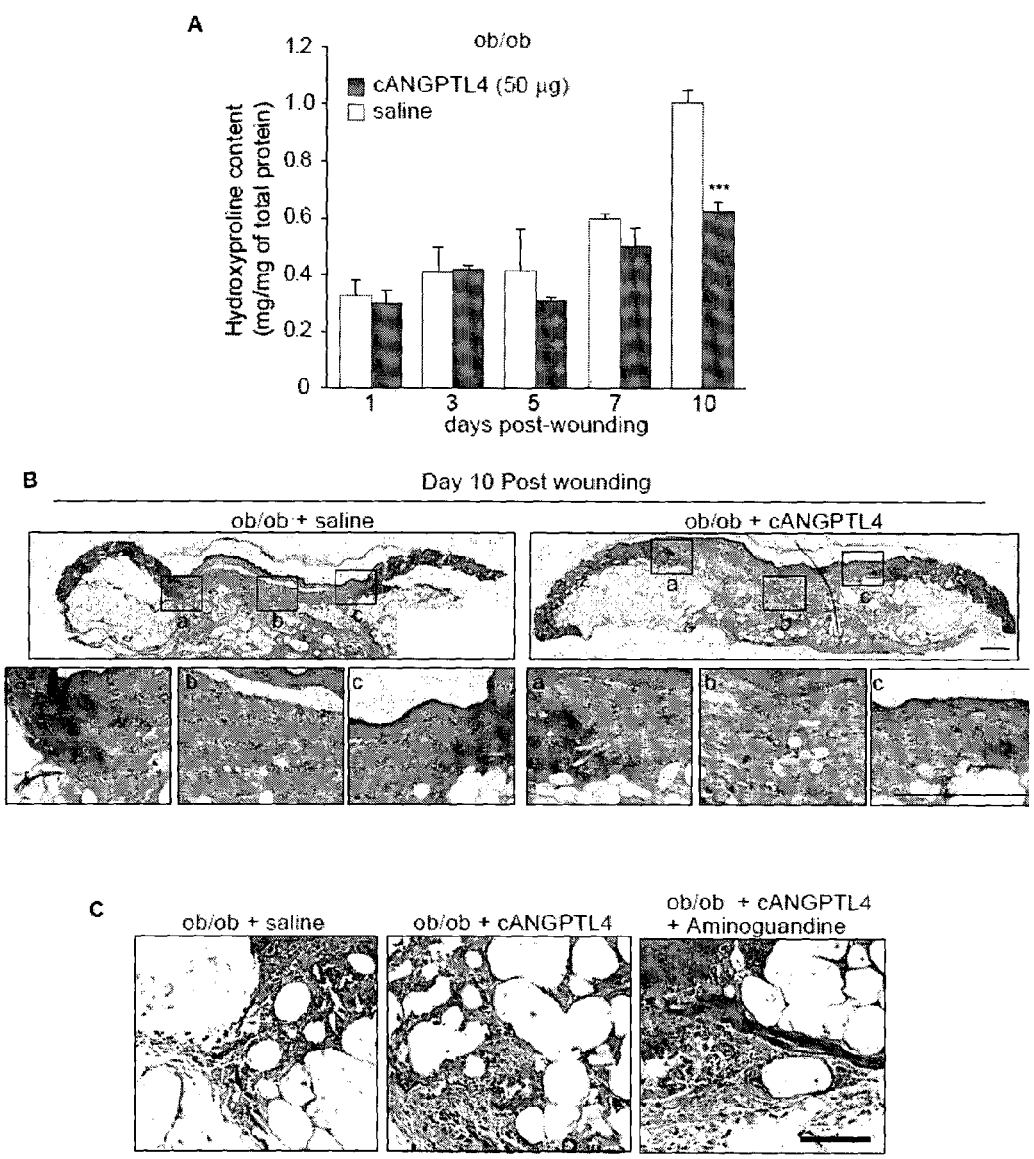
Figure 5:
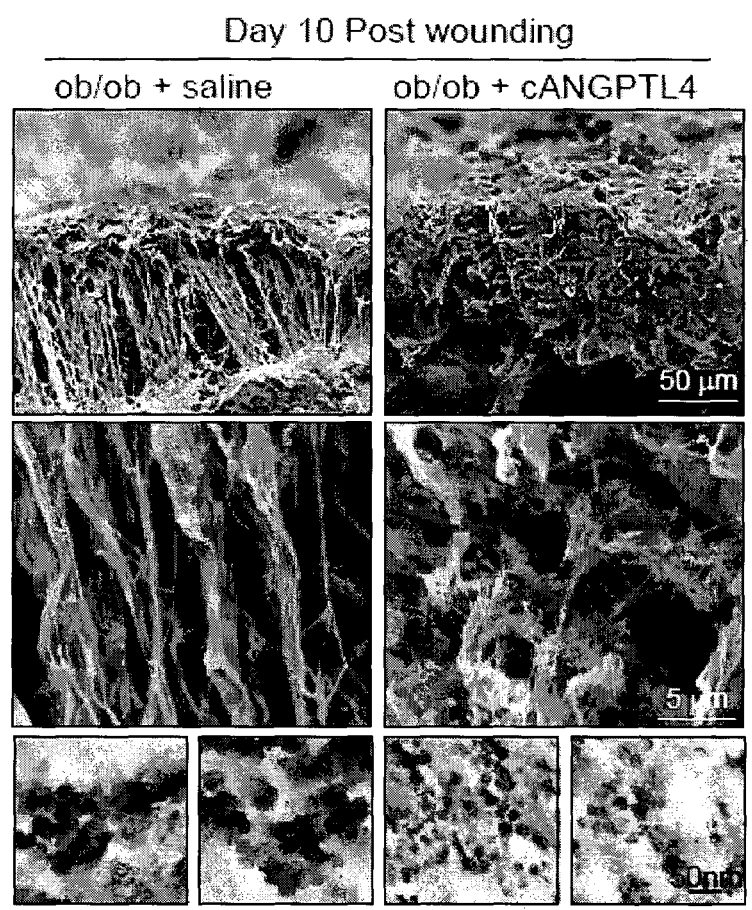

FIG. 5. ANGPTL4 reduced collagen scar tissue in ob/ob wounds.

(A) Hydroxyproline content of indicated wound tissues from saline- and cANGPTL4-treated ob/ob. Total amount of hydroxyproline (mg) were determined from a hydroxyproline standard curve and normalized with the total protein concentration measured by UV 280 nm spectrophotometry. Data are mean±SEM, n=3 ***$p<0.001$.

(B) Representative Van Gieson's staining of day 10 wound sections from saline- and cANGPTL4-treated ob/ob wounds. Collagen is stained red, muscle or fibrin stained yellow and nuclei were stained black.

(C) Masson's trichrome staining of day 10 wound sections from saline-, cANGPTL4-treated and cANGPTL4 with aminoguanidine-treated ob/ob wounds. Collagen fibers were stained blue, cytoplasm stained red and nuclei were stained black.

(D) Representative scanning electron (SEM, top and middle panels) and transmission electron microscopy (TEM, bottom panel) images of connective tissue near the wound bed region of saline- and cANGPTL4-treated ob/ob wound from day 10 post wounding. Cross sectional image of collagen fibrils size from corresponding wound biopsies were imaged TEM. Scale bar: top panel, 50 μm; middle panel, 5 μm and bottom panel, 50 nm.

Figure 6:
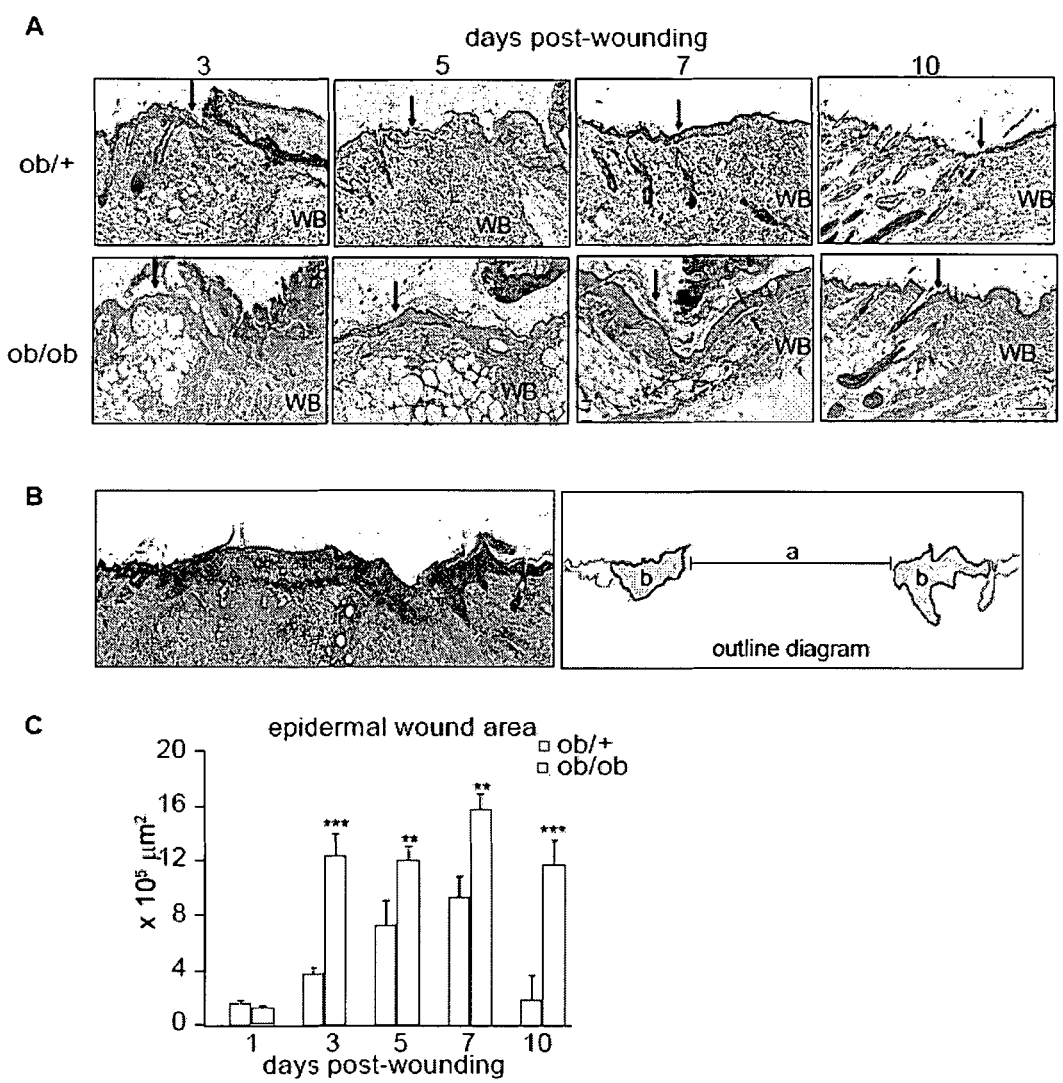

FIG. 6. Hematoxylin and Eosin (H&E) staining of wound sections.

(A) Representative Hematoxylin and Eosin (H&E) staining of wound sections from ob/+ and ob/ob mice at indicated days post wounding. WB, wound bed. Arrows indicate the wound edge. Dotted line delineates the epidermis and dermis interface. Scale bar: 100 μm.

(B) Schematic representation (right panel) of the H&E stained wound section (left panel). Epithelial gap (a) was measured as the distance of re-epithelization gap between the two margins of the inward growing epithelium. Epidermal wound area (b) was measured by the area of the epithelium within the epithelial tongue.

(C) Epidermal wound area of ob/+ and ob/ob wound biopsies sections. All the measurements are performed three times from three random sections for each indicated time point using Adobe Photoshop CS5.1. Image pixel was calibrated to μm using the scale bar. Data are mean±SEM, n=9 (*$p<0.05$).

Figure 7:
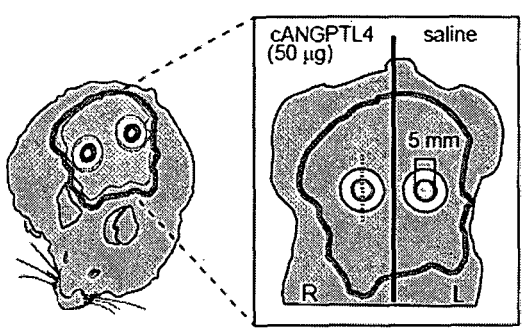
Figure 7:
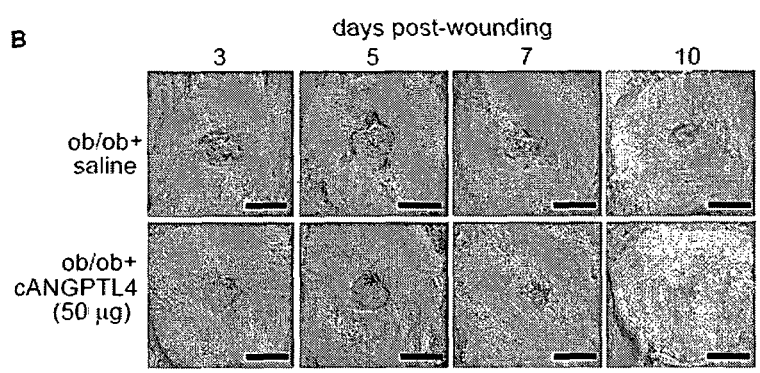
Figure 7:
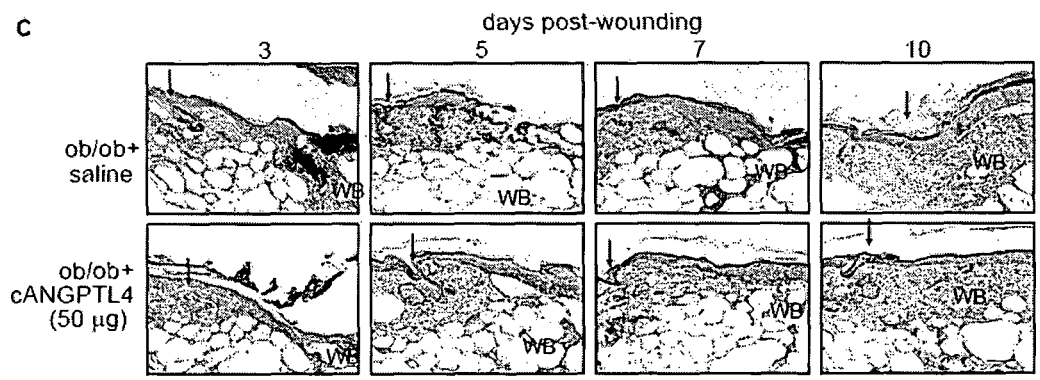

FIG. 7. Topical application of recombinant ANGPTL4 on full-thickness splint wounds in diabetic ob/ob mice.

(A) A schematic diagram illustrating the location and dimensions of full-thickness excision splint wounds on the dorsal skin of diabetic mice. Topical application of cANGPTL4 and control saline were both performed on each mouse. Application sites were rotated to avoid site bias. Blue dotted lines indicate centrally dissected wound tissues.

(B) Photo images of saline- and cANGPTL4-treated ob/ob wound biopsies taken at day 3, 5, 7 and 10 post-wounding. Scale bar: 5 mm.

(C) Representative H&E staining of wound sections from saline- and cANGPTL4-treated ob/ob mice wound biopsies. Red arrows indicate the wound edge. Dotted line delineates the epidermis and dermis interface. Scale bar: 100 μm. WB, wound bed.

Figure 8:
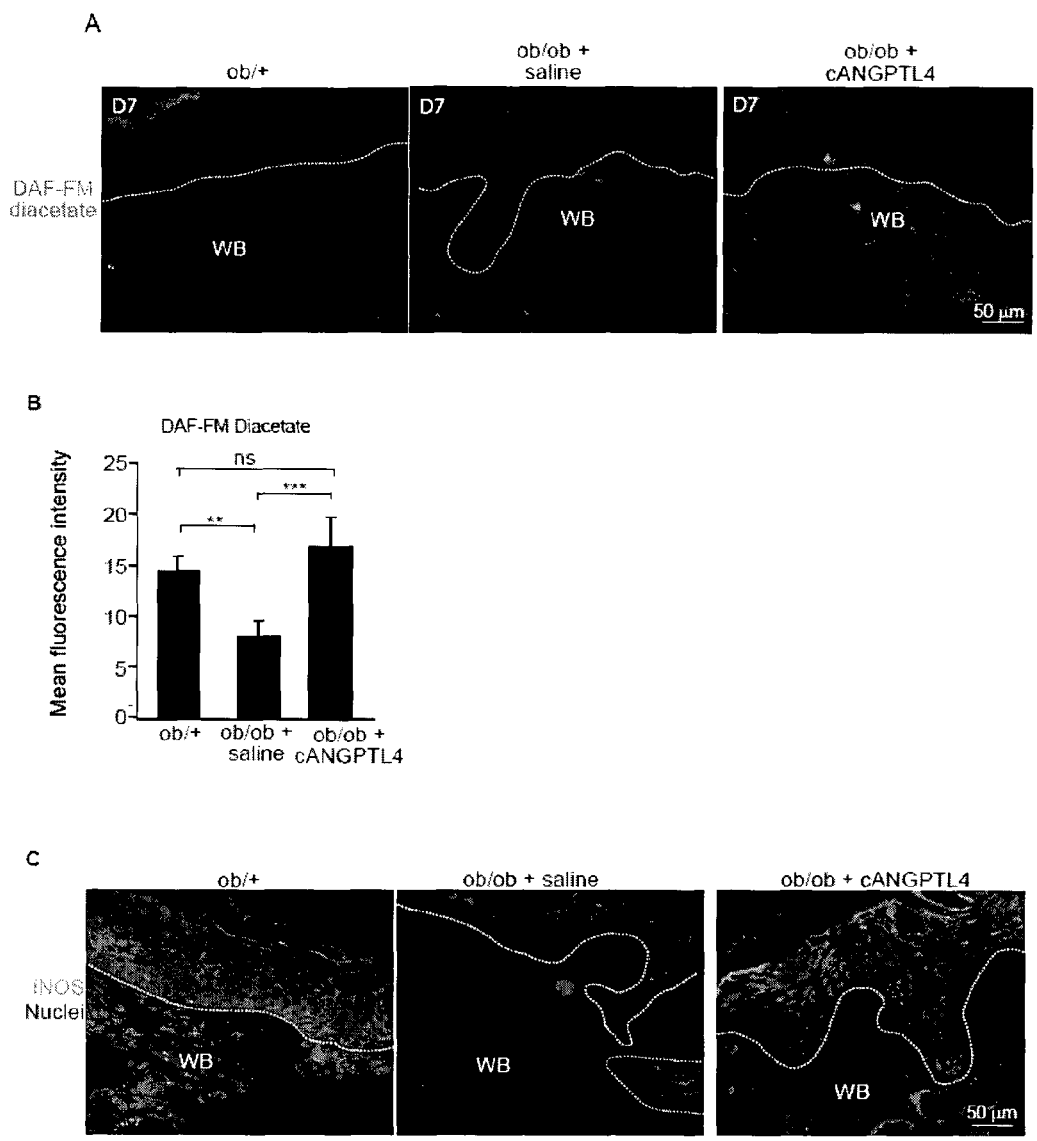

FIG. 8. Nitric oxide and iNOS levels in wounds treated or not with ANGPTL4.

(A) Representative fluorescence images of wound biopsies stained with DAF-FM diacetate (green) to detect nitric oxide. Wound sections were from day 7 post-injury biopsies of ob/+, saline- and cANGPTL4-treated ob/ob. Dotted line delineates the epidermis and dermis interface. Scale bar: 50 WB, wound bed.

(B) Mean fluorescence intensity of DAF-FM diacetate from wound sections stained as described in (A). Mean fluorescence intensity values (arbitrary unit, AU, ±SEM) were calculated from at least three biopsies and three microscopic fields of each tissue *$p<0.05$, ** $p<0.01$.

(C) Representative immunofluorescence staining of iNOS (green) in ob/+, saline- and cANGPTL4-treated ob/ob wound biopsies on day 7 post-injury. Nuclei were counterstained with DAPI (blue). Dotted line delineates the epidermis and dermis interface, scale bar: 50 μm.

Figure 9:
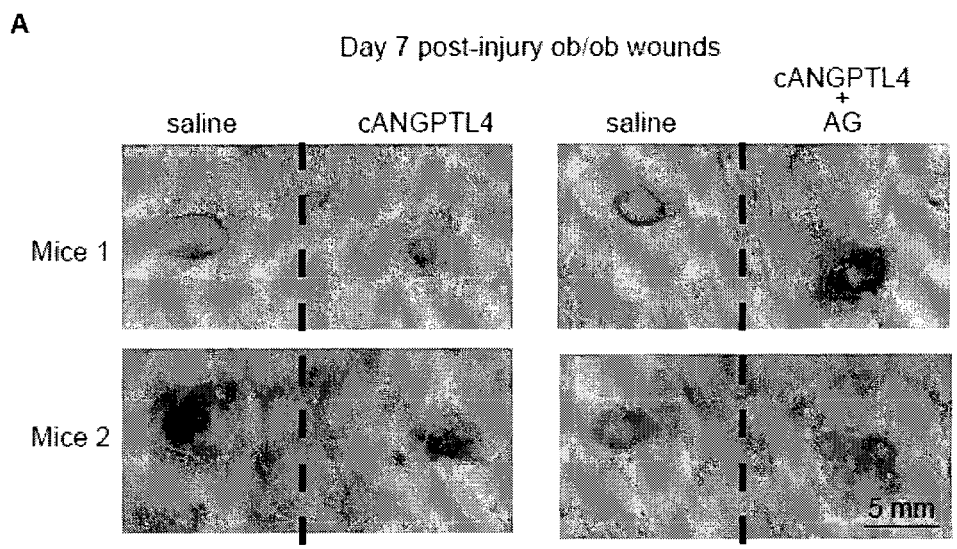
Figure 9:
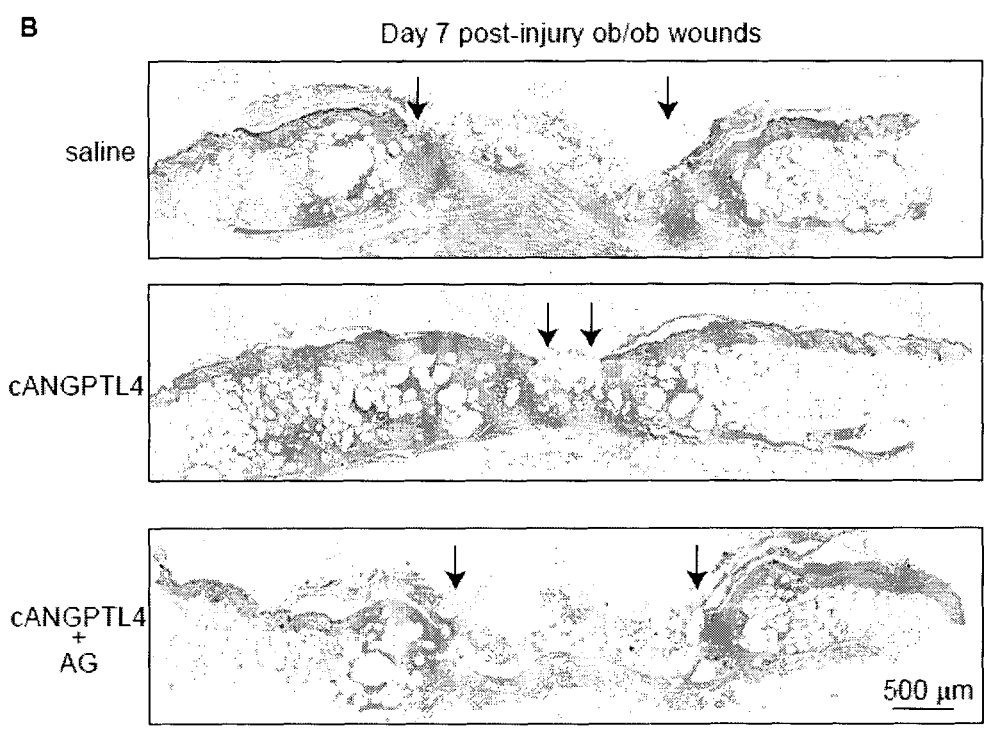

FIG. 9. Effects of aminoguanidine of ANGPTL4 mediated wound healing.

(A) Photo images of saline-, cANGPTL4-treated ob/ob and cANGPTL4 with aminoguanidine (AG)-treated ob/ob wounds from two mice. Images were taken at day 7 post-wounding. Scale bar: 5 mm.

(B) Representative hematoxylin and eosin (H&E) images of wound sections from saline-, cANGPTL4- and cANGPTL4 with AG-treated ob/ob wounds at day 7 post-injury.

Scale bar: 500 µm. Arrows point to the epithelial wound edge.

DETAILED DESCRIPTION

We showed that topical application of ANGPTL4, specifically the C-terminal fibrinogen-like domain (cANGPTL4), accelerates wound closure of splint-wound model in diabetic mice and reduces collagen deposition i.e. scarring at the remodelling stage of wound healing. cANGPTL4 is a matricellular protein, thus it can modulate many critical regulatory networks during wound healing. Thus, matricellular protein ANGPTL4 is more efficacious than individual cytokine-mediated candidates.

Accordingly, a first aspect of the invention includes a method for increasing wound healing in an individual in need thereof, the method comprising administering an angiopoietin like 4 (ANGPTL4) polypeptide or a therapeutically active fragment thereof.

Polypeptides of the angiopoietin like 4 (ANGPTL4) polypeptide preferably have about 406 amino acids, encoding an enzyme having many activities such as interacting with specific matrix proteins in the wound bed, delaying their proteolytic degradation by MMPs, and directly affects cell-matrix communication by altering the availability of intact matrix proteins. ANGPTL allows crosstalk of various cells such as wound keratinocytes, dermal fibroblasts, endothelial cells or inflammatory cells with the surrounding ECM. We also showed that ANGPTL4 reduced collagen deposition towards the later stage of wound healing.

Preferably, the angiopoietin like 4 (ANGPTL4) polypeptide or therapeutically active fragment thereof comprises; (i) an amino acid sequence set forth in SEQ ID NO:1; or (ii) an amino acid sequence having at least 60, at least 70, at least 80, at least 85, at least 90, at least 95, at least 97, at least 98 or at least 99% sequence identity with the amino acid sequence set forth in SEQ ID NO:1 over its entire length; or (iii) an amino acid sequence having at least 70, at least 80, at least 85, at least 90, at least 95, at least 97, at least 98 or at least 99 sequence homology with the amino acid sequence set forth in SEQ ID NO: 1 over its entire length; or (iv) a fragment of any one of (i) to (iii).

Preferably the therapeutically active fragment comprises the C terminal region of the angiopoietin like 4 (ANGPTL4) polypeptide or a functional fragment thereof. In various embodiments the fragment comprises: (i) the amino acid sequence set forth in SEQ ID NO:2; or (ii) an amino sequence having at least 60, at least 70, at least 80, at least 85, at least 90, at least 95, at least 97, at least 98 or at least 99% sequence identity with the amino acid sequence set forth in SEQ ID NO:2 over its entire length; or (iii) an amino acid sequence having at least 70, at least 80, at least 85, at least 90, at least 95, at least 97, at least 98 or at least 99 sequence homology with the amino acid sequence set forth in SEQ ID NO: 2 over its entire length.

The functional domain of the C terminal fibrinogen like domain of ANGPTL4 (cANGPTL4) comprises or consists of amino acids 186 to 406 of the amino acid sequence shown as SEQ ID NO: 1 or allelic variants, homologues or fragments, thereof. The C ANGPTL4 domain preferably comprises SEQ ID NO. 2 or a sequence having homology with the amino acid sequence set forth in SEQ ID NO: 2.

The term "polypeptide" refers to a polymer of amino acids and its equivalent and does not refer to a specific length of the product; thus, peptides, oligopeptides and proteins are included within the definition of a polypeptide. This term also does not refer to, or exclude modifications of the polypeptide, for example, glycosylates, acetylations, phosphorylations, and the like. Included within the definition are, for example, polypeptides containing one or more analogs of an amino acid (including, for example, natural amino acids, etc.), polypeptides with substituted linkages as well as other modifications known in the art, both naturally and non-naturally occurring.

The term 'wound' refers to a type of injury where the dermis of the skin is disrupted forming a tear, cut, puncture, incision, laceration, abrasion, rip, slash, scratch, slit or rupture in the skin of an animal. Such wounds may include ulcers such as venous ulcers, pressure ulcers or diabetic foot. Diabetic foot refers to chronic slow healing wounds on the lower limbs of an individual who may have diabetes. In various embodiments the wound is selected from an ulcer, a chronic slow-healing wound and an open wound.

To increase wound healing refers to reducing the size of the wound surface area preferably until the dermis is mostly or completely covering the area, essentially, healing the wound. Wound healing may be measured as a percentage of the reduction of the wound surface area to the initial surface area at the time of the application of the composition or composition described herein. "Treatment" and "treat" and synonyms thereof refer to therapeutic treatment wherein the object is to speed up (increase) wound healing by reducing the size of the wound surface area in the shortest amount of time. Increasing wound healing may include reducing the amount of collagen in the wound site, reducing visible scarring or increased expression of nitric oxide synthase (iNOS). Treatment may include prophylactic passive treatment of a patent at the time of surgery. Those in need of such treatment include those with a wound such as a cut, an ulcer or a disruption of the skin or a chronic slow healing wound common in individuals with diabetes. An individual refers to an animal, such as a mammal, preferably a human. In various embodiments the individual has diabetes.

In various embodiments the methods of the invention may further comprise the step of performing an adjunct treatment. The adjunct treatment may include a debridement treatment such as the use of papain or other debridement agents known in the art. The adjunct treatment may include a cytokine treatment. The adjunct treatment may include a hyperbaric oxygen treatment. Similarly, the adjunct treatment may include dressing selection and diabetic shoes or any other treatments known in the art.

Preferably the angiopoietin like 4 (ANGPTL4) polypeptide comprises; (i) an amino acid sequence set forth in SEQ ID NO:1; or (ii) an amino acid sequence having at least 60, at least 70, at least 80, at least 85, at least 90, at least 95, at least 97, at least 98 or at least 99% sequence identity with the amino acid sequence set forth in SEQ ID NO:1 over its entire length; or (iii) an amino acid sequence having at least 70, at least 80, at least 85, at least 90, at least 95, at least 97, at least 98 or at least 99 sequence homology with the amino acid sequence set forth in SEQ ID NO: 1 over its entire length; or (iv) a functional fragment of any one of (i) to (iii).

Preferably the polypeptide of the C terminal region of the angiopoietin like 4 (ANGPTL4) polypeptide or the functional fragment comprise; (i) the amino acid sequence set forth in SEQ ID NO:2; or (ii) an amino acid sequence having at least 60, at least 70, at least 80, at least 85, at least 90, at least 95, at least 97, at least 98 or at least 99% sequence identity with the amino acid sequence set forth in SEQ ID NO:2 over its entire length; or (iii) an amino acid sequence having at least 70, at least 80, at least 85, at least 90, at least 95, at least 97, at least 98 or at least 99 sequence homology with the amino acid sequence set forth in SEQ ID NO: 2 over its entire length.

In the context of the present invention, a homologous sequence is taken to include an amino acid sequence which is at least 60, 70, 80 or 90% identical, preferably at least 95 or 98% identical at the amino acid level over at least 20, 50, 100, 200, 300 or 400 amino acids with the amino acid sequences set out in SEQ ID. NO 1 or the amino acid sequences set out in SEQ ID. NO 2. In particular, homology should typically be considered with respect to those regions of the sequence known to be essential for the function of the protein rather than non-essential neighbouring sequences. Preferred polypeptides of the invention comprise a contiguous sequence having greater than 50, 60 or 70% homology, more preferably greater than 80 or 90% homology, to one or more of amino acids of SEQ ID NO: 1 or to one or more of amino acids of SEQ ID NO: 2.

Other preferred polypeptides comprise a contiguous sequence having greater than 40, 50, 60, or 70% homology, of SEQ ID No: 1 and are capable of binding to SEQ ID No:1. Other preferred polypeptides comprise a contiguous sequence having greater than 50, 60, 70, or 80% homology, of SEQ ID No: 2 and are capable of binding to SEQ ID No:2 and having a similar effect on wound healing. Although homology can also be considered in terms of similarity (i.e. amino acid residues having similar chemical properties/functions), in the context of the present invention it is preferred to express homology in terms of sequence identity. The terms "substantial homology" or "substantial identity", when referring to polypeptides, indicate that the polypeptide or protein in question exhibits at least about 70% identity with an entire naturally-occurring protein or a portion thereof, usually at least about 80% identity, and preferably at least about 90 or 95% identity.

Homology comparisons can be conducted by eye, or more usually, with the aid of readily available sequence comparison programs. These commercially available computer programs can calculate % homology between two or more sequences.

Percentage (%) homology may be calculated over contiguous sequences, i.e. one sequence is aligned with the other sequence and each amino acid in one sequence directly compared with the corresponding amino acid in the other sequence, one residue at a time. This is called an "ungapped" alignment. Typically, such ungapped alignments are performed only over a relatively short number of residues (for example less than 50 contiguous amino acids).

Although this is a very simple and consistent method, it fails to take into consideration that, for example, in an otherwise identical pair of sequences, one insertion or deletion will cause the following amino acid residues to be put out of alignment, thus potentially resulting in a large reduction in % homology when a global alignment is performed. Consequently, most sequence comparison methods are designed to produce optimal alignments that take into consideration possible insertions and deletions without penalising unduly the overall homology score. This is achieved by inserting "gaps" in the sequence alignment to try to maximise local homology.

However, these more complex methods assign "gap penalties" to each gap that occurs in the alignment so that, for the same number of identical amino acids, a sequence alignment with as few gaps as possible—reflecting higher relatedness between the two compared sequences—will achieve a higher score than one with many gaps. "Affine gap costs" are typically used that charge a relatively high cost for the existence of a gap and a smaller penalty for each subsequent residue in the gap. This is the most commonly used gap scoring system. High gap penalties will of course produce optimised alignments with fewer gaps. Most alignment programs allow the gap penalties to be modified. However, it is preferred to use the default values when using such software for sequence comparisons. For example when using the GCG Wisconsin Bestfit package the default gap penalty for amino acid sequences is −12 for a gap and −4 for each extension.

Calculation of maximum % homology therefore firstly requires the production of an optimal alignment, taking into consideration gap penalties. A suitable computer program for carrying out such an alignment is the GCG Wisconsin Bestfit package and others known in the art. Examples of other software that can perform sequence comparisons include, but are not limited to, the BLAST package and the GENEWORKS suite of comparison tools. Both BLAST and FASTA are available for offline and online searching.

Although the final % homology can be measured in terms of identity, the alignment process itself is typically not based on an all-or-nothing pair comparison. Instead, a scaled similarity score matrix is generally used that assigns scores to each pairwise comparison based on chemical similarity or evolutionary distance. An example of such a matrix commonly used is the BLOSUM62 matrix—the default matrix for the BLAST suite of programs. GCG Wisconsin programs generally use either the public default values or a custom symbol comparison table if supplied (see user manual for further details). It is preferred to use the public default values for the GCG package, or in the case of other software, the default matrix, such as BLOSUM62.

Once the software has produced an optimal alignment, it is possible to calculate % homology, preferably % sequence identity. The software typically does this as part of the sequence comparison and generates a numerical result.

The polypeptide homologues include those having the amino acid sequences, wherein one or more of the amino acids is substituted with another amino acid which substitutions do not substantially alter the biological activity of the molecule. A ANGPTL4 or cANGPTL4 homologue according to the invention preferably has 80 percent or greater amino acid sequence identity to the polypeptide amino acid sequence set out in SEQ ID NO: 1 or SEQ ID NO:2 and has a similar effect on wound healing. Examples of polypeptide homologues within the scope of the invention include the amino acid sequence of SEQ ID NOS: 1 or 2 wherein: (a) one or more aspartic acid residues is substituted with glutamic acid; (b) one or more isoleucine residues is substituted with leucine; (c) one or more glycine or valine residues is substituted with alanine; (d) one or more arginine residues is substituted with histidine; or (e) one or more tyrosine or phenylalanine residues is substituted with tryptophan.

Preferably "protein" or "polypeptide" refers to a protein or polypeptide encoded by a nucleic acid sequence expressing the amino acid sequences set forth in SEQ ID NO: 1 or SEQ ID NO.2, variants or fragments thereof. Also included are proteins encoded by DNA that hybridize under high or low stringency conditions, to the encoding nucleic acids. Closely related polypeptides or proteins retrieved by antisera to the polypeptide of SEQ ID NO. 1 or SEQ ID NO: 2 is also included.

"Protein modifications or fragments" are provided by the present invention for the polypeptides or fragments thereof which are substantially homologous to primary structural sequences but which include, e.g., in vivo or in vitro chemical and biochemical modifications or which incorporate unusual amino acids. Such modifications include, for example, acetylation, carboxylation, phosphorylation, glycosylation, ubiquitination, labeling, e.g., with radionuclides, and various enzymatic modifications, as will be readily appreciated by those well skilled in the art. A variety of methods for labeling polypeptides and of substituents or labels useful for such purposes are well known in the art, and include radioactive isotopes such as $^{32}P$, ligands which bind to labeled antiligands (e.g., antibodies), fluorophores, chemiluminescent agents, enzymes, and antiligands which can serve as specific binding pair members for a labeled ligand. The choice of label depends on the sensitivity required, ease of conjugation with the primer, stability requirements, and available instrumentation. Methods of labeling polypeptides are well known in the art.

The 'polypeptide' may include any of the polypeptides described herein made according to methods known in the art such as recombinant production in prokaryotic or eukaryotic cells for example in CHO cells or via synthetic methods such as tBoc or Fmoc as is known in the art. Alternatively, the composition may include an agonist that increases the natural expression of ANGPTL4 in a wound site. Hypoxic conditions are known to induce ANGPTL4 expression. Hypoxia induction factor alpha (HIF-á) induces expression of ANGPTL4. Similarly, peroxisome proliferator-activated receptor (PPAR) proteins are transcription factors that activates ANGPTL4 expression. As such the composition may include a PPAR protein or a HIF-á protein.

Another aspect of the invention includes a pharmaceutical composition for increasing wound healing in an individual, comprising an angiopoietin like 4 (ANGPTL4) polypeptide or a therapeutically active fragment thereof; and a pharmaceutically acceptable carrier.

Compositions of the Invention

Polypeptides produced according to the invention, can be administered for the treatment of wounds in the form of pharmaceutical compositions.

Thus, the present invention also relates to compositions including pharmaceutical compositions comprising a therapeutically effective amount of (a) an agonist to angiopoietin like 4 protein (ANGPTL4) and, or (b) an agonist of the C terminal region of angiopoietin like 4 protein (ANGPTL4) and a carrier. As used herein a composition will be therapeutically effective if it is able to affect wound healing.

Pharmaceutical forms of the invention suitable for topical application include sterile aqueous solutions such as sterile phosphate-buffered saline (where water soluble) or dispersions and sterile powders for the extemporaneous preparation of topical solutions and or one or more carrier. Alternatively, topical solutions may be delivered encapsulated in liposomes to assist their transport across cell membrane. Alternatively or in addition such preparations may contain constituents of self-assembling pore structures to facilitate transport across the cellular membrane. It must be stable under the conditions of manufacture and storage and must be preserved against the contaminating/destructive action of microorganisms such as, for example, bacteria and fungi.

The compositions of the present invention, in neat form, may be directly topically applied to an area of skin in need of treatment. In various embodiments, the resulting active compound is applied directly without dilution, or alternatively, the composition can be slightly diluted with water before being applied topically. Alternatively, the active composition of the present invention can be formulated and topically applied as a spray, soap, gel, cream, lotion, ointment or the like by the addition of pharmaceutically acceptable carriers or excipients. Preferred carriers include deionised water, vegetable or mineral oils, white petrolatum, branched chain fats or oils, animal fats and high molecular weight alcohol. Emulsifiers, stabilisers and antioxidants may also be included as well as colouring agents and essential oils to impart fragrance.

It is typical that the compositions of the present invention can be formulated as a lotion or tonic, where they are either applied directly, or diluted with water and then applied. The compositions can also be formulated as creams or ointments. In such formulations the active polypeptides may be added in an amount of 10% to 60%> w/w of base moisturiser cream and mixed in with the base cream. For example, sorbolene cream or other moisturisers can have compositions of the present invention added to them in an amount of 10% to 60% w/w. Alternatively, macadamia oil, jojoba oil, almond oil or other nut and seed oils may be have the active polypeptide of the present invention added to them in an amount of 10%> to 60%> w/w.

Other topical products in which the composition of the present invention can be formulated include skin products such as creams, gels, pastes, emulsions, salves, sprays, masques and peels, and the like.

Suitable topical vehicles for use with the compositions of the present invention are well known in the pharmaceutical areas and include water, lipid bases materials including oils and fats, soaps, surfactants, emollients, skin conditioning agents and emulsifying agents. Examples of these vehicles are described Martindale—The Extra Pharmacopoeia (Pharmaceutical Press). Clearly, the choice of a suitable vehicle depends on the mode of delivery of the formulation. The active composition is generally incorporated in the dermatologically acceptable vehicle/carrier in a conventional manner well known in the pharmaceutical arts.

Topical application of an efficacious amount of the composition of the present invention to an area of skin in need of treatment affords fast and effective healing from the symptoms of various wounds such as ulcers, chronic non-healing wounds and acne. The area of treated skin takes on an improvement in that the surface area of the wound reduces in size as a percentage of the first application of the composition and preferably the area where the dermis has re-grown may have skin tone that appears smooth and taut.

Typically, a composition of the present invention is topically applied to an animal, preferably a human, for the treatment or prophylaxis of all epidermal wounds including ulcers, insect bites, first, second and third degree burns, healing of sores, wounds and skin infections. Typically, a composition of the present invention reduces scarring and reduces effects of prolific fibrosis on the epidermis. Preferably, a general improvement in clarity, skin texture and appearance of a final scar may be observed after application of a composition of the present invention compared to a similar wound where the composition is not applyed.

Typically, a formulation containing a composition of the present invention, such as a composition and a carrier and/or dilutent is topically applied to the appropriate area and allowed to remain. In various embodiments several applications may be made consequently.

Accordingly, it is typical that the topical compositions of the present invention can be in the form of a masque or lotion or gel, or a cream or ointment.

The carrier can be a solvent or dispersion medium containing, for example, water, ethariol, polyol (for example, glycerol, propylene glycol and liquid polyethylene glycol, and the like), suitable mixtures thereof, and vegetable oils. The carrier may be carboxyl methylcellulose. The proper fluidity can be maintained, for example, by the maintenance of the required particle size in the case of dispersion and by the use of surfactants. Preventing the action of microorganisms in the compositions of the invention is achieved by adding antibacterial and/or antifungal agents, for example, parabens, chlorobutanol, phenol, sorbic acid, thimerosal and the like. In many cases, it will be preferable to include isotonic agents, for example, sugars or sodium chloride. Prolonged absorption of the compositions can be brought about by the use in the compositions of agents delaying absorption, for example, aluminum monostearate and gelatin.

Sterile injectable solutions for local application may be prepared by incorporating the active compositions in the required amount in the appropriate solvent with several of the other ingredients enumerated above, as required, followed by filtered sterilization. Generally, dispersions are prepared by incorporating the various sterilized active ingredient into a sterile vehicle which contains the basic dispersion medium and the required other ingredients from those enumerated above.

The active ingredient may be held within a matrix which controls the release of the active agent. Preferably, the matrix comprises a substance selected from the group consisting of lipid, polyvinyl alcohol, polyvinyl acetate, polycaprolactone, poly(glycolic)acid, poly(lactic)acid, polycaprolactone, polylactic acid, polyanhydrides, polylactide-co-glycolides, polyamino acids, polyethylene oxide, acrylic terminated polyethylene oxide, polyamides, polyethylenes, polyacrylonitriles, polyphosphazenes, poly(ortho esters), sucrose acetate isobutyrate (S AIB), and combinations thereof and other polymers. Preferably, the matrix sustainedly releases the agonist.

Pharmaceutically acceptable carriers and/or diluents may also include any and all solvents, dispersion media, coatings, antibacterials and/or antifungals, isotonic and absorption delaying agents and the like. The carrier and/or diluents may be carboxyl methylcellulose. The use of such media and agents for pharmaceutical active substances is well known in the art. Except insofar as any conventional media or agent is incompatible with the active ingredient, use thereof in the therapeutic compositions is contemplated.

The composition may further comprising an adjunct treatment agent. In various embodiments the adjunct treatment agent may comprise a debridement agent such as papain. Preferably the polypeptide or the composition is suitable for use in the treatment of the wound site.

"Treatment" and "treat" and synonyms thereof refer to therapeutic treatment wherein the object is to speed up (increase) wound healing by reducing the size of the wound surface area in the shortest amount of time, reducing the amount of collagen in the wound site, reducing visible scarring or increased expression of nitric oxide synthase (iNOS). Treatment may include prophylactic passive treatment of a patent at the time of surgery. Those in need of such treatment include those with a wound such as a cut, an ulcer or a disruption of the skin or a chronic slow healing wound common in individuals with diabetes. An individual refers to an animal, preferably a human.

To close a wound site refers to reducing the size of the wound surface area preferably until the dermis is mostly or completely covering the area, essentially, healing the wound. Wound healing may be measured as a percentage of the reduction of the wound surface area to the initial surface area at the time of the application of the polypeptide or composition described herein.

A therapeutically effective amount would be able to increase an angiopoietin like 4 protein (ANGPTL4) polypeptide in a wound site. As used herein a "therapeutically effective amount" of a composition will be an amount of active agent that is capable of speeding up (increasing) wound healing. Dosages and administration of a composition of the invention in a pharmaceutical composition may be determined by one of ordinary skill in the art of clinical pharmacology or pharmacokinetics. An effective amount of the composition to be employed therapeutically, for example a polypeptide, will depend, for example, upon the therapeutic objectives, the route of administration, and the condition of the mammal. Accordingly, it will be necessary for the therapist to titer the dosage and modify the route of administration as required to obtain the optimal therapeutic effect. A typical daily dosage might range from about 10 ng to up to 100 mg per wound or more per day, preferably about 1 µg to 10 mg per wound. Doses may include protein amount any where in the range of 10 to 100 µg or more preferably 25, 50, or 75 µg per wound.

Preferably, the angiopoietin like 4 (ANGPTL4) polypeptide or therapeutically active fragment thereof is as described above.

Wound site, refers to a type of injury where the dermis of the skin is disrupted forming a tear, cut, puncture, incision, laceration, abrasion, rip, slash, scratch, slit or rupture in the skin of an animal. Such wounds may include ulcers such as venous ulcers, pressure ulcers or diabetic foot. Diabetic foot refers to chronic slow healing wounds on the lower limbs of an individual who may have diabetes. Preferably, the wound site is selected from an ulcer, a chronic slow-healing wound and an open wound.

Another aspect of the invention includes a method of determining whether a wound site will become a chronic slow-healing wound, comprising the steps of (a) determining the level of the angiopoietin like 4 protein (ANGPTL4) present in a sample taken from the wound site (b) comparing the level of the angiopoietin like 4 protein (ANGPTL4) from the sample with a control from a healthy individual (with normal wound healing), wherein a reduced level of ANGPLT4 in the sample compared with the control is indicative that the wound site will become a chronic slow-healing wound.

A chronic slow-healing wound refers to impaired wound healing or wounds that do not appear to follow the normal healing process in less than 4 weeks.

The method may further comprising the step of determining the blood sugar level of the individual suspected of having the chronic slow-healing wound wherein a high blood sugar level compared to the blood sugar level of a healthy individual is further indicative that the wound site will become a chronic slow-healing wound.

ANGPTL4 produced by wound keratinocytes interacts with specific matrix proteins in the wound bed, delaying their proteolytic degradation by MMPs, and directly affects cell-matrix communication by altering the availability of intact matrix proteins. Thus, the multifaceted roles of ANGPTL4 link inflammation, diabetes and wound healing.

The management of the diabetic wound is complex requiring a multidisciplinary approach. Diabetic wounds are characterized by an accumulation of devitalized tissue, chronic inflammation, poor wound-related angiogenesis and deficiencies in several ECM components. Despite the enormous medical burden from poor diabetic wound healing, effective therapies that can regenerate this corrupted ECM have been lacking.

We have showed that ANGPTL allows crosstalk of various cells such as wound keratinocytes, dermal fibroblasts, endothelial cells or inflammatory cells with the surrounding ECM thus rendering it to be more efficacious than individual cytokine-mediated candidates. We also showed that ANGPTL4 reduced collagen deposition towards the later stage of in our diabetic wound healing. Unlike PDGF, ANGPTL4 can be administered as a topical cream or via biocompatible scaffolds. ANGPTL4 can also be used as an anti-scarring agent.

Our study suggested that manipulation of ANGPTL4 may provide adjunctive or new therapeutics avenues in diabetes-associated complications, such as diabetic foot ulcers. It's anti-scarring properties could revolutionize wound healing strategy, not only by improving the healing rate but the aesthetic appearance of the skin. It can also be incorporated into over-the-counter creams, wound plasters, dressings, etc for improved healing and reduced scar formation.

EXAMPLES OF PREFERRED EMBODIMENTS

We showed that the topical application of recombinant ANGPTL4 facilitates wound healing in diabetic mice. ANGPTL4 increases the production of NO level in wounded keratinocytes via integrin β1 signaling/pSTAT3 induction of iNOS expression. The elevated NO in the wound microenvironment reduces collagen scar tissue via the stabilization of the ID3 mRNA, which inhibits the expression of COL1A2 in dermal fibroblasts. Our focused gene expression profiling also revealed that the majority of the dysregulated temporal and expression levels of cytokines, growth factors and transcription factors observed in diabetic mice wounds (ob/ob) when compared to wild type counterpart (ob/+), were restored upon treatment with ANGPTL4. Our study suggested that the replacement of ANGPTL4 provides an adjunctive or new therapeutic avenue in diabetics-associated complications, such as diabetic foot ulcers.

Example 1

Animals. Heterozygous BTBR.V (B6)-Lep$^{ob}$/WiscJ mice (+/ob) were purchased from The Jackson Laboratory (Bar Harbor, Me.). Age- and sex-matched homozygous ob/ob and wildtype (+/+) were obtained by interbreeding the +/ob littermates. At 3-wk old, offsprings were separated from their parents and genotyped using polymerase chain reaction-restriction fragment length polymorphism (PCR-RFLP). Male C57BL/6J mice$^-$ were obtained from Laboratory Animal Centre, National University of Singapore. All mice used in this study were individually caged housed in a temperature-controlled room (23° C.) on a 12 h light-dark cycle, and allowed ad libitum access to standard mouse chow diet and water. The mutant mice exhibit severe diabetic conditions from 8 weeks of age and blood glucose level of diabetic mice was 473±14.6 mg/dL and non-diabetic mice was 122.5±5.21 mg/dL as determined by Accu-Chek Advantage glucometer (Roche Diagnostic).

Example 2

Genotyping of Crossbred mice with PCR-RFLP. A small tail biopsy was collected from each mouse for genotyping and ear tagged after anesthetics. Genomic DNA was extracted using a modified Proteinase K protocol as previously described [25]. Genotyping was performed on extracted DNA using PCR-RFLP assay. Primer sequences were (5'-TGTCCAAGATGGACCAGACTC-3') (SEQ ID NO: 3) and (5'-ACTGGTCTGAGGCAGGGAGCA-3') (SEQ ID NO: 4). PCR product was digested with DdeI restriction enzyme. Digested fragments were resolved by 2% agarose gel electrophoresis. Using PCR-RFLP, +/+ mice show a single 155-bp band; heterozygous (+/ob) and homozygous mutant (ob/ob) yield 3 bands (155, 100 and 55-bp bands) and 2 bands (100 and 55-bp bands), respectively.

Example 3

Reduced ANGPTL4 expression in impaired diabetic wound healing. To demonstrate an impaired wound healing of a diabetic (ob/ob) mice compared with normal (ob/+) mice, we evaluated the progress and dynamics of wound healing of full-thickness excisional splint wounds between ob/+ and ob/ob mice.

Mice were anesthetized prior to surgery by a single intraperitoneal anaesthetized with of ketamine/xylazine (80 mg/kg+10 mg/kg). Full-thickness excisional wounds (0.5× 0.5 cm$^2$) were created on the dorso-medial back of each mouse. Mice were euthanized by $CO_2$ inhalation at Day 0, 3, 5, 7 and 10 post wounding. At the indicated time, photo imaging, histomorphometric and other biological analysis of wound biopsies was done.

Figure 1:
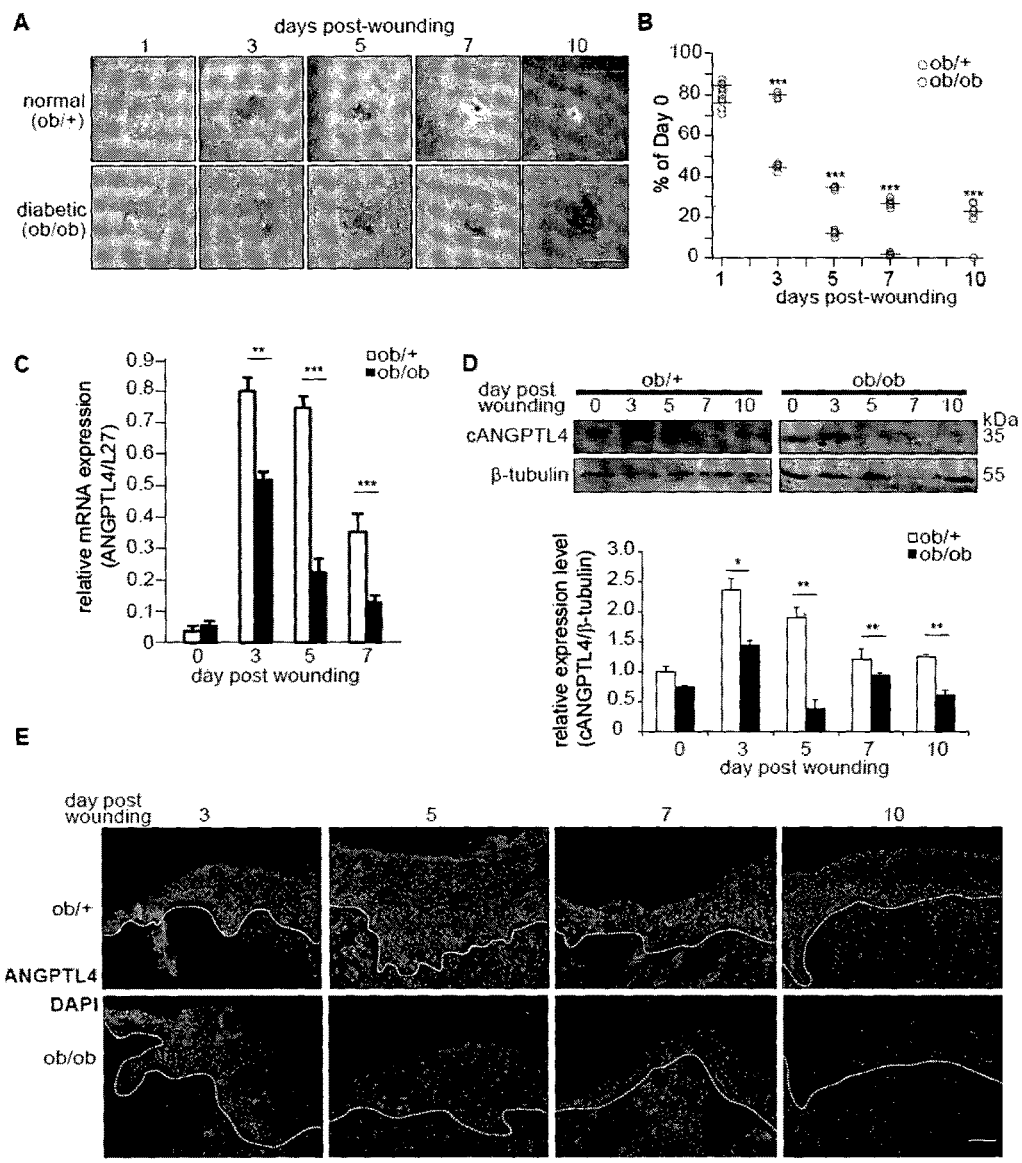
FIG. 1. Wound healing was retarded in diabetic (ob/ob) mice.

Macroscopic observation revealed that ob/ob mice closed 40% of the wound when compared to the ob/+ mice which had complete wound closure by day 10 post-injury (FIG. 1A). Haematoxylin and eosin (H&E) staining of day 3, 5, 7 and 10 post-injury biopsies showed impaired epithelial regeneration and granulation tissue formation in ob/ob when compared to ob/+ mice. Complete re-epithelialization of ob/+ wounds was observed on day 7 post-injury (FIG. 6A).

Wound biopsies were fixed in 4% paraformaldehyde-PBS overnight at 4° C., embedded in OCT tissue freezing medium (Leica) and frozen immediately with liquid nitrogen. Cryosections of 8 μm thickness were used for histological staining. Histomorphometric analysis of centrally dissected ob/ob wound sections revealed significantly delayed re-epithelialization between day 3-10 post-wounding (ob/+ versus ob/ob: Day 3, 52.1% vs. 79.6%, p<0.01; Day 5, 13.3% vs. 35.4%, p<0.01; Day 7, 3.0% vs. 28.6%, p<0.01; Day 10, 0% vs. 23.6%, p<0.01; FIG. 1B and FIG. 6B). The epidermal wound area above the wound bed of the ob/ob mice remained larger compared with ob/+ mice on day 10 post-injury (11.8×10$^5$ vs. 2×10$^5$ μm$^2$, p<0.01; FIG. 6C), suggesting delayed resolution of the wound re-epithelialization in ob/ob mice.

ANGPTL4 is important for the healing of normal full-thickness excision wound. ANGPTL4-deficient mice showed a delay in wound healing associated with perturbed keratinocyte migration, poor wound-related angiogenesis that is highly reminiscent of diabetic wound healing. To investigate the role of ANGPTL4 in a diabetic wound, we first compared the spatiotemporal expression profile of ANGPTL4 mRNA and protein between wounded ob/ob mice and ob/+ mice.

RNA extraction and reverse transcription. At indicated time, skin wound biopsies were excised as previously described [26] and total RNA was extracted using Illustra RNAspin Mini (GE Healthcare) following the supplier's protocol. Five μg of total RNA was reverse transcribed with oligo-dT primers using RevertAid™ H Minus M-MuLV. The RNAs were removed by RNase H digestion prior quantitative real-time PCR (qPCR). Total RNA was isolated from archival paraformaldehyde-fixed, paraffin embedded sections (FFPE) of human diabetic wounds using Recover-All™ total nucleic acid isolation (Ambion). Fifty ng of RNA was subjected to Full Spectrum™ Complete Transcriptome RNA Amplification (System Biosciences) according to manufacturer's recommendation prior qPCR. The quantitative real-time PCR (qPCR) analyses revealed ~2-folds reduction in ANGPTL4 expression from day 3 post wounding in ob/ob mice compared with ob/+ mice (ob/ob vs ob/+: Day 3, 0.790 vs. 0.511, p<0.01; Day 5, 0.735 vs. 0.222, p<0.01; Day 7, 0.359 vs. 0.164, p<0.01; FIG. 1C).

Wound biopsies were homogenized with ice-cold protein lysis buffer pH 8.0 (20 mM $Na_2H_2PO_4$, 250 mM NaCl, 1% Triton X-100, 0.1% SDS and 1 mM PMSF). Total protein lysates were precipitated by a chloroform/methanol solvent method prior been resolved on 10% SDS-PAGE. The proteins were electrotransferred onto a onto polyvinylidene fluoride membrane (Millipore). The membranes were blocked with 5% skim milk in TBS (0.25 M Tris.HCl, pH 7.6, 1.5 M NaCl) containing 0.05% Tween-20. The membrane was incubated with indicated primary antibodies overnight at 4° C. and appropriate anti IgG-HRP secondary antibodies (1:10000) for 1 h at room temperature. The protein bands were revealed using Immobilon™ Western Chemiluminescent HRP Substrate (Millipore) and signals were quantified by densitometry with the aid of ImageJ version 1.38x (NIH). Consistent with qPCR data, the western blot analysis showed a ~5-fold reduction in the level of ANGPTL4 at day 5 post wounding in ob/ob mice as compared with ob/+(ob/ob vs ob/+; Day 3, 2.36 vs. 1.43, p<0.05; Day 5, 1.90 vs. 0.38, p<0.01; Day 7, 1.21 vs. 0.93, p<0.01; Day 10, 1.25 vs. 0.62, p<0.01; FIG. 1D).

Similarly, the immunofluorescence staining of day 3-10 wound biopsies of ob/ob mice revealed a lower expression of ANGPTL4 in the wound epithelia and wound bed when compared with ob/+(FIG. 1E). Wound biopsies were fixed in 4% paraformaldehyde-PBS overnight at 4° C., embedded in OCT tissue freezing medium (Leica) and frozen immediately with liquid nitrogen. Cryosections of 8 μm thickness were used for immunofluorescence staining as previously described [26] except that Alexa488- or Alexa594-conjugated secondary antibodies were used. Apoptotic cells were detected using the TUNEL assay according to the manufacturer's recommendation (Roche). As positive control for TUNEL assay, the section was pre-treated with DNase I. The slides were counterstained with DAPI (Vectashield) and images capture using Eclipse TE2000-U microscope (Nikon).

Example 4

Topical application of cANGPTL4 improves the healing rate of diabetic wounds. Next, we examined the effect of topical application of recombinant ANGPTL4 on the rate of diabetic wound healing. We inflicted two full excisional splint wounds on the dorsal surface of DB mice, and treated one wound with cANGPTL4 and the other with saline in 4% carboxymethylcellulose (FIG. 7A).

Two circular 5 mm diameter full excisional wounds were created on the dorso-media back of each mouse and silicon donut-shaped splints of 10 mm diameter were centered over the wounds. The silicon splint was adhered to the skin with cyanoacrylate glue. On the day of surgery (day 0), 50 μL of recombinant human ANGPTL4 (rhANGPTL4) protein of 1 mg/mL or 2 mg/mL or PBS mixed with 1% carboxyl methylcellulose (CMC) was applied topically to their respective cutaneous wound and protected with an occlusive dressing (Tegaderm, 3M) throughout the duration of the study.

The wound images revealed a distinct improvement in the wound closure of cANGPTL4-treated ob/ob mice compared to saline-treated ob/ob mice on day 7 and 10 post-injury (FIG. 7B). Histomorphological examination of sections obtained as described in Example 3, from wounds harvested on indicated days showed that cANGPTL4 significantly accelerated re-epithelialization compared with saline control, as indicated by the reduced epithelial gap (saline- vs. cANGPTL4-treated; Day 3, 76.2% vs. 60.1%, p<0.05; Day 5, 34.3% vs. 28.1%, p<0.05; Day 7, 25.6% vs. 4.6%, p<0.01; Day 10, 20.3% vs 0%, p<0.01; FIG. 2A and FIG. 7C). ANGPTL4-treated wounds showed a significant reduction in the overall epidermal wound area on day 7-10 compared with saline control ($3.6 \times 10^5$ vs. $6.0 \times 10^5$ μm², p<0.01; FIG. 7D).

The dysregulation of growth factors and cytokines production, and subsequent aberrant activation of signaling cascades contribute to poor diabetic wound healing. These factors and signaling mediators are known to be integral in the chemotaxis, migration, stimulation, and proliferation of cells and matrix substances necessary for wound healing. To investigate if treatment of diabetic wound with ANGPTL4 can affect the expression profiles of various genes involved several biological aspect of wound healing, focused qPCR arrays were performed on wound biopsies derived from ob/+, ob/ob and ob/ob mice treated with ANGPTL4 at various days post-wounding.

We analysed a total of 79 genes, whose temporal expression profile during wound healing can be clustered into their biological function such as proliferation, angiogenesis, cell migration, extracellular matrix (ECM), cell apoptosis and inflammation (FIG. 2B). Real-time PCR arrays were used to analyze the expression of a focused panel of genes. qPCR was performed with KAPA™ SYBR qPCR Universal Master Mix (KAPABiosystems). Melt curve analysis was included to assure that only one PCR product was formed. Primers were designed to generate a PCR amplification product of 100 to 250 bp. Only primer pairs yielding unique amplification products without primer dimer formation were subsequently used for real-time PCR assays. Expression was related to the control gene ribosomal protein P0 (RPLP0), which did not change under any of the experimental conditions studied. The sequences of qPCR primers are available in Table 1.

TABLE 1

List of primer pairs sequences.

| Genes | Sequence (5' to 3') | Sequence (5' to 3') |
|---|---|---|
| ADAM metallopeptidase domain 9 (ADAM9) | F: GGACGGAACCAGACTGCTG (SEQ ID NO: 5) | R: CCACTGAACAAAGTTGCCCA (SEQ ID NO: 6) |
| Adiponectin (ADIPOQ) | F: AGCCGCTTATATGTATCGCTCA (SEQ ID NO: 7) | R: TGCCGTCATAATGATTCTGTTGG (SEQ ID NO: 8) |
| AKT1 | F: CCAAGGCCCAACACCTTTATC (SEQ ID NO: 9) | R: TTCCTGCCTCTTGAGTCCATC (SEQ ID NO: 10) |

TABLE 1-continued

List of primer pairs sequences.

| Genes | Sequence (5' to 3') | Sequence (5' to 3') |
|---|---|---|
| ANGPT1 | F: TGCACTAAAGAAGGTGTTTTGCT (SEQ ID NO: 11) | R: CCTCCCCCATTCACATCCATATT (SEQ ID NO: 12) |
| ANGPT2 | F: CGAGGCGCATTCGCTGTAT (SEQ ID NO: 13) | R: GGCTGATGCTACTTATTTTGCCC (SEQ ID NO: 14) |
| ANGPTL4 | F: TCCAACGCCACCCACTTAC (SEQ ID NO: 15) | R: TGAAGTCATCTCACAGTTGACCA (SEQ ID NO: 16) |
| CCL2 | F: TTAAAAACCTGGATCGGAACCAA (SEQ ID NO: 17) | R: GCATTAGCTTCAGATTTACGGGT (SEQ ID NO: 18) |
| CCL11 | F: GAATCACCAACAACAGATGCAC (SEQ ID NO: 19) | R: ATCCTGGACCCACTTCTTCTT (SEQ ID NO: 20) |
| Cyclin-dependent kinase 4 (CDK4) | F: CCAATGTTGTACGGCTGATGG (SEQ ID NO: 21) | R: TGTCCAGGTATGTCCTCAGGT (SEQ ID NO: 22) |
| Cyclin-dependent kinase inhibitor 2B (CDKN2B) | F: CCCTGCCACCCTTACCAGA (SEQ ID NO: 23) | R: CAGATACCTCGCAATGTCACG (SEQ ID NO: 24) |
| cystatin A (CSTA) | F: TACGGAGGTGTTTCAGAGGC (SEQ ID NO: 25) | R: CAGCGACGGCTTGAGTTTT (SEQ ID NO: 26) |
| CXCL1 | F: CTGGGATTCACCTCAAGAACATC (SEQ ID NO: 27) | R: CAGGGTCAAGGCAAGCCTC (SEQ ID NO: 28) |
| CXCL5 | F: TGCGTTGTGTTTGCTTAACCG (SEQ ID NO: 29) | R: AGCTATGACTTCCACCGTAGG (SEQ ID NO: 30) |
| CXCL9 | F: GAACGGAGATCAAACCTGCCT (SEQ ID NO: 31) | R: TGTAGTCTTCCTTGAACGACGA (SEQ ID NO: 32) |
| CXCL10 | F: CCAAGTGCTGCCGTCATTTTC (SEQ ID NO: 33) | R: GGCTCGCAGGGATGATTTCAA (SEQ ID NO: 34) |
| Epidermal growth factor receptor (EGFR) | F: GGGAGCATTTGGCACAGTGTA (SEQ ID NO: 35) | R: GCCATCACATAGGCTTCGTCAA (SEQ ID NO: 36) |
| EPHA3 | F: TTCTGGTCGGGAGGTTTTGTG (SEQ ID NO: 37) | R: ACTGCTTGAGTAGGGTCTTCA (SEQ ID NO: 38) |
| EPHB3 | F: ACCGTAAGAGACTGTAACAGCA (SEQ ID NO: 39) | R: GTCCACTTTCACGTAGGGGTT (SEQ ID NO: 40) |
| Fatty acid synthase (FAS) | F: AGAGATCCCGAGACGCTTCT (SEQ ID NO: 41) | R: GCCTGGTAGGCATTCTGTAGT (SEQ ID NO: 42) |
| Fibroblast growth factor 1 (FGF1) | F: CAGCTCAGTGCGGAAAGTG (SEQ ID NO: 43) | R: TGTCTGCGAGCCGTATAAAAG (SEQ ID NO: 44) |
| FGF2 | F: GCGACCCACACGTCAAACTA (SEQ ID NO: 45) | R: TCCATCTTCCTTCATAGCAAGGT (SEQ ID NO: 46) |
| FBJ osteosarcoma oncogene B (FOSB) | F: GCCACTGCCGACCACAATTC (SEQ ID NO: 47) | R: TTATTGGCGACAGTGCAGAACC (SEQ ID NO: 48) |
| Fos related antigen 2 (FRA2) | F: AGCCTCCCGAAGAGGACAG (SEQ ID NO: 49) | R: AGGACATTGGGGTAGGTGAA (SEQ ID NO: 50) |
| Growth differentiation factor 3 (GDF3) | F: TAAGGTGGGCAGATTGCTTTTT (SEQ ID NO: 51) | R: CTGGACAGTTACCCTGGAGTA (SEQ ID NO: 52) |
| GLI-Kruppel family member GLI1 (GLI1) | F: GAGCCCTTCTTTAGGATTCCCA (SEQ ID NO: 53) | R: ACCCCGAGTAGAGTCATGTGG (SEQ ID NO: 54) |
| GM-CSF | F: TCGTCTCTAACGAGTTCTCCTT (SEQ ID NO: 55) | R: GCAGTATGTCTGGTAGTAGCTGG (SEQ ID NO: 56) |
| Hepatocyte growth factor (HGF) | F: CTGCTTCATGTCGCCATCC (SEQ ID NO: 57) | R: TGGGTCTTCCTTGGTAAGAGTAG (SEQ ID NO: 58) |
| HIF1α | F: GGTCATCGCAGTTGGAACCTC (SEQ ID NO: 59) | R: CGCTTGTGTCTTGGAAGGCTTG (SEQ ID NO: 60) |

TABLE 1-continued

List of primer pairs sequences.

| Genes | Sequence (5' to 3') | Sequence (5' to 3') |
|---|---|---|
| Baculoviral IAP repeat-containing 2 (IAP2) | F: AGGGACCATCAAGGGCACAG (SEQ ID NO: 61) | R: TTTGTGTGTTTGGCGGTGTCTC (SEQ ID NO: 62) |
| Insulin-like growth factor binding protein 4 (IGFBP4) | F: AGAAGCCCCTGCGTACATTG (SEQ ID NO: 63) | R: TGTCCCCACGATCTTCATCTT (SEQ ID NO: 64) |
| IL1R1 | F: GCCAAGGTGGAGGACTCAG (SEQ ID NO: 65) | R: CCAGGGTCATTCTCTAACACAGT (SEQ ID NO: 66) |
| IL-6 | F: TAGTCCTTCCTACCCCAATTTCC (SEQ ID NO: 67) | R: TTGGTCCTTAGCCACTCCTTC (SEQ ID NO: 68) |
| IL-10 | F: AGAAGCATGGCCCAGAAATCA (SEQ ID NO: 69) | R: GGCCTTGTAGACACCTTGGT (SEQ ID NO: 70) |
| IL-18 | F: GTGAACCCCAGACCAGACTG (SEQ ID NO: 71) | R: CCTGGAACACGTTTCTGAAAGA (SEQ ID NO: 72) |
| Inhibin, beta A (INHBA) | F: ATAGAGGACGACATTGGCAGG (SEQ ID NO: 73) | R: ATAGAGGACGACATTGGCAGG (SEQ ID NO: 74) |
| Integrin, alpha V (ITGAV) | F: CCTGTGCTCCATTGTACCACT (SEQ ID NO: 75) | R: AGCATACTCAACGGTCTTTGTG (SEQ ID NO: 76) |
| Jun B proto-oncogene (JUN-B) | F: GACCTGCACAAGATGAACCAC (SEQ ID NO: 77) | R: AGGCTGGAGAGTAACTGCTGA (SEQ ID NO: 78) |
| Keratinocyte growth factor (KGF) | F: CCGTGGCAGTTGGAATTGTG (SEQ ID NO: 79) | R: CCTCCGCTGTGTGTCCATTT (SEQ ID NO: 80) |
| KI67 | F: CTGCCTCAGATGGCTCAAAGA (SEQ ID NO: 81) | R: GAAGACTTCGGTTCCCTGTAAC (SEQ ID NO: 82) |
| Kruppel-like factor 9 (KLF9) | F: GCCGCCTACATGGACTTCG (SEQ ID NO: 83) | R: GCCGTTCACCTGTATGCAC (SEQ ID NO: 84) |
| Mitogen-activated protein kinase 3 (MAPK3 (1B)) | F: ACCACATTCTAGGTATCTTGGGT (SEQ ID NO: 85) | R: GATGCGCTTGTTTGGGTTGAA (SEQ ID NO: 86) |
| Mitogen-activated protein kinase kinase kinase kinase 1 (MAP4K1) | F: CTCACAGCTCGCTCAGATCC (SEQ ID NO: 87) | R: GAGGGGACAGCCGTTGAAT (SEQ ID NO: 88) |
| Melan-a (MLANA) | F: TGGATACAGAACCTTGATGGACA (SEQ ID NO: 89) | R: GGGCTGATGGGATTTCTCTTG (SEQ ID NO: 90) |
| MMP9 | F: AAACCACCTCTCCCGACTCCAG (SEQ ID NO: 91) | R: AGCTCGGTGGTGTTCTCCAATG (SEQ ID NO: 92) |
| MMP13 | F: ACCTCCACAGTTGACAGGCT (SEQ ID NO: 93) | R: AGGCACTCCACATCTTGGTTT (SEQ ID NO: 94) |
| OPN | F: ATCTCACCATTCGGATGAGTCT (SEQ ID NO: 95) | R: TCAGTCCATAAGCCAAGCTATCA (SEQ ID NO: 96) |
| PAI1 | F: GTGCATCACTCCACAAACCTGC (SEQ ID NO: 97) | R: TAACGTGGGTTGCCAAGCATC (SEQ ID NO: 98) |
| PDGFA | F: CGCTGCACTGGCTGTTGTA (SEQ ID NO: 99) | R: TTCCCTACGCCTTCCTGTCTC (SEQ ID NO: 100) |
| PDGFB | F: CGAGCCAAGACGCCTCAAG (SEQ ID NO: 101) | R: CATGGGTGTGCTTAAACTTTCG (SEQ ID NO: 102) |
| Platelet and Endothelial Cell Adhesion Molecule 1 (PECAM1) | F: TGCACCCCATCACTTACCACC (SEQ ID NO: 103) | R: TAAAACGCGGTCCTGTTCCTC (SEQ ID NO: 104) |
| PPARα | F: TCGGCGAACTATTCGGCTG (SEQ ID NO: 105) | R: GCACTTGTGAAAACGGCAGT (SEQ ID NO: 106) |
| PPARβ1δ | F: TTGAGCCCAAGTTCGAGTTTG (SEQ ID NO: 107) | R: CGGTCTCCACACAGAATGATG (SEQ ID NO: 108) |
| PPARγ | F: TGTGGGGATAAAGCATCAGGC (SEQ ID NO: 109) | R: CCGGCAGTTAAGATCACACCTAT (SEQ ID NO: 110) |

TABLE 1-continued

List of primer pairs sequences.

| Genes | Sequence (5' to 3') | Sequence (5' to 3') |
|---|---|---|
| Ras homolog gene family, member A (RHOA) | F: AGCCTTTCTCACCTGGACTGC (SEQ ID NO: 111) | R: CACCCACTGCCACCCATAAG (SEQ ID NO: 112) |
| RpI27 | F: CAAGGGGATATCCACAGAGTACCTT (SEQ ID NO: 113) | R: CTGGTGGCTGGAATTGACCGCTA (SEQ ID NO: 114) |
| SKI-like oncogene (SKIL) | F: AGGCAGAGACAAGTAAGTCCA (SEQ ID NO: 115) | R: CGTCTGGGTAAGACACTGTTTTT (SEQ ID NO: 116) |
| SMAD3 | F: CCCCCACTGGATGACTACAG (SEQ ID NO: 117) | R: TCCATCTTCACTCAGGTAGCC (SEQ ID NO: 118) |
| SOCS1 | F: CTGCGGCTTCTATTGGGGAC (SEQ ID NO: 119) | R: AAAAGGCAGTCGAAGGTCTCG (SEQ ID NO: 120) |
| SOCS3 | F: CAAGAACCTACGCATCCAGTG (SEQ ID NO: 121) | R: CCAGCTTGAGTACACAGTCGAA (SEQ ID NO: 122) |
| SPARC | F: ACTACATCGGACCATGCAAATAC (SEQ ID NO: 123) | R: GTACAAGGTGACCAGGACATTTT (SEQ ID NO: 124) |
| STAT1 | F: GGAGCACGCTGCCTATGATG (SEQ ID NO: 125) | R: CTCCAGAGAAAAGCGGCTGTA (SEQ ID NO: 126) |
| STAT3 | F: CAATACCATTGACCTGCCGAT (SEQ ID NO: 127) | R: GAGCGACTCAAACTGCCCT (SEQ ID NO: 128) |
| STAT5A | F: AGTGGTTCGACGGGGTGAT (SEQ ID NO: 129) | R: ATGGCTTCAGATTCCAGAGGT (SEQ ID NO: 130) |
| TGFα | F: CACTCTGGGTACGTGGGTG (SEQ ID NO: 131) | R: CACAGGTGATAATGAGGACAGC (SEQ ID NO: 132) |
| TGFβ1 | F: CCGCAACAACGCCATCTATG (SEQ ID NO: 133) | R: CTCTGCACGGGACAGCAAT (SEQ ID NO: 134) |
| TGFβ2 | F: TCGACATGGATCAGTTTATGCG (SEQ ID NO: 135) | R: CCCTGGTACTGTTGTAGATGGA (SEQ ID NO: 136) |
| TGFβ receptor 1 (TGFβR1) | F: TCCCAACTACAGGACCTTTTCA (SEQ ID NO: 137) | R: GCAGTGGTAAACCTGATCCAGA (SEQ ID NO: 138) |
| TIMP1 | F: CTTGGTTCCCTGGCGTACTC (SEQ ID NO: 139) | R: ACCTGATCCGTCCACAAACAG (SEQ ID NO: 140) |
| TIMP2 | F: CTGGACGTTGGAGGAAAGAAG (SEQ ID NO: 141) | R: GGTGATGCTAAGCGTGTCCC (SEQ ID NO: 142) |
| TIMP3 | F: GCGCAAGGGCCTCAATTAC (SEQ ID NO: 143) | R: AGAGACACTCATTCTTGGAGGT (SEQ ID NO: 144) |
| TLR2 | F: CCAGACACTGGGGGTAACATC (SEQ ID NO: 145) | R: CGGATCGACTTTAGACTTTGGG (SEQ ID NO: 146) |
| TLR4 | F: AAAGTGGCCCTACCAAGTCTC (SEQ ID NO: 147) | R: TCAGGCTGTTTGTTCCCAAATC (SEQ ID NO: 148) |
| TNC | F: GCTACCGACGGGATCTTCG (SEQ ID NO: 149) | R: TAGCCGTGGTACTGATGGTTT (SEQ ID NO: 150) |
| TNFα | F: GGCTTTCCGAATTCACTGGAG (SEQ ID NO: 151) | R: CCCCGGCCTTCCAAATAAA (SEQ ID NO: 152) |
| TNFα interacting protein 2 (TNFαIP2) | F: AAAGGGATACCTACTTGCTGCT (SEQ ID NO: 153) | R: CAAGCCCGACACCTTGAAG (SEQ ID NO: 154) |
| TSP-1 | F: GAAGCAACAAGTGGTGTCAGT (SEQ ID NO: 155) | R: ACAGTCTATGTAGAGTTGAGCCC (SEQ ID NO: 156) |
| VEGFA | F: GCACATAGAGAGAATGAGCTTCC (SEQ ID NO: 157) | R: CTCCGCTCTGAACAAGGCT (SEQ ID NO: 158) |

TABLE 1-continued

List of primer pairs sequences.

| Genes | Sequence (5' to 3') | Sequence (5' to 3') |
|---|---|---|
| VG1 related sequence (VGR) | F: TCCTTGAACCGCAAGAGTCTC (SEQ ID NO: 159) | R: CTCACCCTCAGGAATCTGGG (SEQ ID NO: 160) |
| VHL | F: AAAGAGCGGTGCCTTCAGG (SEQ ID NO: 161) | R: CACTTGGGTAGTCCTCCAAATC (SEQ ID NO: 162) |
| X-ray repair complementing defective repair in Chinese hamster cells 1 (XRCC1) | F: TCTTCAGTCGTATCAACAAGACG (SEQ ID NO: 163) | R: GTTTGCTGGGAGGTTTCCTG (SEQ ID NO: 164) |

Heatmaps were constructed from the qPCR focused array data (table 2, 3 and 4) for comparison (FIG. 2B). Our analysis revealed that 18 genes out of the possible 79 (~22.7%), among them were mostly genes associated with angiogenesis and inflammation, had reverted back to ob/+ gene profiling in the ob/ob treated with cANGPTL4 (FIG. 2C).

TABLE 2

Gene expression in ob/+wound

| GenBank Accession No. | Symbol | Gene Description | Day 0 | Day 3 | Day 5 | Day 7 |
|---|---|---|---|---|---|---|
| NM_021274.1 | CXCL10 | chemokine (C-X-C motif) ligand 10 | 0.091558 | 2.265794 | 0.299061 | 0.121755 |
| NM_009283 | STAT 1 | signal transducer and activator of transcription 1 | 0.762617 | 1.325453 | 1.484704 | 0.605908 |
| NM_008808.3 | PDGFA | platelet derived growth factor, alpha | 1.034881 | 1.46755 | 2.094767 | 0.580995 |
| BC109135 | IL1R1 | interleukin 1 receptor, type I | 0.496046 | 1.924439 | 1.098497 | 0.982171 |
| NM_011577.1 | TGFB1 | transforming growth factor, beta 1 | 0.208501 | 2.552748 | 0.930714 | 0.555158 |
| NM_008402 | ITGAV | integrin alpha V | 0.846653 | 1.623685 | 1.197204 | 1.11023 |
| NM_011905 | TLR2 | toll-like receptor 2 | 0.503839 | 2.670658 | 0.809051 | 0.342864 |
| NM_011333.3 | CCL2 | chemokine (C-C motif) ligand 2 | 0.086708 | 1.764824 | 1.228643 | 0.195532 |
| NM_008279.2 | MAP4K1 | mitogen-activated protein kinase kinase kinase kinase 1 | 0.520385 | 0.820073 | 0.924272 | 0.432847 |
| NM_009532 | XRCC1 | x-ray repair complementing defective repair in Chinese hamster cells 1 | 0.409888 | 4.198295 | 1.129176 | 1.564693 |
| NM_011593 | TIMP1 | tissue inhibitor of metalloproteinase 1 | 0.097499 | 4.77994 | 0.615597 | 0.657043 |
| NM_010548.2 | IL-10 | interleukin 10 | 0.020473 | 1.212068 | 1.264306 | 0.534042 |
| NM_010431 | HIF1A | hypoxia inducible factor 1, alpha subunit | 0.7528 | 2.806556 | 1.038764 | 0.718689 |
| NM_008599.4 | CXCL9 | chemokine (C-C motif) ligand 9 | 0.345309 | 0.727598 | 1.372522 | 0.509822 |
| NM_009141.2 | CXCL5 | chemokine (C-X-C motif) ligand 5 | 0.149996 | 3.936088 | 1.464851 | 0.594453 |
| NM_007707 | SOCS3 | Suppressor of cytokine signaling 3 | 0.526876 | 4.127815 | 1.742194 | 0.582746 |
| NM_009507.3 | VHL | von Hippel-Lindau tumor suppressor | 1.001643 | 1.742515 | 1.298497 | 0.697237 |
| NM_009263 | OPN (Spp1) | secreted phosphoprotein 1 | 0.159337 | 3.38626 | 4.407381 | 0.200014 |
| NM_013693 | TNFA | Tumor necrosis factor, alpha | 0.037312 | 10.2316 | 0.468858 | 0.201943 |
| NM_008176 | CXCL1 | chemokine (C-X-C motif) ligand 1 | 0.083437 | 11.05786 | 0.793785 | 0.412259 |
| NM_009652.3 | AKT1 | thymoma viral proto-oncogene 1 | 0.594666 | 3.446702 | 1.482059 | 1.029804 |
| NM_020581.2 | ANGPTL4 | angiopoietin-like 4 | 0.03546 | 0.790093 | 0.735691 | 0.349754 |
| NM_011057.3 | PDGFB | platelet derived growth factor, B polypeptide | 0.938039 | 1.825587 | 1.79318 | 0.734739 |
| NM_001081117.2 | Ki67 | antigen identified by monoclonal antibody Ki 67 | 0.588614 | 5.438939 | 2.334188 | 3.044264 |
| NM_010427.4 | HGF | hepatocyte growth factor | 0.291696 | 1.172812 | 1.299929 | 0.511323 |
| AF016189.1 | Smad3 | MAD homolog 3 | 0.661817 | 1.268314 | 1.040053 | 0.561323 |
| NM_010143 | EPHB3 | Eph receptor B3 | 0.529828 | 0.904733 | 1.098044 | 1.303584 |
| NM_008037 | FOSL2 (FRA2) | fos-like antigen 2 | 0.304307 | 2.714392 | 0.578645 | 1.117775 |
| NM_010140 | EPHA3 | Eph receptor A3 | 0.171504 | 1.410735 | 1.281664 | 0.694695 |
| NM_207655 | EGFR | epidermal growth factor receptor | 0.664681 | 1.006642 | 0.765933 | 0.826478 |
| NM_009505 | VEGFA | vascular endothelial growth factor A | 1.256536 | 4.690086 | 2.205454 | 0.986008 |
| NM_009870 | CDK4 | cyclin-dependent kinase 4 | 0.63752 | 1.941299 | 1.289818 | 1.160359 |
| NM_007556 | BMP6 | bone morphogenetic protein 6 | 1.221781 | 2.120903 | 0.357451 | 0.136682 |
| NM_001033239 | CSTA | Cystatin A | 0.188826 | 4.410111 | 19.62685 | 6.133511 |

TABLE 2-continued

Gene expression in ob/+wound

| GenBank Accession No. | Symbol | Gene Description | Day 0 | Day 3 | Day 5 | Day 7 |
|---|---|---|---|---|---|---|
| NM_008108 | GDF3 | growth differentiation factor 3 | 0.229432 | 6.458987 | 2.496683 | 1.439967 |
| NM_011386.2 | SKIL (SnoN) | Ski like | 0.933885 | 6.077622 | 5.291099 | 2.646154 |
| NM_008416 | JUN-B | Jun-B oncogene | 0.156725 | 6.554231 | 0.686169 | 0.660104 |
| NM_008380 | INHBA | Inhibin, beta A | 0.182848 | 3.492547 | 1.07148 | 0.774788 |
| NM_009896 | SOCS1 | suppressor of cytokine signaling 1 | 0.75182 | 2.01507 | 2.614084 | 0.980315 |
| NM_021297 | TLR4 | toll-like receptor 4 | 0.503916 | 1.382422 | 1.054945 | 0.449261 |
| NM_007404 | ADAM9 | a disintegrin and metallopeptidase domain 9 | 0.395403 | 1.213515 | 0.922171 | 0.414878 |
| NM_008607 | MMP13 | matrix metallopeptidase 13 | 0.23244 | 1.656137 | 0.666829 | 0.152405 |
| NM_008871 | PAI1 (Serpine 1) | serine (or cysteine) peptidase inhibitor, clade E, member 1 | 1.71784 | 0.88462 | 0.889975 | 0.345461 |
| NM_013599 | MMP9 | matrix metallopeptidase 9 | 0.531998 | 4.645245 | 6.016101 | 1.260028 |
| NM_007426.3 | ANGPT2 | angiopoietin 2 | 0.110251 | 0.61129 | 1.77125 | 0.371325 |
| NM_011607 | TNC | tenascin C | 0.338232 | 4.641325 | 7.72361 | 5.58079 |
| NM_031168.1 | IL-6 | interleukin 6 | 0.366964 | 1.705026 | 2.175877 | 0.588519 |
| NM_011580 | TSP-1 | thrombospondin 1 | 0.476082 | 2.211606 | 1.336181 | 1.212617 |
| NM_011145.3 | PPARβ/δ | peroxisome proliferator activated receptor beta/delta | 0.858071 | 0.998435 | 1.025421 | 1.068006 |
| NM_009242 | SPARC | secreted acidic cysteine rich glycoprotein | 0.480204 | 0.790912 | 1.80714 | 0.794548 |
| NM_031199.3 | TGFA | transforming growth factor, alpha | 1.10904 | 2.309913 | 2.735879 | 1.88485 |
| NM_007670.4 | p15 (CDKN2B) | cyclin-dependent kinase inhibitor 2B | 0.86872 | 1.674337 | 1.06653 | 1.406527 |
| NM_009969.4 | GM-CSF | Colony stimulating factor 2 | 1.305664 | 0.628033 | 1.980158 | 0.103102 |
| NM_009370.2 | TGFBR1 (ALK5) | transforming growth factor, beta receptor I | 0.968227 | 0.932627 | 0.91463 | 1.035229 |
| NM_010296.2 | GLI1 | GLI-Kruppel family member GLI1 | 1.502637 | 0.463211 | 0.562287 | 0.518731 |
| NM_029993.1 | Mlana | melan-A | 0.366231 | 0.608786 | 0.160862 | 0.869004 |
| NM_009640.3 | ANGPT1 | angiopoietin 1 | 0.312981 | 0.223352 | 0.185313 | 0.194421 |
| NM_008816.2 | PECAM1 | platelet/endothelial cell adhesion molecule 1 | 1.588275 | 0.80874 | 0.777321 | 0.542357 |
| NM_010638 | KLF-9 | Kruppel-like factor 9 | 0.68505 | 0.86225 | 0.386243 | 0.307509 |
| NM_011330.3 | CCL11 | chemokine (C-C motif) ligand 11 | 0.529826 | 0.320064 | 0.593788 | 0.211562 |
| NM_008008.4 | KGF (FGF7) | fibroblast growth factor 7 | 0.514706 | 1.121522 | 0.805334 | 0.499904 |
| NM_007987.2 | FAS | Fas (TNF receptor superfamily member 6) | 0.208006 | 0.226172 | 0.034424 | 0.357528 |
| NM_011488 | STAT 5A | signal transducer and activator of transcription 5A | 0.453144 | 0.918977 | 0.756884 | 0.516671 |
| NM_008036 | FOSB | FBJ osteosarcoma oncogene B | 0.844083 | 1.618836 | 0.867265 | 0.398194 |
| BC003806 | STAT 3 | signal transducer and activator of transcription 3 | 0.704101 | 1.526852 | 1.145983 | 0.598204 |
| NM_011952 | MAPK3 (1b) | mitogen-activated protein kinase 3 | 0.3517 | 1.10514 | 0.604718 | 0.454422 |
| NM_007464 | IAP2 | intracisternal A particle 2 | 0.665846 | 1.51123 | 1.13886 | 0.551961 |
| NM_008360.1 | IL-18 | interleukin 18 | 0.366857 | 0.606514 | 0.960225 | 0.558545 |
| NM_010517 | IGFBP4 | insulin-like growth factor binding protein 4 | 0.614106 | 0.888844 | 0.794956 | 0.476489 |
| NM_009396.2 | TNFAIP2 | tumor necrosis factor, alpha-induced protein 2 | 0.906535 | 0.835809 | 0.654888 | 0.250271 |
| NM_016802 | RHOA | ras homolog gene family, member A | 0.981261 | 0.993775 | 0.959051 | 0.495424 |
| NM_008006.2 | FGF2 | fibroblast growth factor 2 | 0.424226 | 0.758342 | 0.404547 | 0.155131 |
| NM_009367.3 | TGFB2 | transforming growth factor, beta 2 | 1.28443 | 0.576548 | 0.736159 | 0.443463 |
| NM_011594 | TIMP2 | tissue inhibitor of metalloproteinase 2 | 0.497669 | 0.489931 | 1.041379 | 0.386715 |
| NM_010197.3 | FGF1 | fibroblast growth factor 1 | 1.506516 | 0.845095 | 0.630055 | 0.504144 |
| NM_011595.2 | TIMP3 | tissue inhibitor of metalloproteinase 3 | 0.896732 | 0.560416 | 0.344548 | 0.387725 |
| NM_011144.6 | PPARα | peroxisome proliferator activated receptor alpha | 1.376648 | 0.632694 | 0.50422 | 0.457501 |
| NM_001127330.1 | PPARγ | peroxisome proliferator activated receptor gamma | 1.202532 | 0.414603 | 0.380897 | 0.311466 |
| NM_009605 | Adipoq | adiponectin, C1Q and collagen domain containing | 0.257089 | 0.063623 | 0.0252 | 0.106677 |

TABLE 3

Gene expression in ob/ob wound

| GenBank Accession No. | Symbol | Gene Description | Day 0 | Day 3 | Day 5 | Day 7 |
|---|---|---|---|---|---|---|
| NM_021274.1 | CXCL10 | chemokine (C-X-C motif) ligand 10 | 0.250498 | 1.126345 | 1.284465 | 0.778731 |
| NM_009283 | STAT 1 | signal transducer and activator of transcription 1 | 1.007855 | 1.307954 | 2.155304 | 0.929762 |
| NM_008808.3 | PDGFA | platelet derived growth factor, alpha | 0.300793 | 0.745053 | 1.267399 | 0.900313 |
| BC109135 | IL1R1 | interleukin 1 receptor, type I | 0.921124 | 1.726157 | 3.633038 | 0.723038 |
| NM_011577.1 | TGFB1 | transforming growth factor, beta 1 | 0.549678 | 1.355657 | 3.658518 | 1.551075 |
| NM_008402 | ITGAV | integrin alpha V | 1.486966 | 2.218466 | 3.554344 | 1.225875 |
| NM_011905 | TLR2 | toll-like receptor 2 | 0.489705 | 2.922228 | 2.985972 | 0.923871 |
| NM_011333.3 | CCL2 | chemokine (C-C motif) ligand 2 | 0.214683 | 8.392496 | 5.935198 | 0.475682 |
| NM_008279.2 | MAP4K1 | mitogen-activated protein kinase kinase kinase kinase 1 | 0.278249 | 0.832453 | 0.819214 | 0.485642 |
| NM_009532 | XRCC1 | x-ray repair complementing defective repair in Chinese hamster cells 1 | 3.86801 | 0.530499 | 1.031126 | 1.463049 |
| NM_011593 | TIMP1 | tissue inhibitor of metalloproteinase 1 | 0.092007 | 0.675698 | 0.641478 | 0.402068 |
| NM_010548.2 | IL-10 | interleukin 10 | 0.297165 | 1.451524 | 1.288575 | 0.369205 |
| NM_010431 | HIF1A | hypoxia inducible factor 1, alpha subunit | 0.895448 | 1.387657 | 0.906589 | 0.679313 |
| NM_008599.4 | CXCL9 | chemokine (C-C motif) ligand 9 | 1.157953 | 2.190138 | 2.601004 | 2.928437 |
| NM_009141.2 | CXCL5 | chemokine (C-X-C motif) ligand 5 | 0.501839 | 40.88581 | 49.65191 | 1.426044 |
| NM_007707 | SOCS3 | Suppressor of cytokine signaling 3 | 1.077089 | 5.065714 | 2.008733 | 0.98434 |
| NM_009507.3 | VHL | von Hippel-Lindau tumor suppressor | 1.440808 | 2.150269 | 2.576122 | 1.480475 |
| NM_009263 | OPN (Spp1) | secreted phosphoprotein 1 | 0.321897 | 11.29194 | 9.79651 | 2.078165 |
| NM_013693 | TNFA | Tumor necrosis factor, alpha | 0.058466 | 1.534815 | 0.864856 | 0.825961 |
| NM_008176 | CXCL1 | chemokine (C-X-C motif) ligand 1 | 0.103358 | 7.129337 | 4.410788 | 0.470175 |
| NM_009652.3 | AKT1 | thymoma viral proto-oncogene 1 | 1.134636 | 1.321611 | 2.016966 | 0.934964 |
| NM_020581.2 | ANGPTL4 | angiopoietin-like 4 | 0.052951 | 0.511414 | 0.222601 | 0.264857 |
| NM_011057.3 | PDGFB | platelet derived growth factor, B polypeptide | 0.669607 | 1.105467 | 1.523259 | 1.420103 |
| NM_001081117.2 | Ki67 | antigen identified by monoclonal antibody Ki 67 | 1.853563 | 3.629809 | 4.337301 | 2.799198 |
| NM_010427.4 | HGF | hepatocyte growth factor | 0.160628 | 1.743398 | 2.166984 | 0.765072 |
| AF016189.1 | Smad3 | MAD homolog 3 | 0.742435 | 0.750201 | 0.441932 | 0.334552 |
| NM_010143 | EPHB3 | Eph receptor B3 | 0.389309 | 1.173355 | 0.966125 | 0.874948 |
| NM_008037 | FOSL2 (FRA2) | fos-like antigen 2 | 0.389147 | 1.190892 | 0.566979 | 0.473821 |
| NM_010140 | EPHA3 | Eph receptor A3 | 0.856996 | 0.32359 | 2.581308 | 0.473749 |
| NM_207655 | EGFR | epidermal growth factor receptor | 1.023921 | 0.713711 | 1.00082 | 0.563818 |
| NM_009505 | VEGFA | vascular endothelial growth factor A | 1.317539 | 1.37243 | 1.666211 | 0.653953 |
| NM_009870 | CDK4 | cyclin-dependent kinase 4 | 0.813738 | 1.337735 | 1.360731 | 1.260869 |
| NM_007556 | BMP6 | bone morphogenetic protein 6 | 4.061546 | 1.445786 | 2.047303 | 0.103315 |
| NM_001033239 | CSTA | Cystatin A | 0.508856 | 27.13025 | 12.53943 | 3.082821 |
| NM_008108 | GDF3 | growth differentiation factor 3 | 0.136515 | 4.965691 | 6.24347 | 2.480356 |
| NM_011386.2 | SKIL (SnoN) | Ski like | 2.759996 | 8.323164 | 7.297358 | 4.831205 |
| NM_008416 | JUN-B | Jun-B oncogene | 0.152556 | 3.172094 | 1.526778 | 1.134647 |
| NM_008380 | INHBA | Inhibin, beta A | 0.919534 | 2.784224 | 5.537288 | 1.897602 |
| NM_009896 | SOCS1 | suppressor of cytokine signaling 1 | 1.497767 | 4.148567 | 3.142511 | 1.11581 |
| NM_021297 | TLR4 | toll-like receptor 4 | 0.713236 | 2.706313 | 2.601621 | 0.831974 |
| NM_007404 | ADAM9 | a disintegrin and metallopeptidase domain 9 | 1.481524 | 1.773434 | 1.590105 | 0.674012 |
| NM_008607 | MMP13 | matrix metallopeptidase 13 | 0.196111 | 1.485535 | 1.072455 | 1.113487 |
| NM_008871 | PAI1 (Serpine 1) | serine (or cysteine) peptidase inhibitor, Glade E, member 1 | 0.82794 | 0.50429 | 0.910365 | 1.288952 |
| NM_013599 | MMP9 | matrix metallopeptidase 9 | 0.48696 | 9.389738 | 5.523574 | 1.92419 |
| NM_007426.3 | ANGPT2 | angiopoietin 2 | 2.597985 | 0.522414 | 1.412809 | 0.544707 |
| NM_011607 | TNC | tenascin C | 0.196003 | 9.033474 | 22.59936 | 7.270111 |
| NM_031168.1 | IL-6 | interleukin 6 | 0.195309 | 8.340513 | 5.607855 | 1.92322 |
| NM_011580 | TSP-1 | thrombospondin 1 | 0.178282 | 2.934585 | 1.655054 | 1.467634 |
| NM_011145.3 | PPARβ/δ | peroxisome proliferator activated receptor beta/delta | 0.514494 | 2.530547 | 2.382542 | 1.719608 |
| NM_009242 | SPARC | secreted acidic cysteine rich glycoprotein | 0.766017 | 0.643615 | 1.251748 | 0.803739 |
| NM_031199.3 | TGFA | transforming growth factor, alpha | 2.332045 | 5.16867 | 4.421783 | 2.799128 |
| NM_007670.4 | p15 (CDKN2B) | cyclin-dependent kinase inhibitor 2B | 1.499122 | 0.705773 | 1.415514 | 1.639463 |
| NM_009969.4 | GM-CSF | Colony stimulating factor 2 | 0.532663 | 1.575585 | 0.216542 | 3.897695 |
| NM_009370.2 | TGFBR1 (ALK5) | transforming growth factor, beta receptor I | 2.250052 | 2.189751 | 1.554899 | 1.632469 |
| NM_010296.2 | GLI1 | GLI-Kruppel family member GLI1 | 0.777933 | 0.523369 | 0.833232 | 0.629003 |
| NM_029993.1 | Mlana | melan-A | 0.163832 | 0.130891 | 0.13634 | 1.018998 |
| NM_009640.3 | ANGPT1 | angiopoietin 1 | 0.271623 | 0.541881 | 0.486119 | 0.274159 |

TABLE 3-continued

Gene expression in ob/ob wound

| GenBank Accession No. | Symbol | Gene Description | Day 0 | Day 3 | Day 5 | Day 7 |
|---|---|---|---|---|---|---|
| NM_008816.2 | PECAM1 | platelet/endothelial cell adhesion molecule 1 | 1.026536 | 1.012497 | 1.271402 | 0.708473 |
| NM_010638 | KLF-9 | Kruppel-like factor 9 | 1.401337 | 0.431655 | 0.642859 | 0.400448 |
| NM_011330.3 | CCL11 | chemokine (C-C motif) ligand 11 | 0.969593 | 0.610924 | 0.957601 | 0.415014 |
| NM_008008.4 | KGF (FGF7) | fibroblast growth factor 7 | 0.595196 | 1.110988 | 0.99184 | 0.680341 |
| NM_007987.2 | FAS | Fas (TNF receptor superfamily member 6) | 0.439816 | 0.099373 | 0.224529 | 0.189167 |
| NM_011488 | STAT 5A | signal transducer and activator of transcription 5A | 0.852498 | 0.754894 | 1.008012 | 0.39186 |
| NM_008036 | FOSB | FBJ osteosarcoma oncogene B | 0.474459 | 2.473119 | 0.902717 | 0.39987 |
| BC003806 | STAT 3 | signal transducer and activator of transcription 3 | 0.838114 | 1.418559 | 0.857724 | 0.241829 |
| NM_011952 | MAPK3 (1b) | mitogen-activated protein kinase 3 | 0.597765 | 0.716862 | 0.944315 | 0.538358 |
| NM_007464 | IAP2 | intracisternal A particle 2 | 0.881733 | 0.995298 | 0.952775 | 0.67237 |
| NM_008360.1 | IL-18 | interleukin 18 | 0.599095 | 0.486806 | 0.888455 | 0.438703 |
| NM_010517 | IGFBP4 | insulin-like growth factor binding protein 4 | 0.847077 | 0.400526 | 1.231736 | 0.448635 |
| NM_009396.2 | TNFAIP2 | tumor necrosis factor, alpha-induced protein 2 | 1.334465 | 0.900658 | 0.394656 | 0.630798 |
| NM_016802 | RHOA | ras homolog gene family, member A | 0.656541 | 1.501634 | 1.183005 | 0.931674 |
| NM_008006.2 | FGF2 | fibroblast growth factor 2 | 1.317701 | 0.766727 | 0.71361 | 0.258482 |
| NM_009367.3 | TGFB2 | transforming growth factor, beta 2 | 1.267494 | 1.106269 | 0.693061 | 0.685656 |
| NM_011594 | TIMP2 | tissue inhibitor of metalloproteinase 2 | 0.615494 | 0.690985 | 1.270724 | 0.564646 |
| NM_010197.3 | FGF1 | fibroblast growth factor 1 | 1.809058 | 1.298661 | 1.220293 | 0.831763 |
| NM_011595.2 | TIMP3 | tissue inhibitor of metalloproteinase 3 | 1.082271 | 0.327056 | 0.547626 | 0.453588 |
| NM_011144.6 | PPARα | peroxisome proliferator activated receptor alpha | 1.358423 | 0.585544 | 0.716725 | 0.619864 |
| NM_001127330.1 | PPARγ | peroxisome proliferator activated receptor gamma | 1.476165 | 0.92328 | 0.820091 | 0.4815 |
| NM_009605 | Adipoq | adiponectin, C1Q and collagen domain containing | 0.525416 | 0.118814 | 0.081237 | 0.050903 |

TABLE 4

Gene expression of ANGPTL4 treated ob/ob wound

| GenBank Accession No. | Symbol | Gene Description | Day 0 | Day 3 | Day 5 | Day 7 |
|---|---|---|---|---|---|---|
| NM_021274.1 | CXCL10 | chemokine (C-X-C motif) ligand 10 | 0.304805 | 0.72315 | 0.61108 | 0.735198 |
| NM_009283 | STAT 1 | signal transducer and activator of transcription 1 | 0.874987 | 1.040915 | 1.396994 | 1.175607 |
| NM_008808.3 | PDGFA | platelet derived growth factor, alpha | 0.621069 | 0.776066 | 0.783335 | 1.075653 |
| BC109135 | IL1R1 | interleukin 1 receptor, type I | 0.733946 | 0.774809 | 1.310378 | 0.999163 |
| NM_011577.1 | TGFB1 | transforming growth factor, beta 1 | 0.369609 | 1.017253 | 0.795357 | 0.789618 |
| NM_008402 | ITGAV | integrin alpha V | 0.911172 | 0.888832 | 1.301828 | 1.306485 |
| NM_011905 | TLR2 | toll-like receptor 2 | 0.586651 | 0.942771 | 0.810887 | 0.921544 |
| NM_011333.3 | CCL2 | chemokine (C-C motif) ligand 2 | 0.17887 | 0.676531 | 0.822543 | 0.350045 |
| NM_008279.2 | MAP4K1 | mitogen-activated protein kinase kinase kinase kinase 1 | 0.206677 | 0.70255 | 0.531403 | 0.559055 |
| NM_009532 | XRCC1 | x-ray repair complementing defective repair in Chinese hamster cells 1 | 0.778193 | 0.964759 | 0.794793 | 0.816166 |
| NM_011593 | TIMP1 | tissue inhibitor of metalloproteinase 1 | 0.12779 | 0.481093 | 0.376945 | 0.322528 |
| NM_010548.2 | IL-10 | interleukin 10 | 0.361614 | 0.923416 | 0.915123 | 0.573573 |
| NM_010431 | HIF1A | hypoxia inducible factor 1, alpha subunit | 1.107043 | 0.888913 | 1.23845 | 1.028589 |
| NM_008599.4 | CXCL9 | chemokine (C-C motif) ligand 9 | 0.337254 | 0.683759 | 0.951498 | 1.139836 |
| NM_009141.2 | CXCL5 | chemokine (C-X-C motif) ligand 5 | 0.506209 | 0.506209 | 0.588989 | 0.520007 |
| NM_007707 | SOCS3 | Suppressor of cytokine signaling 3 | 0.586651 | 0.546553 | 0.535127 | 0.743986 |
| NM_009507.3 | VHL | von Hippel-Lindau tumor suppressor | 0.730746 | 0.713839 | 1.030148 | 1.036704 |
| NM_009263 | OPN (Spp1) | secreted phosphoprotein 1 | 0.231809 | 0.246915 | 0.584065 | 0.477398 |
| NM_013693 | TNFA | Tumor necrosis factor, alpha | 0.073604 | 0.323993 | 0.097211 | 0.288435 |
| NM_008176 | CXCL1 | chemokine (C-X-C motif) ligand 1 | 0.142404 | 0.409071 | 0.213149 | 0.343446 |
| NM_009652.3 | AKT1 | thymoma viral proto-oncogene 1 | 1.016809 | 1.022835 | 1.141897 | 1.084718 |
| NM_020581.2 | ANGPTL4 | angiopoietin-like 4 | 0.118174 | 0.551698 | 0.776718 | 0.951234 |
| NM_011057.3 | PDGFB | platelet derived growth factor, B polypeptide | 0.838878 | 0.937201 | 0.865232 | 1.155474 |

TABLE 4-continued

Gene expression of ANGPTL4 treated ob/ob wound

| GenBank Accession No. | Symbol | Gene Description | Day 0 | Day 3 | Day 5 | Day 7 |
|---|---|---|---|---|---|---|
| NM_001081117.2 | Ki67 | antigen identified by monoclonal antibody Ki 67 | 0.80973 | 0.731895 | 0.984001 | 0.912941 |
| NM_010427.4 | HGF | hepatocyte growth factor | 0.529111 | 0.883645 | 1.340757 | 1.247646 |
| AF016189.1 | Smad3 | MAD homolog 3 | 0.954324 | 0.885912 | 0.521233 | 0.896738 |
| NM_010143 | EPHB3 | Eph receptor B3 | 0.638463 | 0.648164 | 0.967867 | 1.213741 |
| NM_008037 | FOSL2 (FRA2) | fos-like antigen 2 | 0.517498 | 0.504218 | 0.424239 | 0.81525 |
| NM_010140 | EPHA3 | Eph receptor A3 | 0.8117 | 0.984998 | 0.709375 | 0.800224 |
| NM_207655 | EGFR | epidermal growth factor receptor | 0.99315 | 0.900182 | 1.408017 | 1.057561 |
| NM_009505 | VEGFA | vascular endothelial growth factor A | 1.205035 | 0.925818 | 1.175286 | 0.980901 |
| NM_009870 | CDK4 | cyclin-dependent kinase 4 | 0.796204 | 1.070902 | 0.861631 | 0.894941 |
| NM_007556 | BMP6 | bone morphogenetic protein 6 | 0.997043 | 0.875784 | 1.168805 | 0.787381 |
| NM_001033239 | CSTA | Cystatin A | 0.344823 | 0.271149 | 0.836511 | 1.096416 |
| NM_008108 | GDF3 | growth differentiation factor 3 | 0.441969 | 0.933849 | 0.607563 | 0.893294 |
| NM_011386.2 | SKIL (SnoN) | Ski like | 0.714242 | 0.601057 | 1.014233 | 1.240276 |
| NM_008416 | JUN-B | Jun-B oncogene | 0.259351 | 0.412261 | 0.324982 | 0.478694 |
| NM_008380 | INHBA | Inhibin, beta A | 0.437202 | 0.407295 | 0.243947 | 0.607651 |
| NM_009896 | SOCS1 | suppressor of cytokine signaling 1 | 1.154803 | 0.952236 | 0.621538 | 1.058868 |
| NM_021297 | TLR4 | toll-like receptor 4 | 0.439488 | 0.821909 | 1.18585 | 1.06559 |
| NM_007404 | ADAM9 | a disintegrin and metallopeptidase domain 9 | 0.908046 | 0.828969 | 1.205345 | 0.672844 |
| NM_008607 | MMP13 | matrix metallopeptidase 13 | 0.37852 | 0.430121 | 0.446309 | 0.750303 |
| NM_008871 | PAI1 (Serpine 1) | serine (or cysteine) peptidase inhibitor, clade E, member 1 | 0.693599 | 0.265534 | 0.833235 | 0.82168 |
| NM_013599 | MMP9 | matrix metallopeptidase 9 | 0.417162 | 0.256081 | 0.727659 | 0.86045 |
| NM_007426.3 | ANGPT2 | angiopoietin 2 | 1.188643 | 0.909358 | 1.040691 | 0.437665 |
| NM_011607 | TNC | tenascin C | 0.195806 | 0.688135 | 0.605638 | 1.082937 |
| NM_031168.1 | IL-6 | interleukin 6 | 0.370696 | 0.403678 | 0.662347 | 0.550118 |
| NM_011580 | TSP-1 | thrombospondin 1 | 0.417082 | 0.823719 | 0.698756 | 0.862384 |
| NM_011145.3 | PPARβ/δ | peroxisome prolifeator activated receptor beta/delta | 0.88324 | 0.938287 | 1.672059 | 0.818705 |
| NM_009242 | SPARC | secreted acidic cysteine rich glycoprotein | 0.702669 | 0.944087 | 0.739896 | 0.682164 |
| NM_031199.3 | TGFA | transforming growth factor, alpha | 0.894606 | 0.816341 | 0.857122 | 1.168371 |
| NM_007670.4 | p15 (CDKN2B) | cyclin-dependent kinase inhibitor 2B | 0.644314 | 0.440738 | 0.691463 | 1.036704 |
| NM_009969.4 | GM-CSF | Colony stimulating factor 2 | 0.578629 | 0.584404 | 0.182076 | 1.03733 |
| NM_009370.2 | TGFBR1 (ALK5) | transforming growth factor, beta receptor I | 1.091881 | 1.005272 | 1.024559 | 1.24505 |
| NM_010296.2 | GLI1 | GLI-Kruppel family member GLI1 | 1.202765 | 0.587583 | 1.879333 | 1.169478 |
| NM_029993.1 | Mlana | melan-A | 0.363229 | 0.317839 | 0.34455 | 0.61259 |
| NM_009640.3 | ANGPT1 | angiopoietin 1 | 0.309335 | 0.558803 | 0.808304 | 0.402088 |
| NM_008816.2 | PECAM1 | platelet/endothelial cell adhesion molecule 1 | 1.000219 | 1.019195 | 1.595884 | 1.206357 |
| NM_01-0638 | KLF-9 | Kruppel-like factor 9 | 1.108882 | 1.096597 | 0.619882 | 0.588176 |
| NM_011330.3 | CCL11 | chemokine (C-C motif) ligand 11 | 0.74805 | 1.011156 | 1.428584 | 0.610392 |
| NM_008008.4 | KGF (FGF7) | fibroblast growth factor 7 | 0.66413 | 0.814812 | 1.356676 | 1.011362 |
| NM_007987.2 | FAS | Fas (TNF receptor superfamily member 6) | 0.482059 | 0.886083 | 0.957834 | 0.456364 |
| NM_011488 | STAT 5A | signal transducer and activator of transcription 5A | 0.781767 | 1.043411 | 0.924494 | 0.786155 |
| NM_008036 | FOSB | FBJ osteosarcoma oncogene B | 0.52427 | 0.49588 | 0.562765 | 0.468561 |
| BC003806 | STAT 3 | signal transducer and activator of transcription 3 | 0.903481 | 1.014231 | 0.678205 | 0.801492 |
| NM_011952 | MAPK3 (1b) | mitogen-activated protein kinase 3 | 0.669488 | 0.992064 | 0.553663 | 0.610035 |
| NM_007464- | IAP2 | intracisternal A particle 2 | 0.897358 | 0.903178 | 1.243896 | 0.923667 |
| NM_008360.1 | IL-18 | interleukin 18 | 0.629251 | 0.846648 | 1.027115 | 0.944054 |
| NM_010517 | IGFBP4 | insulin-like growth factor binding protein 4 | 0.811006 | 1.044133 | 0.837465 | 0.835327 |
| NM_009396.2 | TNFAIP2 | tumor necrosis factor, alpha-induced protein 2 | 1.362517 | 0.820266 | 0.973071 | 1.117801 |
| NM_016802 | RHOA | ras homolog gene family, member A | 0.897189 | 0.894252 | 1.133156 | 1.211557 |
| NM_008006.2 | FGF2 | fibroblast growth factor 2 | 1.11818 | 0.719789 | 1.409345 | 0.467684 |
| NM_009367.3 | TGFB2 | transforming growth factor, beta 2 | 1.141916 | 1.096597 | 0.866636 | 0.981726 |
| NM_011594 | TIMP2 | tissue inhibitor of metalloproteinase 2 | 0.656663 | 0.976303 | 1.102946 | 0.68267 |
| NM_010197.3 | FGF1 | fibroblast growth factor 1 | 1.271444 | 0.853071 | 0.962985 | 1.246809 |
| NM_011595.2 | TIMP3 | tissue inhibitor of metalloproteinase 3 | 0.953652 | 1.081293 | 1.029595 | 0.691683 |
| NM_011144.6 | PPARα | peroxisome proliferator activated receptor alpha | 1.227201 | 0.859424 | 1.228189 | 1.207679 |

TABLE 4-continued

Gene expression of ANGPTL4 treated ob/ob wound

| GenBank Accession No. | Symbol | Gene Description | Day 0 | Day 3 | Day 5 | Day 7 |
|---|---|---|---|---|---|---|
| NM_001127330.1 | PPARγ | peroxisome proliferator activated receptor gamma | 0.951977 | 0.809746 | 1.381111 | 1.150956 |
| NM_009605 | Adipoq | adiponectin, C1Q and collagen domain containing | 0.420466 | 0.858938 | 1.396699 | 0.220694 |
| NM_021274.1 | CXCL10 | chemokine (C-X-C motif) ligand 10 | 0.304805 | 0.72315 | 0.61108 | 0.735198 |

To further understand how ANGPTL4 improves the healing rate of diabetic wounds, we examined the time course expression of specific protein markers such as endothelial cell marker (CD31), alpha smooth muscle actin (αSMA), cell proliferating marker (PCNA), and macrophage marker (F4/80) in ob/ob treated with ANGPTL4 compared with ob/+ and ob/ob using western blotting as described in Example 3. As expected, saline-treated ob/ob wounds displayed a reduced expression of CD31 and αSMA since day 3 post wounding when compared with the normal ob/+ wounds (FIG. 2D, E). Notably, the expression profiles of CD31 and αSMA of cANGPTL4-treated ob/ob wounds were similar to ob/+(FIG. 2D, E).

Consistent with the western blot data, immunofluorescence staining of CD31, as described in Example 3, on day 5 post wounded biopsies showed increase in endothelial vasculature in cANGPTL4-treated ob/ob wounds compared with saline-treated ob/ob wounds (FIG. 2F). In contrast to ob/+ wounds, the expression of F4/80 and PCNA in ob/ob wounds was remained elevated until day 10 post wounding, suggesting a persistent infiltration and activation of macrophages (FIG. 2D, E). Although the expression pattern of F4/80 and PCNA in ANGPTL4-treated wounds remain unchanged compared to saline control, their overall expression level was slightly reduced (FIG. 2D). Taken together, the observations suggest that ANGPTL4 improves angiogenesis of diabetic wounds.

Example 5

ANGPTL4 regulate the NO production profile in ob/ob wounds. To understand how ANGPTL4 modulate angiogenesis, we examined the level of NO, which is a potent mediator of angiogenesis. Our earlier focused gene array analysis also revealed that the expression of iNOS was dramatically increased in ANGPTL4-treated ob/ob wounds compared with saline treatment (see FIG. 2B). Nitric oxide has been shown to improve tissue repair by promoting endothelial proliferation, keratinocytes migration, and indirectly reducing inflammation.

Intracellular level of NO from wound biopsies were measured using cell-permeable 4,5-diamino-fluorescein (DAF-FM diacetate) (Invitrogen, USA). Wound biopsies were lysed in Krebs buffer, and incubated with 10 µM DAF-FM diacetate for 30 min at 37° C. in darkness. The fluorophore signal was recorded immediately at 495 nm excitation and 515 nm emission wavelengths using a GloMax 20/20 Luminometer (Promega, USA). Fluorescence was expressed as arbitrary fluorescence units (AU), and was measured with the same instrument settings for all experiments.

Using DAF-FM diacetate, we compared the NO level in post-wound biopsies from saline- and ANGPTL4-treated ob/ob. We observed overall reduced NO level in ob/ob wounds when compared with ob/+ wounds (FIG. 3A). ANGPTL4-treated ob/ob wounds showed significant increase in NO production from day 3 post-wounding onwards when compared with saline control, suggesting that ANGPTL4 may mediate NO production (FIG. 3A). Using DAF-FM diacetate fluorescence staining on wound biopsies, we observed that NO level was elevated in ANGPTL4-treated ob/ob wound tissue, particularly at the wound epithelia and in the dermal wound bed (FIG. 8A). To further understand the underlying mechanism, we examined the mRNA expression of iNOS, eNOS and NO level at indicated days post wounding. In contrast to ob/+ wounds whose eNOS expression peaked at day 7 post wounding, the expression of eNOS in ob/ob wounds peaked earlier at day 3 post-wounding (FIG. 3B, left panel). The treatment with ANGPTL4 shifted the peak expression of eNOS to day 5 post wounding, but has no impact on the expression level, suggesting that this may be a secondary effect. We further confirm that ANGPTL4 does not modulate the expression of eNOS using primary human dermal microvascular endothelial cells (FIG. 3B, right panel). Our result showed diabetic ob/ob mice expressed little iNOS mRNA when compared to normal ob/+ mice whose iNOS expression peaked transiently at day 3 post-injury. The ANGPTL4 treatment of diabetic wounds increased iNOS expression, albeit peaking at day 7 post-injury (FIG. 3C, left panel). We further confirmed that ANGPTL4 increases the expression of iNOS in fibroblasts (FIG. 3C, right panel) and immunofluorescence staining, as described in Example 3, of day 7 wound biopsies (FIG. 3D). Altogether, the observations suggest that the treatment of ANGPTL4 modulates the expression of iNOS, which increases NO generation at the wound site.

Example 6

ANGPTL4 regulates iNOS expression. ANGPTL4$^{-/-}$ mice showed impaired angiogenesis during wound healing. Diabetic wounds are characterized by poor wound-related angiogenesis [1], which similarly expressed low level of ANGPTL4 protein (FIG. 1D). The pro-angiogenic role of NO is known [18-20]. However, how ANGPTL4 modulates iNOS and thus NO generation remains unclear. ANGPTL4 binds to integrin, activates focal adhesion kinase and subsequently downstream mediators such as ERK1 and STATs to modulate gene expression and cell behavior [17,21]. The transcription factors STAT and NF-κB have been shown to transcriptionally regulate the expression of iNOS [22]. Thus, we first examined the expression level of phosphorylated STAT1, 3 and NF-κB in wound biopsies by immunofluorescence staining as described in Example 3. We observed elevated levels of phosphorylated STAT1, 3 and NF-κB in ob/ob wounds treated with cANGPTL4 compared with saline control (FIG. 4A). Next, we performed in vivo chromatin immunoprecipitation (ChIP) to determine these transcription factors were bound to the regulatory region of mouse iNOS gene. Our ChIP showed that phospho-STAT1, STAT3 and NF-κB specifically bound to their cognate responsive elements in the promoter of mouse iNOS gene in ANGPTL4-treated but not in saline-treated ob/ob wounds (FIG. 4B). No immunoprecipitation and amplification were seen with pre-immune IgG and with a control sequence upstream of the responsive elements in the promoter iNOS gene (FIG. 4B). Nitric oxide has been shown to regulate gene expression and protein activities by transcriptional-independent stabilization of mRNA and modifications of cellular protein targets, respectively [23,24]. Of particular interest, we observed that the mRNA expression of transcriptional factor Inhibitor of DNA binding 3 (ID3) was elevated in primary fibroblasts treated with ANGPTL4 (FIG. 4C). Nitric oxide has been shown to stabilize ID3 mRNA[23]. Thus, we examined the mRNA level in fibroblasts treated with either ANGPTL4 or saline in the presence of actinomycin D. Our data revealed a slower decrease in ID3 mRNA level in ANGPTL4-treated fibroblasts compared to saline treatment (FIG. 4D). Altogether, these observations indicate that ANGPTL4 stimulates the level of NO generation, at least through a mechanism that involves the transcriptional regulation of iNOS gene via the direct binding of STAT1, 3 and NF-κB onto the promoter. In addition, we further showed that ANGPTL4-induced NO production stabilizes ID3 mRNA.

Example 7

ANGPTL4 reduce collagen deposition in ob/ob wounds. Delayed diabetic wound healing lead to excessive production and deposition of collagen at the wound bed, which at least in part may be attributed to reduce NO level. Studies have shown that expression of NOS and NO production are decreased in human hypertrophic scar and diabetic wounds[27,28]. To address whether ANGPTL4 may influence the level of scarring, we measure collagen deposition in the saline- and cANGPTL4-treated ob/ob wounds. First, we measured the amount of hydroxyproline, a major component of collagen, from each wound biopsies of saline-treated and ANGPTL4-treated ob/ob wounds.

Hydroxyproline Assay. Wound biopsies were frozen in liquid nitrogen, and then homogenized thoroughly in distilled water. The net weight of the wound biopsies was predetermined for normalization. In addition, trans-4-hydroxy-L-proline (0-300 μg/mL) was included as standards. Aliquots of samples (50 μl) were hydrolyzed in 2 N NaOH at 120° C. for 2 hours, and then oxidized with chloramine-T reagent (0.0127 g/mL) for 25 min at room temperature. The chromophore was then developed with the addition of p-dimethylaminobenzaldehyde (DMBA) reagent (0.3 g/mL dissolved in methanol/hydrochloric acid solution (2:1 v/v)). The absorbance of reddish hue complex formed was measured at 550 nm using SpectraMax® M2e Multi-Mode Microplate Reader and SoftMax® Pro Microplate Data Acquisition & Analysis Software (Molecular Devices, USA). Absorbance values were plotted against the concentration of standard hydroxyproline, and the value of unknown hydroxyproline were then determined from the standard curve.

We detected a reduced level of hydroxyproline only with wound biopsies at day 10 post-injury, where complete wound closure was observed in ANGPTL4-treated wounds (FIGS. 5A and 2A). Van Gieson staining of wound Tissue sections from mice wound biopsies were deparaffinized and rehydrated in PBS. These sections were stained in Weigert's iron haematoxylin for 8 min at room temperature followed by staining in picric-fuchsin solution for 1 min at room. The Van Gieson staining showed a reduction in collagen deposition at the wound bed in cANGPTL4-treated ob/ob wounds when compared to saline-treated ob/ob wounds (FIG. 5B).

Next, we co-treated ob/ob wounds with ANGPTL4 and aminoguanidine, a selective inhibitor of iNOS. Consistent with our above findings, wound re-epithelialisation was delayed (FIG. 9) and the wound site had higher level of collagen deposition, as evidenced by Masson trichrome stain (FIG. 5C). To further confirm our observation that ANGPTL4 reduced collagen scar tissue, we used scanning and transmission electron microscopy to characterize the architectural arrangement of collagen fibers in saline- and ANGPTL4-treated ob/ob wounds. As expected, collagen fibrils of saline-treated wounds were thicker and in a pronounced alignment in a single direction (FIG. 5D), pointing to scar tissue formation. In contrast, collagen fibrils in ANGPTL4-treated wounds were thinner and in a randomised alignment (FIG. 5D). Taken together, we showed that ANGPTL4 accelerated re-epithelialization and reduced collagen scar tissue in ob/ob diabetic wounds.

Example 8

Reagents. Antibodies used: Ki67 and keratin 6 (Novo-Castra); PCNA (PC10) and αSMA (alpha-SM1) (Santa Cruz Biotechnology); CD31 (BD Pharmingen); CD68 (FA-11) (Biolegend); F4/80 (AbD Serotec); cANGPTL4: monoclonal antibodies against the C-terminal mouse (190-410 amino acids) of ANGPTL4 were produced by ProSci, respectively; goat anti-rabbit and anti-mouse IgG-HRP (Santa Cruz Biotechnology); Alexa Fluor 488 or 594 goat anti-mouse IgG, anti-rat IgG and anti-rabbit IgG (Molecular probes). DAB peroxidase substrate kit (Vector Laboratories). Unless mentioned otherwise, all chemicals were from Sigma-Aldrich and molecular biology enzymes from Fermentas. All oligonucleotides were synthesized by Sigma-Proligo.

Example 9

Assessment of wound healing. Images of wounds were captured at Day 1, 3, 5, 7 and 10 post-wounding using a Canon G12 digital camera. A ruler was included in each image to allow standard calibration of measurements. Surface wound area was quantified using Image-Pro® Plus version 5.1.0.20 software (Media Cybernetics, USA). Surface wound area at each time point were standardized and expressed as a percentage of initial wound area at Day 1 (100%). Histomorphometric measurement was made from sections through the center of the wound to obtain the actual wound representation. Sections of wound biopsies over the indicated time were stained by haematoxylin-eosin staining. Histological images were visualized with Nikon Eclipse 90i brightfield microscope using a Plan Fluor, 10x/0.30 objective and taken with QCapture Pro version 5.0.1.26 software (QImaging). The measurements were performed three times from random sections using Adobe Photoshop CS5.1 and image pixel was calibrated to μm using the scale bar.

By "comprising" it is meant including, but not limited to, whatever follows the word "comprising". Thus, use of the term "comprising" indicates that the listed elements are required or mandatory, but that other elements are optional and may or may not be present.

By "consisting of" is meant including, and limited to, whatever follows the phrase "consisting of". Thus, the phrase "consisting of" indicates that the listed elements are required or mandatory, and that no other elements may be present.

The inventions illustratively described herein may suitably be practiced in the absence of any element or elements, limitation or limitations, not specifically disclosed herein. Thus, for example, the terms "comprising", "including", "containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the inventions embodied therein herein disclosed may be resorted to by those skilled in the art, and that such modifications and variations are considered to be within the scope of this invention.

By "about" in relation to a given numerical value, such as for temperature and period of time, it is meant to include numerical values within 10% of the specified value.

The invention has been described broadly and generically herein. Each of the narrower species and sub-generic groupings falling within the generic disclosure also form part of the invention. This includes the generic description of the invention with a proviso or negative limitation removing any subject matter from the genus, regardless of whether or not the excised material is specifically recited herein.

Other embodiments are within the following claims and non-limiting examples. In addition, where features or aspects of the invention are described in terms of Markush groups, those skilled in the art will recognize that the invention is also thereby described in terms of any individual member or subgroup of members of the Markush group.

REFERENCES

1. Brem H and Tomic-Canic M, Cellular and molecular basis of wound healing in diabetes. J Clin Invest. 2007; 117: 1219-1222.
2. Delmas L, Best practice in the assessment and management of diabetic foot ulcers. Rehabil Nurs. 2006; 31: 228-234.
3. Werner S and Grose R, Regulation of wound healing by growth factors and cytokines. Physiol Rev. 2003; 83: 835-870.
4. Coulombe P A, Wound epithelialization: accelerating the pace of discovery. J Invest Dermatol. 2003; 121: 219-230.
5. Falanga V, Wound healing and its impairment in the diabetic foot. Lancet. 2005; 366: 1736-1743.
6. Blakytny R and Jude E B, Altered molecular mechanisms of diabetic foot ulcers. Int J Low Extrem Wounds. 2009; 8: 95-104.
7. Sharma A, Singh A K, Warren J, Thangapazham R L and Maheshwari R K, Differential regulation of angiogenic genes in diabetic wound healing. J Invest Dermatol. 2006; 126: 2323-2331.
8. Galkowska H, Wojewodzka U and Olszewski W L, Chemokines, cytokines, and growth factors in keratinocytes and dermal endothelial cells in the margin of chronic diabetic foot ulcers. Wound Repair Regen. 2006; 14: 558-565.
9. Chong H C, Tan C K, Huang R L and Tan N S, Matricellular proteins: a sticky affair with cancers. Journal of oncology. 2012; 2012: 351089.
10. Bornstein P, Matricellular proteins: an overview. Matrix Biol. 2000; 19: 555-556.
11. Bornstein P and Sage E H, Matricellular proteins: extracellular modulators of cell function. Curr Opin Cell Biol. 2002; 14: 608-616.
12. Zhu P, Goh Y Y, Chin H F A, Kersten S and Tan N S, Angiopoietin-like 4: a decade of research. Biosci Rep. 2012; 32: 211-219.
13. Huang R L, Teo Z, Chong H C, Zhu P, Tan M J and Tan C K et al., ANGPTL4 modulates vascular junction integrity by integrin signaling and disruption of intercellular VE-cadherin and claudin-5 clusters. Blood. 2011; 118: 3990-4002.
14. Le Jan S, Amy C, Cazes A, Monnot C, Lamandé N and Favier J et al., Angiopoietin-like 4 is a proangiogenic factor produced during ischemia and in conventional renal cell carcinoma. Am J Pathol. 2003; 162: 1521-1528.
15. Ito Y, Oike Y, Yasunaga K, Hamada K, Miyata K and Matsumoto S I et al., Inhibition of angiogenesis and vascular leakiness by angiopoietin-related protein 4. Cancer Res. 2003; 63: 6651-6657.
16. Goh Y Y, Pal M, Chong H C, Zhu P, Tan M J and Punugu L et al., Angiopoietin-like 4 interacts with matrix proteins to modulate wound healing. J Biol Chem. 2010; 285: 32999-33009.
17. Goh Y Y, Pal M, Chong H C, Zhu P, Tan M J and Punugu L et al., Angiopoietin-Like 4 Interacts with Integrins {beta}1 and {beta}5 to Modulate Keratinocyte Migration. Am J Pathol. 2010; 177: 2791-2803.
18. Chin L C, Kumar P, Palmer J A, Rophael J A, Dolderer J H and Thomas G P L et al., The influence of nitric oxide synthase 2 on cutaneous wound angiogenesis. Br J Dermatol. 2011; 165: 1223-1235.
19. Schäffer M R, Tantry U, Efron P A, Ahrendt G M, Thornton F J and Barbul A, Diabetes-impaired healing and reduced wound nitric oxide synthesis: a possible pathophysiologic correlation. Surgery. 1997; 121: 513-519.
20. Luo J D and Chen A F, Nitric oxide: a newly discovered function on wound healing. Acta Pharmacol Sin. 2005; 26: 259-264.
21. Zhu P, Tan M J, Huang R L, Tan C K, Chong H C and Pal M et al., Angiopoietin-like 4 protein elevates the prosurvival intracellular $O_2(-):H_2O_2$ ratio and confers anoikis resistance to tumors. Cancer Cell. 2011; 19: 401-415.
22. Aktan F, iNOS-mediated nitric oxide production and its regulation. Life Sci. 2004; 75: 639-653.
23. Kuwano Y, Rabinovic A, Srikantan S, Gorospe M and Demple B, Analysis of nitric oxide-stabilized mRNAs in human fibroblasts reveals HuR-dependent heme oxygenase 1 upregulation. Mol Cell Biol. 2009; 29: 2622-2635.
24. Wang S, Zhang J, Theel S, Barb J J, Munson P J and Danner R L, Nitric oxide activation of Erk1/2 regulates the stability and translation of mRNA transcripts containing CU-rich elements. Nucleic Acids Res. 2006; 34: 3044-3056.

25. Tan C K, Leuenberger N, Tan M J, Yan Y W, Chen Y and Kambadur R et al., Smad3 deficiency in mice protects against insulin resistance and obesity induced by a high-fat diet. Diabetes. 2011; 60: 464-476.
26. Tan N S, Michalik L, Di-Poi N, Ng C Y, Mermod N and Roberts A B et al., Essential role of Smad3 in the inhibition of inflammation-induced PPARbeta/delta expression. EMBO J. 2004; 23: 4211-4221.
27. Wang R, Ghahary A, Shen Y J, Scott P G, Tredget E E. Nitric oxide synthase expression and nitric oxide production are reduced in hypertrophic scar tissue and fibroblasts. J Invest Dermatol. 1997; 108: 438-44.
28. Luo, J D. and Chen, A. F. Nitric oxide: a newly discovered function on wound healing. Acta Pharmacol. Sin. 2005; 26, 259-264.

The invention claimed is:

1. A method for increasing wound healing in a diabetic individual in need thereof, the method comprising administering a therapeutically active fragment of the angiopoietin like 4 protein (ANGPTL4) consisting of the amino acid sequence set forth in SEQ ID NO:2, wherein the wound is selected from the ulcer, a chronic slow-healing wound and an open wound.

2. The method of claim 1, wherein the individual is a mammal.

3. The method of claim 2, wherein the individual is a human.

* * * * *

UNITED STATES PATENT AND TRADEMARK OFFICE
CERTIFICATE OF CORRECTION

PATENT NO. : 9,931,371 B2  
APPLICATION NO. : 14/415399  
DATED : April 3, 2018  
INVENTOR(S) : Nguan Soon Tan et al.

Page 1 of 1

It is certified that error appears in the above-identified patent and that said Letters Patent is hereby corrected as shown below:

On the Title Page

Item (73) Assignee:
"Nanyang Technologies University, Singapore (SG)" should read, --Nanyang Technological University, Singapore (SG)--.

In the Claims

Column 91, Lines 42-44:
"administering a therapeutically active fragment of the angiopoietin like 4 protein" should read, --administering a therapeutically effective amount of an angiopoietin like 4 protein--.

Column 92, Line 39:
"selected from the ulcer, a chronic slow-healing wound and" should read, --selected from an ulcer, a chronic slow-healing wound and--.

Signed and Sealed this  
Third Day of July, 2018

Andrei Iancu  
*Director of the United States Patent and Trademark Office*